US012780884B2

(12) United States Patent
Harris

(10) Patent No.: US 12,780,884 B2
(45) Date of Patent: *Nov. 3, 2026

(54) METHODS AND COMPOSITIONS FOR RAPIDLY REPLACING CARDIAC MYOSIN BINDING PROTEIN-C IN SARCOMERES

(71) Applicant: ARIZONA BOARD OF REGENTS ON BEHALF OF THE UNIVERSITY OF ARIZONA, Tucson, AZ (US)

(72) Inventor: Samantha P. Harris, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 1351 days.

This patent is subject to a terminal disclaimer.

(21) Appl. No.: 17/559,865

(22) Filed: Dec. 22, 2021

(65) Prior Publication Data

US 2022/0119469 A1 Apr. 21, 2022

Related U.S. Application Data

(63) Continuation-in-part of application No. 16/579,445, filed on Sep. 23, 2019, now Pat. No. 11,242,368.

(60) Provisional application No. 62/734,785, filed on Sep. 21, 2018.

(51) Int. Cl.
*C07K 14/47* (2006.01)

(52) U.S. Cl.
CPC ................................ *C07K 14/4716* (2013.01)

(58) Field of Classification Search
None
See application file for complete search history.

(56) References Cited

U.S. PATENT DOCUMENTS 11,242,368 B2 * 2/2022 Harris .................. C12N 15/907

OTHER PUBLICATIONS

Samantha P. Harris 37 CFR 1.132 Declaration from U.S. Appl. No. 16/579,445, filed Jun. 24, 2021. PDF copy provided. (Year: 2021).*
Previs et al. Molecular Mechanics of Cardiac Myosin-Binding Protein C in Native Thick Filaments. Science vol. 33, Sep. 7, 2012, pp. 1215-1218.
Zakeri et al. "Peptide tag forming a rapid covalent bond to a protein, through engineering a bacterial adhesion," PNAS17 Jan. 17, 2012, 10 9:E 690-697.
Reddignton and Howarth, Current Opinion in Chemical Biology 2015, 29: 94-99.
Rybakova et al.,"Myosin Binding Protein C Interaction with Actin", The Journal of Biological Chemistry, vol. 286, No. 3, pp. 2008-2016. (Jan. 2011).
Renz et al.,"Determination of AMP-activated protein kinase phosphorylation sites in recombinant protein expressed using the pET28a vector: A cautionary tale", Protein Expression and Purification 66: 181-184. (Aug. 2009).
Kapust et al. "Controlled Intracellular Processing of Fusion Proteins by TEV Protease", Protein Expression and Purification 19: 312-218. (Jul. 2000).
Sarikas et al. ,"Impairment of the ubiquitin-proteasome system by truncated cardiac myosin binding protein C mutants", Cardiovascular Research 66: 33-44. (Jan. 4, 2005).

* cited by examiner

*Primary Examiner* — Anand U Desai
(74) *Attorney, Agent, or Firm* — NGUYEN TARBET IP LAW

(57) ABSTRACT

Methods and compositions for rapidly replacing cMyBP-C in sarcomeres featuring the creation of Spy-C mice, which are mice genetically engineered to express cMyBP-C with a protease recognition site and SpyTag peptide introduced into the cMyBP-C gene. In permeabilized myocytes from the Spy-C mice, the cMyBP-C protein can be cleaved at the protease recognition site, and the N-Terminus of cMyBP-C can be removed while the C-terminus remains anchored to the thick filament. A new peptide featuring the SpyCatcher sequence can be covalently bonded to the remaining portion of cMyBP-C, thereby creating a modified cMyBP-C protein. The methods and compositions of the present invention allow for the reconstitution of full-length cMyBP-C at the precise position of native cMyBP-C in the sarcomere and allow for a variety of modifications to be introduced to cMyBP-C in situ.

16 Claims, 3 Drawing Sheets

Figure 1:
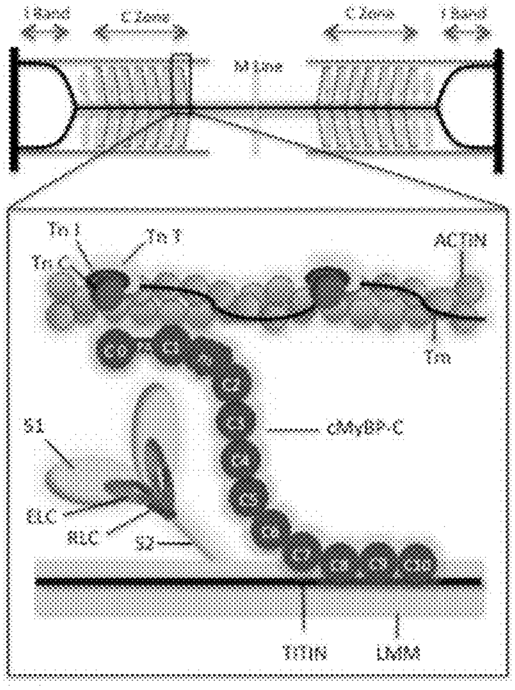

Specification includes a Sequence Listing.

SEQUENCE LISTING

<160> NUMBER OF SEQ ID NOS: 28

<210> SEQ ID NO 1
<211> LENGTH: 270
<212> TYPE: DNA
<213> ORGANISM: Artificial Sequence
<220> FEATURE:
<223> OTHER INFORMATION: SpyCatcher sequence

<400> SEQUENCE: 1

```
agcggtgata gcgcgaccca cattaaattt agcaagcgtg acgaggatgg taaagaactg      60

gcgggcgcga ccatggaact gcgtgacagc agcggcaaga ccatcagcac ctggattagc     120

gatggtcagg ttaaagactt ctacctgtat ccgggcaagt acacctttgt ggaaaccgcg     180

gcgccggatg gttatgaggt ggcgaccgcg atcaccttca ccgttaacga gcagggtcaa     240

gttaccgtga acggtaaagc gaccaagggc                                      270
```

<210> SEQ ID NO 2
<211> LENGTH: 90
<212> TYPE: PRT
<213> ORGANISM: Artificial Sequence
<220> FEATURE:
<223> OTHER INFORMATION: SpyCatcher sequence

<400> SEQUENCE: 2

```
Ser Gly Asp Ser Ala Thr His Ile Lys Phe Ser Lys Arg Asp Glu Asp
1               5                   10                  15

Gly Lys Glu Leu Ala Gly Ala Thr Met Glu Leu Arg Asp Ser Ser Gly
            20                  25                  30

Lys Thr Ile Ser Thr Trp Ile Ser Asp Gly Gln Val Lys Asp Phe Tyr
        35                  40                  45

Leu Tyr Pro Gly Lys Tyr Thr Phe Val Glu Thr Ala Ala Pro Asp Gly
    50                  55                  60

Tyr Glu Val Ala Thr Ala Ile Thr Phe Thr Val Asn Glu Gln Gly Gln
65                  70                  75                  80

Val Thr Val Asn Gly Lys Ala Thr Lys Gly
                85                  90
```

<210> SEQ ID NO 3
<211> LENGTH: 40
<212> TYPE: DNA
<213> ORGANISM: Artificial Sequence
<220> FEATURE:
<223> OTHER INFORMATION: SpyTag sequence

<400> SEQUENCE: 3

```
cgcccacatc gtgatggtcg acgcctacaa gcccaccaag                            40
```

<210> SEQ ID NO 4
<211> LENGTH: 13
<212> TYPE: PRT
<213> ORGANISM: Artificial Sequence
<220> FEATURE:
<223> OTHER INFORMATION: SpyTag seqeunce

<400> SEQUENCE: 4

```
Ala His Ile Val Met Val Asp Ala Tyr Lys Pro Thr Lys
1               5                   10
```

<210> SEQ ID NO 5
<211> LENGTH: 405
<212> TYPE: DNA

<213> ORGANISM: Artificial Sequence
<220> FEATURE:
<223> OTHER INFORMATION: SnoopCatcher sequence

<400> SEQUENCE: 5
atgggcagca gccatcatca tcatcatcac agcagcggcc tggtgccgcg cggcagccat 60
atgaagccgc tgcgtggtgc cgtgtttagc ctgcagaaac agcatcccga ctatcccgat 120
atctatggcg cgattgatca gaatgggacc tatcaaaatg tgcgtaccgg cgaagatggt 180
aaactgacct ttaagaatct gagcgatggc aaatatcgcc tgtttgaaaa tagcgaaccc 240
gctggctata aaccggtgca gaataagccg attgtggcgt ttcagattgt gaatggcgaa 300
gtgcgtgatg tgaccagcat tgtgccgcag gatattccgg ctacatatga atttaccaac 360
ggtaaacatt atatcaccaa tgaaccgata ccgccgaaat aataa 405

<210> SEQ ID NO 6
<211> LENGTH: 133
<212> TYPE: PRT
<213> ORGANISM: Artificial Sequence
<220> FEATURE:
<223> OTHER INFORMATION: SnoopCatcher sequence

<400> SEQUENCE: 6

Met Gly Ser Ser His His His His His His Ser Ser Gly Leu Val Pro
1 5 10 15

Arg Gly Ser His Met Lys Pro Leu Arg Gly Ala Val Phe Ser Leu Gln
20 25 30

Lys Gln His Pro Asp Tyr Pro Asp Ile Tyr Gly Ala Ile Asp Gln Asn
35 40 45

Gly Thr Tyr Gln Asn Val Arg Thr Gly Glu Asp Gly Lys Leu Thr Phe
50 55 60

Lys Asn Leu Ser Asp Gly Lys Tyr Arg Leu Phe Glu Asn Ser Glu Pro
65 70 75 80

Ala Gly Tyr Lys Pro Val Gln Asn Lys Pro Ile Val Ala Phe Gln Ile
85 90 95

Val Asn Gly Glu Val Arg Asp Val Thr Ser Ile Val Pro Gln Asp Ile
100 105 110

Pro Ala Thr Tyr Glu Phe Thr Asn Gly Lys His Tyr Ile Thr Asn Glu
115 120 125

Pro Ile Pro Pro Lys
130

<210> SEQ ID NO 7
<211> LENGTH: 67
<212> TYPE: DNA
<213> ORGANISM: Artificial Sequence
<220> FEATURE:
<223> OTHER INFORMATION: SnoopTag sequence

<400> SEQUENCE: 7
ggcggagaac ctgtacttcc agggcaagct gggcgacatc gagttcatca aggtgaacaa 60
gggctac 67

<210> SEQ ID NO 8
<211> LENGTH: 15
<212> TYPE: PRT
<213> ORGANISM: Artificial Sequence
<220> FEATURE:
<223> OTHER INFORMATION: SnoopTag sequence

<400> SEQUENCE: 8

Gly Lys Leu Gly Asp Ile Glu Phe Ile Lys Val Asn Lys Gly Tyr
1               5                   10                  15

<210> SEQ ID NO 9
<211> LENGTH: 21
<212> TYPE: DNA
<213> ORGANISM: Artificial Sequence
<220> FEATURE:
<223> OTHER INFORMATION: TEV Protease recognition site

<400> SEQUENCE: 9
gagaatctgt atttccaggg t                                               21

<210> SEQ ID NO 10
<211> LENGTH: 7
<212> TYPE: PRT
<213> ORGANISM: Artificial Sequence
<220> FEATURE:
<223> OTHER INFORMATION: TEV Protease recognition site
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid

<400> SEQUENCE: 10

Glu Xaa Xaa Tyr Xaa Gln Gly
1               5

<210> SEQ ID NO 11
<211> LENGTH: 7
<212> TYPE: PRT
<213> ORGANISM: Artificial Sequence
<220> FEATURE:
<223> OTHER INFORMATION: TEV Protease recognition site
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid

<400> SEQUENCE: 11

Glu Xaa Xaa Tyr Xaa Gln Ser
1               5

<210> SEQ ID NO 12
<211> LENGTH: 7
<212> TYPE: PRT
<213> ORGANISM: Artificial Sequence
<220> FEATURE:
<223> OTHER INFORMATION: TEV Protease recognition site

<400> SEQUENCE: 12

Glu Asn Leu Tyr Phe Gln Gly
1               5

<210> SEQ ID NO 13
<211> LENGTH: 3813
<212> TYPE: DNA
<213> ORGANISM: Mus musculus

<400> SEQUENCE: 13
atgccggagc cagggaagaa accagtgtca gccttcaaca agaagccaag gtcagcggag 60
gtgaccgctg gcagtgctgc cgtgttcgag gctgggacgg agcggtcagg cgtgaaggtg 120
cggtggcagc gggatggcag cgacatcacc gccaatgaca agtatggttt ggcagcagag 180
ggcaagcgac acacactgac agtgcgggat gcgagccctg atgaccaggg ttcctacgcg 240
gtcattgcag gctcctcaaa ggtcaagttt gacctcaagg tcacagagcc agcccctcca 300
gagaaggcag aatctgaagt tgctccagga gcccccaaag aagtccctgc tccagccact 360
gagttggaag aaagtgtctc aagtcctgaa gggtcagtct cggtaaccca ggatggctca 420
gctgcagagc atcagggagc ccctgatgac cctattggcc tctttctgat gcgaccacag 480
gatggtgagg tgaccgtggg cggcagcatt gtcttctcag cccgagtggc tggggccagc 540
ctcctgaaac cgcctgtggt caagtggttc aagggcaagt gggtggacct gagcagcaaa 600
gtgggccagc acctgcagct gcatgacagc tatgacagag ccagcaaggt ctacttgttt 660
gagttgcaca tcacagatgc tcagaccact tctgctgggg gctaccgctg tgaggtgtct 720
accaaggaca aatttgacag ctgtagcttc aacctcactg tccatgaggc cattggttct 780
ggagacctgg acctcagatc agctttccga cgcacgagcc tggcgggagc aggtcggaga 840
accagtgaca gccatgaaga tgctgggact ctggacttta gttccctgct gaagaagaga 900
gacagtttcc ggagggactc aaagctggag gcacctgctg aagaagacgt gtgggagatc 960
ctgagacagg caccgccgtc agaatatgag cgcatcgcct tccagcacgg agtcacagac 1020
cttcgaggca tgctgaagag gctcaagggc atgaagcagg atgaaaagaa gagcacagcc 1080
tttcagaaga agctggagcc tgcctaccag gtaaacaagg gccacaagat tcggcttact 1140
gtggaactgg ctgatccgga cgccgaagtc aagtggctta agaatggaca ggagatccag 1200
atgagtggca gcaagtacat cttcgagtcc gtcggtgcca agcgcaccct gaccatcagc 1260
cagtgctcac tggctgacga cgcagcctac cagtgtgtgg tgggggggcga gaagtgcagc 1320 acggagctct ttgtcaaaga gcccccggtg ctgatcactc ggtccctgga agaccagctg 1380
gtgatggtgg gtcagcgggt ggagtttgag tgtgaggtct cagaagaagg ggcccaagtc 1440
aaatggctga aggatggggt tgaactgaca cgtgaggaga ccttcaaata ccggttcaag 1500
aaagatgggc ggaaacacca cttgatcatc aatgaagcaa ccctggagga tgcaggacac 1560
tatgcagtac gcacaagtgg aggccagtca ctggctgagc tcattgtgca agagaagaag 1620
ttggaggtat accaaagcat cgcggacctg gcagtgggag ccaaggacca ggctgtgttt 1680
aagtgtgagg tttcagatga gaatgtacgc ggcgtgtggc tgaagaatgg gaaggaactg 1740
gtgcctgaca accgcataaa ggtgtcccat ataggccggg tccacaaact gaccattgac 1800
gatgtcacac ctgctgatga ggctgactac agctttgtcc ctgaagggtt tgcctgcaac 1860
ctgtctgcca agctccactt catggaggtc aagattgact ttgtgcctag gcaggaacct 1920
cccaagatcc acttggattg tcccggcagc acaccagaca ccattgtggt tgttgctggg 1980
aacaagttac gcctggatgt ccctatttct ggagaccctg ctcccactgt ggtctggcag 2040
aagactgtaa cacaggggaa gaaggcctca actgggccac accctgatgc cccagaagat 2100

```
gctggtgctg atgaggagtg ggtgtttgat aagaagctgt tgtgtgagac tgagggccgg   2160
gtccgggtgg agaccaccaa agaccgcagc gtctttacag tcgaaggggc agggaaggaa   2220
gatgaaggtg tctacacagt cacagtaaag aaccccgtgg gcgaggacca ggtcaacctc   2280
acagtcaagg tcatcgatgt cccagatgct cctgcggccc ctaagatcag caacgtgggc   2340
gaggactcct gcactgtgca gtgggaaccg cctgcctatg atggcgggca gccggtcctg   2400
ggatacatcc tggagcgcaa gaagaaaaag agctacaggt ggatgaggct caactttgat   2460
ctgctgcggg agctgagcca cgaggcgagg cgcatgatcg agggtgtagc ctatgagatg   2520
cgagtctacg cagtcaatgc cgtgggaatg tccaggccca gccctgcctc tcagcccttc   2580
atgcctattg ggccccctgg cgaaccaacc cacttggctg tggaggatgt gtcagacacc   2640
actgtctcac tcaagtggcg gcccccagag cgcgtggggg ccggtggcct ggacggatac   2700
agcgtggagt actgccagga gggatgctcc gagtggacac ctgctctgca ggggctgaca   2760
gagcgcacat cgatgctggt gaaggaccta cccactgggg cacggctgct gttccgagta   2820
cgggcacaca atgtggcagg tcctggaggc cctatcgtca ccaaggagcc tgtgacagtg   2880
caggagatac tgcaacgacc acggctccaa ctgcccagac acctgcgcca gaccatccag   2940
aagaaagttg gggagcctgt gaacctcctc atccctttcc agggcaaacc ccggcctcag   3000
gtgacctgga ccaaagaggg gcagcccctg gcaggtgagg aggtgagcat ccggaacagc   3060
cccacagaca cgatcttgtt catccgagct gcccgccgca cccactcggg cacctaccag   3120
gtgacagttc gcattgagaa catggaggac aaggcaacgc tgatcctgca gattgtggac   3180
aagccaagtc ctccccagga tatccggatc gttgagactt ggggtttcaa tgtggctctg   3240
gagtggaagc caccccaaga tgatggcaat acagagatct ggggttatac tgtacagaaa   3300
gctgacaaga agaccatgga gtggttcacg gttttggaac actaccgacg cactcactgt   3360
gtggtatcag agcttatcat tggcaatggc tactacttcc gggtcttcag ccataacatg   3420
gtgggttcca gtgacaaagc tgccgccacc aaggagccag tctttattcc aagaccaggc   3480
atcacatatg agccacccaa atacaaggcc ctggacttct ctgaggcccc aagcttcacc   3540
cagcccttgg caaatcgctc catcattgca ggctataatg ccatcctctg ctgtgctgtc   3600
cgaggtagtc ctaagcccaa gatttcctgg ttcaagaatg gcctggatct gggagaagat   3660
gctcgcttcc gcatgttctg caagcaggga gtattgaccc tggagatcag gaaaccctgc   3720
ccctatgatg gtggtgtcta tgtctgcagg gccaccaact tgcagggcga ggcacagtgt   3780
gagtgccgcc tggaggtgcg agttcctcag tga                                3813
```

<210> SEQ ID NO 14
<211> LENGTH: 1270
<212> TYPE: PRT
<213> ORGANISM: Mus musculus

<400> SEQUENCE: 14

```
Met Pro Glu Pro Gly Lys Lys Pro Val Ser Ala Phe Asn Lys Lys Pro
1               5                   10                  15

Arg Ser Ala Glu Val Thr Ala Gly Ser Ala Ala Val Phe Glu Ala Glu
            20                  25                  30

Thr Glu Arg Ser Gly Val Met Val Arg Trp Gln Arg Asp Gly Ser Asp
        35                  40                  45

Ile Thr Ala Asn Asp Lys Tyr Gly Leu Ala Ala Glu Gly Lys Arg His
    50                  55                  60

Thr Leu Thr Val Arg Asp Ala Ser Pro Asp Asp Gln Gly Ser Tyr Ala
```

-continued

```
65                  70                  75                  80

Val Ile Ala Gly Ser Ser Lys Val Lys Phe Asp Leu Lys Val Thr Glu
                85                  90                  95

Pro Ala Pro Pro Glu Lys Ala Glu Ser Glu Val Ala Pro Gly Ala Pro
            100                 105                 110

Glu Glu Val Pro Ala Pro Ala Thr Glu Leu Glu Glu Ser Val Ser Ser
        115                 120                 125

Pro Glu Gly Ser Val Ser Val Thr Gln Asp Gly Ser Ala Ala Glu His
    130                 135                 140

Gln Gly Ala Pro Asp Asp Pro Ile Gly Leu Phe Leu Met Arg Pro Gln
145                 150                 155                 160

Asp Gly Glu Val Thr Val Gly Gly Ser Ile Val Phe Ser Ala Arg Val
                165                 170                 175

Ala Gly Ala Ser Leu Leu Lys Pro Pro Val Val Lys Trp Phe Lys Gly
            180                 185                 190

Lys Trp Val Asp Leu Ser Ser Lys Val Gly Gln His Leu Gln Leu His
        195                 200                 205

Asp Ser Tyr Asp Arg Ala Ser Lys Val Tyr Leu Phe Glu Leu His Ile
    210                 215                 220

Thr Asp Ala Gln Thr Thr Ser Ala Gly Gly Tyr Arg Cys Glu Val Ser
225                 230                 235                 240

Thr Lys Asp Lys Phe Asp Ser Cys Asn Phe Asn Leu Thr Val His Glu
                245                 250                 255

Ala Ile Gly Ser Gly Asp Leu Asp Leu Arg Ser Ala Phe Arg Arg Thr
            260                 265                 270

Ser Leu Ala Gly Ala Gly Arg Arg Thr Ser Asp Ser His Glu Asp Ala
        275                 280                 285

Gly Thr Pro Asp Phe Ser Ser Leu Leu Lys Lys Arg Asp Ser Phe Arg
    290                 295                 300

Arg Asp Ser Lys Leu Glu Ala Pro Ala Glu Glu Asp Val Trp Glu Ile
305                 310                 315                 320

Leu Arg Gln Ala Pro Pro Ser Glu Tyr Glu Arg Ile Ala Phe Gln His
                325                 330                 335

Gly Val Glu Ala Cys His Arg Pro Leu Lys Arg Leu Lys Gly Met Lys
            340                 345                 350

Gln Asp Glu Lys Lys Ser Thr Ala Phe Gln Lys Lys Leu Glu Pro Ala
        355                 360                 365

Tyr Gln Val Asn Lys Gly His Lys Ile Arg Leu Thr Val Glu Leu Ala
    370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                405                 410                 415

Leu Thr Ile Ser Gln Cys Ser Leu Ala Asp Asp Ala Ala Tyr Gln Cys
            420                 425                 430

Val Val Gly Gly Glu Lys Cys Ser Thr Glu Leu Phe Val Lys Glu Pro
        435                 440                 445

Pro Val Leu Ile Thr Arg Ser Leu Glu Asp Gln Leu Val Met Val Gly
    450                 455                 460

Gln Arg Val Glu Phe Glu Cys Glu Val Ser Glu Glu Gly Ala Gln Val
465                 470                 475                 480

Lys Trp Leu Lys Asp Gly Val Glu Leu Thr Arg Glu Glu Thr Phe Lys
                485                 490                 495
```

-continued

```
Tyr Arg Phe Lys Lys Asp Gly Arg Lys His His Leu Ile Ile Asn Glu
            500                 505                 510

Ala Thr Leu Glu Asp Ala Gly His Tyr Ala Val Arg Thr Ser Gly Gly
        515                 520                 525

Gln Ser Leu Ala Glu Leu Ile Val Gln Glu Lys Lys Leu Glu Val Tyr
    530                 535                 540

Gln Ser Ile Ala Asp Leu Ala Val Gly Ala Lys Asp Gln Ala Val Phe
545                 550                 555                 560

Lys Cys Glu Val Ser Asp Glu Asn Val Arg Gly Val Trp Leu Lys Asn
                565                 570                 575

Gly Lys Glu Leu Val Pro Asp Asn Arg Ile Lys Val Ser His Ile Gly
            580                 585                 590

Arg Val His Lys Leu Thr Ile Asp Asp Val Thr Pro Ala Asp Glu Ala
        595                 600                 605

Asp Tyr Ser Phe Val Pro Glu Gly Phe Ala Cys Asn Leu Ser Ala Lys
    610                 615                 620

Leu His Phe Met Glu Val Lys Ile Asp Phe Val Pro Arg Gln Glu Pro
625                 630                 635                 640

Pro Lys Ile His Leu Asp Cys Pro Gly Ser Thr Pro Asp Thr Ile Val
                645                 650                 655

Val Val Thr Gly Asn Lys Leu Arg Leu Asp Val Pro Ile Ser Gly Asp
            660                 665                 670

Pro Ala Pro Thr Val Val Trp Gln Lys Thr Val Thr Gln Gly Lys Lys
        675                 680                 685

Ala Ser Ala Gly Pro His Pro Asp Ala Pro Glu Asp Ala Gly Ala Asp
    690                 695                 700

Glu Glu Trp Val Phe Asp Lys Lys Leu Leu Cys Glu Thr Glu Gly Arg
705                 710                 715                 720

Val Arg Val Glu Thr Thr Lys Asp Arg Ser Val Phe Thr Val Glu Gly
                725                 730                 735

Ala Glu Lys Glu Asp Glu Gly Val Tyr Thr Val Thr Val Lys Asn Pro
            740                 745                 750

Val Gly Glu Asp Gln Val Asn Leu Thr Val Lys Val Ile Asp Val Pro
        755                 760                 765

Asp Ala Pro Ala Ala Pro Lys Ile Ser Asn Val Gly Glu Asp Ser Cys
    770                 775                 780

Thr Val Gln Trp Glu Pro Pro Ala Tyr Asp Gly Gly Gln Pro Val Leu
785                 790                 795                 800

Gly Tyr Ile Leu Glu Arg Lys Lys Lys Lys Ser Tyr Arg Trp Met Arg
                805                 810                 815

Leu Asn Phe Asp Leu Leu Arg Glu Leu Ser His Glu Ala Arg Arg Met
            820                 825                 830

Ile Glu Gly Val Ala Tyr Glu Met Arg Val Tyr Ala Val Asn Ala Val
        835                 840                 845

Gly Met Ser Arg Pro Ser Pro Ala Ser Gln Pro Phe Met Pro Ile Gly
    850                 855                 860

Pro Pro Gly Glu Pro Thr His Leu Ala Val Glu Asp Val Ser Asp Thr
865                 870                 875                 880

Thr Val Ser Leu Lys Trp Arg Pro Pro Glu Arg Val Gly Ala Gly Gly
                885                 890                 895

Leu Asp Gly Tyr Ser Val Glu Tyr Cys Gln Glu Gly Cys Ser Glu Trp
            900                 905                 910
```

Thr Pro Ala Leu Gln Gly Leu Thr Glu Arg Arg Ser Met Leu Val Lys
915 920 925

Asp Leu Pro Thr Gly Ala Arg Leu Leu Phe Arg Val Arg Ala His Asn
930 935 940

Val Ala Gly Pro Gly Gly Pro Ile Val Thr Lys Glu Pro Val Thr Val
945 950 955 960

Gln Glu Ile Leu Gln Arg Pro Arg Leu Gln Leu Pro Arg His Leu Arg
965 970 975

Gln Thr Ile Gln Lys Lys Val Gly Glu Pro Val Asn Leu Leu Ile Pro
980 985 990

Phe Gln Gly Lys Pro Arg Pro Gln Val Thr Trp Thr Lys Glu Gly Gln
995 1000 1005

Pro Leu Ala Gly Glu Glu Val Ser Ile Arg Asn Ser Pro Thr Asp
1010 1015 1020

Thr Ile Leu Phe Ile Arg Ala Ala Arg Arg Thr His Ser Gly Thr
1025 1030 1035

Tyr Gln Val Thr Val Arg Ile Glu Asn Met Glu Asp Lys Ala Thr
1040 1045 1050

Leu Ile Leu Gln Ile Val Asp Lys Pro Ser Pro Pro Gln Asp Ile
1055 1060 1065

Arg Ile Val Glu Thr Trp Gly Phe Asn Val Ala Leu Glu Trp Lys
1070 1075 1080

Pro Pro Gln Asp Asp Gly Asn Thr Glu Ile Trp Gly Tyr Thr Val
1085 1090 1095

Gln Lys Ala Asp Lys Lys Thr Met Glu Trp Phe Thr Val Leu Glu
1100 1105 1110

His Tyr Arg Arg Thr His Cys Val Val Ser Glu Leu Ile Ile Gly
1115 1120 1125

Asn Gly Tyr Tyr Phe Arg Val Phe Ser His Asn Met Val Gly Ser
1130 1135 1140

Ser Asp Lys Ala Ala Ala Thr Lys Glu Pro Val Phe Ile Pro Arg
1145 1150 1155

Pro Gly Ile Thr Tyr Glu Pro Pro Lys Tyr Lys Ala Leu Asp Phe
1160 1165 1170

Ser Glu Ala Pro Ser Phe Thr Gln Pro Leu Ala Asn Arg Ser Ile
1175 1180 1185

Ile Ala Gly Tyr Asn Ala Ile Leu Cys Cys Ala Val Arg Gly Ser
1190 1195 1200

Pro Lys Pro Lys Ile Ser Trp Phe Lys Asn Gly Leu Asp Leu Gly
1205 1210 1215

Glu Asp Ala Arg Phe Arg Met Phe Cys Lys Gln Gly Val Leu Thr
1220 1225 1230

Leu Glu Ile Arg Lys Pro Cys Pro Tyr Asp Gly Gly Val Tyr Val
1235 1240 1245

Cys Arg Ala Thr Asn Leu Gln Gly Glu Ala Gln Cys Glu Cys Arg
1250 1255 1260

Leu Glu Val Arg Val Pro Gln
1265 1270

<210> SEQ ID NO 15
<211> LENGTH: 2889
<212> TYPE: DNA
<213> ORGANISM: Mus musculus

<400> SEQUENCE: 15

-continued

```
atgccggagc cgggtaaaaa gccggttagc gcgttcaaca aaaaaccgcg tagcgcggaa     60
gtgaccgcgg gtagcgcggc ggtgtttgag gcggaaaccg agcgtagcgg cgttaaagtg    120
cgttggcaac gtgacggtag cgatattacc gcgaacgata aatacggtct ggcggcggaa    180
ggcaagcgtc acaccctgac cgttcgtgat gcgagcccgg acgatcaggg tagctatgcg    240
gtgatcgcgg gcagcagcaa ggtgaaattt gacctgaaag ttaccgagcc ggctccgccg    300
gaaaaagcgg aaagcgaggt ggcgccgggt gcgccgaagg aagttccggc gccggcgacc    360
gagctggagg aaagcgtgag cagcccggaa ggcagcgtta gcgtgaccca ggatggtagc    420
gcggcggaac atcaaggtgc gccggatgat ccgatcggtc tgttcctgat gcgtccgcaa    480
gacggtgagg ttaccgtggg tggcagcatt gtgtttagcg cgcgtgttgc gggtgcgagc    540
ctgctgaaac cgccggtggt taagtggttc aagggcaaat gggtggatct gagcagcaaa    600
gttggtcagc acctgcaact gcacgacagc tacgatcgtg cgagcaaggt ttacctgttc    660
gaactgcaca ttaccgatgc gcagaccacc agcgcgggtg gctaccgttg cgaggttagc    720
accaaggaca aattcgatag ctgcaacttt aacctgaccg tgcacgaagc gatcggtagc    780
ggcgacctgg atctgcgtag cgcgtttcgt cgtaccagcc tggcgggtgc gggtcgtcgt    840
accagcgaca gccatgagga tgcgggcacc ctggatttca gcagcctgct gaagaaacgt    900
gatagctttc gtcgtgacag caaactggaa gcgccggcgg aggaagacgt ttgggagatc    960
ctgcgtcaag ctccgccgag cgaatacgag cgtattgcgt tccagcacgg tgtgaccgat   1020
ctgcgtggca tgctgaagcg tctgaagggt atgaagcagg acgaaaagaa aagcaccgcg   1080
tttcagaaga aactggagcc ggcgtatcaa gtgaacaaag gccacaagat ccgtctgacc   1140
gtggaactgg cggacccgga tgcggaagtg aaatggctga agaacggcca ggaaatccaa   1200
atgagcggta gcaaatacat tttcgagagc gttggtgcga agcgtaccct gaccattagc   1260
caatgcagcc tggcggacga tgcggcgtat cagtgcgtgg ttggtggcga gaaatgcagc   1320
accgaactgt tcgtgaagga gccgccggtt ctgatcaccc gtagcctgga agatcagctg   1380
gttatggtgg gtcaacgtgt ggaatttgag tgcgaagtta gcgaggaagg cgcgcaagtg   1440
aaatggctga aggacggtgt tgagctgacc cgtgaggaaa ccttcaaata ccgttttaag   1500
aaagatggtc gtaagcacca cctgatcatt aacgaagcga ccctggagga tgcgggtcac   1560
tatgcggttc gtaccagcgg tggccagagc ctggcggaac tgatcgtgca agaaaagaaa   1620
ctggaagtgt atcagagcat tgcggatctg gcggtgggtg cgaaagacca ggcggtgttc   1680
aagtgcgaag ttagcgatga gaacgttcgt ggtgtgtggc tgaaaaacgg caaggagctg   1740
gttccggaca accgtatcaa agtgagccac attggtcgtg ttcacaagct gaccatcgac   1800
gatgttaccc cggcggacga agcggattat agcttcgtgc cggagggctt tgcgtgcaac   1860
ctgagcgcga aactgcactt catggaagtg aagatcgact ttgttccgcg tcaggagccg   1920
ccgaaaattc atctggattg cccgggtagc accccggaca ccattgtggt tgtggcgggt   1980
aacaaactgc gtctggatgt gccgattagc ggcgacccgg cgccgaccgt tgtgtggcag   2040
aagaccgtga cccaaggtaa gaaagcgagc accggtccgc acccggatgc gccggaggat   2100
gcgggtgcgg acgaggaatg ggttttcgat aagaaactgc tgtgcgaaac cgaaggccgt   2160
gttcgtgtgg aaaccaccaa ggatcgtagc gtttttaccg tggagggcgc ggagaaagaa   2220
gacgagggtg tttacaccgt taccgtgaag aacccggtgg gtgaagacca ggttaacctg   2280
accgttaaag ttattgatgt tccggatgcg ccggcggcgc cgaagattag caacgtgggt   2340
```

-continued

```
gaagatagct gcaccgttca atgggagccg ccggcgtatg atggtggcca gccggtgctg   2400

ggctatatcc tggagcgtaa gaaaaagaaa agctatcgtt ggatgcgtct gaacttcgac   2460

ctgctgcgtg aactgagcca cgaggcgcgt cgtatgattg aaggtgttgc gtacgagatg   2520

cgtgtttatg cggtgaacgc ggttggtatg agccgtccga gcccggcgag ccagccgttt   2580

atgccgattg gtccgccggg tgaaccgacc cacctggcgg tggaggacgt tagcgatacc   2640

accgtgagcc tgaaatggcg tccgccggaa cgtgttggtg cgggtggcct ggatggctac   2700

agcgtggaat attgccaaga gggctgcagc gaatggaccc cggcgctgca gggtctgacc   2760

gagcgtacca gcatgctggt taaagacctg ccgaccggtg cgcgtctgct gttccgtgtg   2820

cgtgcgcata acgttgcggg tccgggtggc ccgatcgtga ccaaggaacc ggttaccgtg   2880

caggagatt                                                           2889


<210> SEQ ID NO 16
<211> LENGTH: 963
<212> TYPE: PRT
<213> ORGANISM: Mus musculus

<400> SEQUENCE: 16

Met Pro Glu Pro Gly Lys Lys Pro Val Ser Ala Phe Asn Lys Lys Pro
1               5                   10                  15

Arg Ser Ala Glu Val Thr Ala Gly Ser Ala Ala Val Phe Glu Ala Glu
            20                  25                  30

Thr Glu Arg Ser Gly Val Lys Val Arg Trp Gln Arg Asp Gly Ser Asp
        35                  40                  45

Ile Thr Ala Asn Asp Lys Tyr Gly Leu Ala Ala Glu Gly Lys Arg His
    50                  55                  60

Thr Leu Thr Val Arg Asp Ala Ser Pro Asp Asp Gln Gly Ser Tyr Ala
65                  70                  75                  80

Val Ile Ala Gly Ser Ser Lys Val Lys Phe Asp Leu Lys Val Thr Glu
                85                  90                  95

Pro Ala Pro Pro Glu Lys Ala Glu Ser Glu Val Ala Pro Gly Ala Pro
            100                 105                 110

Lys Glu Val Pro Ala Pro Ala Thr Glu Leu Glu Glu Ser Val Ser Ser
        115                 120                 125

Pro Glu Gly Ser Val Ser Val Thr Gln Asp Gly Ser Ala Ala Glu His
    130                 135                 140

Gln Gly Ala Pro Asp Asp Pro Ile Gly Leu Phe Leu Met Arg Pro Gln
145                 150                 155                 160

Asp Gly Glu Val Thr Val Gly Gly Ser Ile Val Phe Ser Ala Arg Val
                165                 170                 175

Ala Gly Ala Ser Leu Leu Lys Pro Pro Val Val Lys Trp Phe Lys Gly
            180                 185                 190

Lys Trp Val Asp Leu Ser Ser Lys Val Gly Gln His Leu Gln Leu His
        195                 200                 205

Asp Ser Tyr Asp Arg Ala Ser Lys Val Tyr Leu Phe Glu Leu His Ile
    210                 215                 220

Thr Asp Ala Gln Thr Thr Ser Ala Gly Gly Tyr Arg Cys Glu Val Ser
225                 230                 235                 240

Thr Lys Asp Lys Phe Asp Ser Cys Asn Phe Asn Leu Thr Val His Glu
                245                 250                 255

Ala Ile Gly Ser Gly Asp Leu Asp Leu Arg Ser Ala Phe Arg Arg Thr
            260                 265                 270
```

-continued

```
Ser Leu Ala Gly Ala Gly Arg Arg Thr Ser Asp Ser His Glu Asp Ala
        275                 280                 285

Gly Thr Leu Asp Phe Ser Ser Leu Leu Lys Lys Arg Asp Ser Phe Arg
    290                 295                 300

Arg Asp Ser Lys Leu Glu Ala Pro Ala Glu Glu Asp Val Trp Glu Ile
305                 310                 315                 320

Leu Arg Gln Ala Pro Pro Ser Glu Tyr Glu Arg Ile Ala Phe Gln His
                325                 330                 335

Gly Val Thr Asp Leu Arg Gly Met Leu Lys Arg Leu Lys Gly Met Lys
            340                 345                 350

Gln Asp Glu Lys Lys Ser Thr Ala Phe Gln Lys Lys Leu Glu Pro Ala
        355                 360                 365

Tyr Gln Val Asn Lys Gly His Lys Ile Arg Leu Thr Val Glu Leu Ala
    370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                405                 410                 415

Leu Thr Ile Ser Gln Cys Ser Leu Ala Asp Asp Ala Ala Tyr Gln Cys
            420                 425                 430

Val Val Gly Gly Glu Lys Cys Ser Thr Glu Leu Phe Val Lys Glu Pro
        435                 440                 445

Pro Val Leu Ile Thr Arg Ser Leu Glu Asp Gln Leu Val Met Val Gly
    450                 455                 460

Gln Arg Val Glu Phe Glu Cys Glu Val Ser Glu Glu Gly Ala Gln Val
465                 470                 475                 480

Lys Trp Leu Lys Asp Gly Val Glu Leu Thr Arg Glu Glu Thr Phe Lys
                485                 490                 495

Tyr Arg Phe Lys Lys Asp Gly Arg Lys His His Leu Ile Ile Asn Glu
            500                 505                 510

Ala Thr Leu Glu Asp Ala Gly His Tyr Ala Val Arg Thr Ser Gly Gly
        515                 520                 525

Gln Ser Leu Ala Glu Leu Ile Val Gln Glu Lys Lys Leu Glu Val Tyr
    530                 535                 540

Gln Ser Ile Ala Asp Leu Ala Val Gly Ala Lys Asp Gln Ala Val Phe
545                 550                 555                 560

Lys Cys Glu Val Ser Asp Glu Asn Val Arg Gly Val Trp Leu Lys Asn
                565                 570                 575

Gly Lys Glu Leu Val Pro Asp Asn Arg Ile Lys Val Ser His Ile Gly
            580                 585                 590

Arg Val His Lys Leu Thr Ile Asp Asp Val Thr Pro Ala Asp Glu Ala
        595                 600                 605

Asp Tyr Ser Phe Val Pro Glu Gly Phe Ala Cys Asn Leu Ser Ala Lys
    610                 615                 620

Leu His Phe Met Glu Val Lys Ile Asp Phe Val Pro Arg Gln Glu Pro
625                 630                 635                 640

Pro Lys Ile His Leu Asp Cys Pro Gly Ser Thr Pro Asp Thr Ile Val
                645                 650                 655

Val Val Ala Gly Asn Lys Leu Arg Leu Asp Val Pro Ile Ser Gly Asp
            660                 665                 670

Pro Ala Pro Thr Val Val Trp Gln Lys Thr Val Thr Gln Gly Lys Lys
        675                 680                 685

Ala Ser Thr Gly Pro His Pro Asp Ala Pro Glu Asp Ala Gly Ala Asp
```

690 695 700

Glu Glu Trp Val Phe Asp Lys Lys Leu Leu Cys Glu Thr Glu Gly Arg
705 710 715 720

Val Arg Val Glu Thr Thr Lys Asp Arg Ser Val Phe Thr Val Glu Gly
725 730 735

Ala Glu Lys Glu Asp Glu Gly Val Tyr Thr Val Thr Val Lys Asn Pro
740 745 750

Val Gly Glu Asp Gln Val Asn Leu Thr Val Lys Val Ile Asp Val Pro
755 760 765

Asp Ala Pro Ala Ala Pro Lys Ile Ser Asn Val Gly Glu Asp Ser Cys
770 775 780

Thr Val Gln Trp Glu Pro Pro Ala Tyr Asp Gly Gly Gln Pro Val Leu
785 790 795 800

Gly Tyr Ile Leu Glu Arg Lys Lys Lys Lys Ser Tyr Arg Trp Met Arg
805 810 815

Leu Asn Phe Asp Leu Leu Arg Glu Leu Ser His Glu Ala Arg Arg Met
820 825 830

Ile Glu Gly Val Ala Tyr Glu Met Arg Val Tyr Ala Val Asn Ala Val
835 840 845

Gly Met Ser Arg Pro Ser Pro Ala Ser Gln Pro Phe Met Pro Ile Gly
850 855 860

Pro Pro Gly Glu Pro Thr His Leu Ala Val Glu Asp Val Ser Asp Thr
865 870 875 880

Thr Val Ser Leu Lys Trp Arg Pro Pro Glu Arg Val Gly Ala Gly Gly
885 890 895

Leu Asp Gly Tyr Ser Val Glu Tyr Cys Gln Glu Gly Cys Ser Glu Trp
900 905 910

Thr Pro Ala Leu Gln Gly Leu Thr Glu Arg Thr Ser Met Leu Val Lys
915 920 925

Asp Leu Pro Thr Gly Ala Arg Leu Leu Phe Arg Val Arg Ala His Asn
930 935 940

Val Ala Gly Pro Gly Gly Pro Ile Val Thr Lys Glu Pro Val Thr Val
945 950 955 960

Gln Glu Ile

<210> SEQ ID NO 17
<211> LENGTH: 3411
<212> TYPE: DNA
<213> ORGANISM: Mus musculus

<400> SEQUENCE: 17
atgcctgagg ctaaaccagc ggccaaaaag gcctccaaag gcaaagatgc cccaaaggaa 60
gcccctgcaa agcagactcc tgaagagccc cccaaagagg ccccacctga ggaccaatcc 120
ccaactgcgg aggagcccac aggcatcttc ctgaaaaagc cggactctgt gtcagtggag 180
actgggaaag acgcggtgat tctggccaag gtgaacggga aggagctccc aggcaagccg 240
accatcaagt ggttcaaggg gaagtggcag gagctgggca gcaagagcgg agcccggttc 300
atcttcaagg aatctcatga ctctaccagc aatgtgtaca ccgtggagct ccacattggg 360
aaggtggtcc taggggaccg cggggattac cgtctagaga tcaaagccaa ggatgtctgc 420
gacagctgct cgttcaacgt ggatgtggag gcaccccgtc aggactcatc cggtcagagc 480
ctcgagagct tcaagcgttc gggtgacggg aagtcagaag atgcaggcga gctggatttc 540
agtggcttgc tgaagaagag ggaagtagtt gaggaggaga agaagaagaa gaaagatgat 600

-continued

```
gatgatctgg gtatacctcc ggagatttgg gagctcctga aaggggccaa gaagagcgag    660
tacgagaaga tcgccttcca gtacggcatc actgacctcc gtggcatgct gaagcggctc    720
aagaaggcca aggtggaggt caagaagagt gcagccttca ctaagaagtt ggacccagcc    780
taccaagtag acaggggcaa caagatcaag ttggtggtgg agatcagtga cccagacctt    840
cctctcaagt ggttcaagaa tggccaggag atcaaaccaa gcagcaagta tgtgtttgag    900
aacgttggga agaaacgaat tcttaccatc aacaagtgca cgctggcgga tgatgctgca    960
tatgaggtgg cagtccaaga tgagaagtgt ttcactgaac tctttgtcaa agagcccccca  1020
gtcttgattg tcaccccact ggaggaccag caggtattcg taggtgaccg agtggaaatg   1080
tcggtagagg tgtcagaaga gggtgcacag gttatgtgga tgaaagatgg tgtggagatg   1140
actcgggagg attcctacaa ggcgcgctac cgcttcaaga aggacgggaa acggcacatc   1200
ctcatctact ctgatgtggc ccaggaggat gggggccgct accaggtcat aaccaatggt   1260
ggccagtgtg aggctgaact cattgtggaa gagaagcaac tggaggtcct gcaggacatt   1320
gctgacctga cagtgaaggc tgcagagcag gctgtgttca agtgtgaagt gtctgatgag   1380
aaggtgacag gcaaatggta caagaatggc gtggaggtac gacccagcaa gaggatcacc   1440
atctcccatg tgggcagatt ccacaagctg gtgattgatg acgtccgccc tgaggatgag   1500
ggagactaca cattcgtgcc cgatggctat gccctatccc tctcagccaa gctcaacttt   1560
ttggaaatca aagtggagta cgtacctaag caagagcccc cgaagatcca cctggactgc   1620
tcagggaaga cctcagataa ctcaattgtt gtggtggctg gaaacaagct gcggctggat   1680
gtggccatca caggggaacc acctcccact gctacctggc taaggggaga tgaggtgttc   1740
acagccacag aaggcaggac acacatcgag cagaggccag actgcagcag ctttgtgatc   1800
gagagtgcgg agcggtcgga tgagggccgc tacaccatca aagtcaccaa tcctgcgggc   1860
gaggacgtgg cctccatttt cctgcgggtt gtggatgttc ctgatcctcc agaggctgtc   1920
cgtgtcacct cagttggaga agactgggcc attctggtct gggagccacc caagtatgat   1980
ggaggacagc cagtgactgg gtacttgatg gagcggaaga agaaaggctc ccagcgctgg   2040
atgaagatca actttgaggt cttcactgac accacctacg agtccacaaa gatgatcgag   2100
ggcgtccttt atgagatgcg ggtcttcgct gtcaacgcca ttggggtctc acagcccagc   2160
atgaacacca agcccttcat gcccattgct cccacgagtg caccacaaca cctcaccgtg   2220
gaggatgtga cggacaccac caccacactt aagtggagac ctccagatcg gattggtgct   2280
ggtggcattg atggctacct ggtggagtac tgcctggagg gctctgagga atgggtaccg   2340
gctaacaagg agccagtgga acgctgtggc ttcactgtca aggatctccc aactggagcc   2400
aggatcctct tccgggttgt tggggtcaac atcgcagggc gcagtgaacc agccaccctc   2460
cttcagccag tcactatcag ggagattgtt gagcaaccta agatccgcct tccccgccat   2520
cttcgtcaga cttatatccg aaaagttggg gaggccctca acctcgtcat ccccttccag   2580
ggcaagcccc ggcctcaggt ggtgtggacc aagggtgggg ctcccttgga tacctcccgt   2640
gtgaatgtgc ggactagtga cttcgacaca gtgttcttcg tgcgacaggc ggcccgctct   2700
gactccggag agtatgagct gagtgtgcag attgaaaaca tgaaggacac tgctaccata   2760
cgcatccggg tcgtggaaaa ggcagggcca gcagagaatg tgatggtgaa ggaggtgtgg   2820
ggcacaaatg ctctggtgga gtggcagccg cccaaggacg acgggaacag tgagatcaca   2880
ggctactttg tccagaaggc tgacaaaaag accatggagt ggttcaatgt ctacgaacac   2940
```

-continued

```
aatcgccaca ccagctgtac ggtgtctgac ctcattgtgg gtaatgagta ctacttccgt   3000

atcttcagcg agaacatctg cggtctcagt gactcgccag gtgtctccaa gaacacagct   3060

cgaattctca agacaggaat caccttaaaa ccactggagt acaaggagca tgatttccgg   3120

acggctccca agttcctgac cccgctgatg gaccgggtcg tggtggcggg atataccgca   3180

gctctcaact gtgccgtcag aggccaccct aagccaaagg tggtgtggat gaagaacaag   3240

atggaaatcc atgaagatcc caaattcctc ataaccaact accagggcat cctgacactg   3300

aacatccgcc gaccgtcacc ctttgatgca gggacctatt cctgccgcgc cttcaatgag   3360

ctgggggagg ccctggctga atgcaaactg gatgtccgag tgccacagtg a            3411


<210> SEQ ID NO 18
<211> LENGTH: 1136
<212> TYPE: PRT
<213> ORGANISM: Mus musculus

<400> SEQUENCE: 18

Met Pro Glu Ala Lys Pro Ala Ala Lys Lys Ala Ser Lys Gly Lys Asp
1               5                   10                  15

Ala Pro Lys Glu Ala Pro Ala Lys Gln Thr Pro Glu Glu Pro Pro Lys
            20                  25                  30

Glu Ala Pro Pro Glu Asp Gln Ser Pro Thr Ala Glu Glu Pro Thr Gly
        35                  40                  45

Ile Phe Leu Lys Lys Pro Asp Ser Val Ser Val Glu Thr Gly Lys Asp
    50                  55                  60

Ala Val Ile Leu Ala Lys Val Asn Gly Lys Glu Leu Pro Gly Lys Pro
65                  70                  75                  80

Thr Ile Lys Trp Phe Lys Gly Lys Trp Gln Glu Leu Gly Ser Lys Ser
                85                  90                  95

Gly Ala Arg Phe Ile Phe Lys Glu Ser His Asp Ser Thr Ser Asn Val
            100                 105                 110

Tyr Thr Val Glu Leu His Ile Gly Lys Val Val Leu Gly Asp Arg Gly
        115                 120                 125

Asp Tyr Arg Leu Glu Ile Lys Ala Lys Asp Val Cys Asp Ser Cys Ser
    130                 135                 140

Phe Asn Val Asp Val Glu Ala Pro Arg Gln Asp Ser Ser Gly Gln Ser
145                 150                 155                 160

Leu Glu Ser Phe Lys Arg Ser Gly Asp Gly Lys Ser Glu Asp Ala Gly
                165                 170                 175

Glu Leu Asp Phe Ser Gly Leu Leu Lys Lys Arg Glu Val Val Glu Glu
            180                 185                 190

Glu Lys Lys Lys Lys Lys Asp Asp Asp Asp Leu Gly Ile Pro Pro Glu
        195                 200                 205

Ile Trp Glu Leu Leu Lys Gly Ala Lys Lys Ser Glu Tyr Glu Lys Ile
    210                 215                 220

Ala Phe Gln Tyr Gly Ile Thr Asp Leu Arg Gly Met Leu Lys Arg Leu
225                 230                 235                 240

Lys Lys Ala Lys Val Glu Val Lys Lys Ser Ala Ala Phe Thr Lys Lys
                245                 250                 255

Leu Asp Pro Ala Tyr Gln Val Asp Arg Gly Asn Lys Ile Lys Leu Val
            260                 265                 270

Val Glu Ile Ser Asp Pro Asp Leu Pro Leu Lys Trp Phe Lys Asn Gly
        275                 280                 285

Gln Glu Ile Lys Pro Ser Ser Lys Tyr Val Phe Glu Asn Val Gly Lys
```

```
    290                 295                 300

Lys Arg Ile Leu Thr Ile Asn Lys Cys Thr Leu Ala Asp Asp Ala Ala
305                 310                 315                 320

Tyr Glu Val Ala Val Gln Asp Glu Lys Cys Phe Thr Glu Leu Phe Val
                325                 330                 335

Lys Glu Pro Pro Val Leu Ile Val Thr Pro Leu Glu Asp Gln Gln Val
            340                 345                 350

Phe Val Gly Asp Arg Val Glu Met Ser Val Glu Val Ser Glu Glu Gly
        355                 360                 365

Ala Gln Val Met Trp Met Lys Asp Gly Val Glu Met Thr Arg Glu Asp
    370                 375                 380

Ser Tyr Lys Ala Arg Tyr Arg Phe Lys Lys Asp Gly Lys Arg His Ile
385                 390                 395                 400

Leu Ile Tyr Ser Asp Val Ala Gln Glu Asp Gly Gly Arg Tyr Gln Val
                405                 410                 415

Ile Thr Asn Gly Gly Gln Cys Glu Ala Glu Leu Ile Val Glu Glu Lys
            420                 425                 430

Gln Leu Glu Val Leu Gln Asp Ile Ala Asp Leu Thr Val Lys Ala Ala
        435                 440                 445

Glu Gln Ala Val Phe Lys Cys Glu Val Ser Asp Glu Lys Val Thr Gly
    450                 455                 460

Lys Trp Tyr Lys Asn Gly Val Glu Val Arg Pro Ser Lys Arg Ile Thr
465                 470                 475                 480

Ile Ser His Val Gly Arg Phe His Lys Leu Val Ile Asp Asp Val Arg
                485                 490                 495

Pro Glu Asp Glu Gly Asp Tyr Thr Phe Val Pro Asp Gly Tyr Ala Leu
            500                 505                 510

Ser Leu Ser Ala Lys Leu Asn Phe Leu Glu Ile Lys Val Glu Tyr Val
        515                 520                 525

Pro Lys Gln Glu Pro Pro Lys Ile His Leu Asp Cys Ser Gly Lys Thr
    530                 535                 540

Ser Asp Asn Ser Ile Val Val Val Ala Gly Asn Lys Leu Arg Leu Asp
545                 550                 555                 560

Val Ala Ile Thr Gly Glu Pro Pro Pro Thr Ala Thr Trp Leu Arg Gly
                565                 570                 575

Asp Glu Val Phe Thr Ala Thr Glu Gly Arg Thr His Ile Glu Gln Arg
            580                 585                 590

Pro Asp Cys Ser Ser Phe Val Ile Glu Ser Ala Glu Arg Ser Asp Glu
        595                 600                 605

Gly Arg Tyr Thr Ile Lys Val Thr Asn Pro Ala Gly Glu Asp Val Ala
    610                 615                 620

Ser Ile Phe Leu Arg Val Val Asp Val Pro Asp Pro Pro Glu Ala Val
625                 630                 635                 640

Arg Val Thr Ser Val Gly Glu Asp Trp Ala Ile Leu Val Trp Glu Pro
                645                 650                 655

Pro Lys Tyr Asp Gly Gly Gln Pro Val Thr Gly Tyr Leu Met Glu Arg
            660                 665                 670

Lys Lys Lys Gly Ser Gln Arg Trp Met Lys Ile Asn Phe Glu Val Phe
        675                 680                 685

Thr Asp Thr Thr Tyr Glu Ser Thr Lys Met Ile Glu Gly Val Leu Tyr
    690                 695                 700

Glu Met Arg Val Phe Ala Val Asn Ala Ile Gly Val Ser Gln Pro Ser
705                 710                 715                 720
```

-continued

```
Met Asn Thr Lys Pro Phe Met Pro Ile Ala Pro Thr Ser Ala Pro Gln
                725                 730                 735

His Leu Thr Val Glu Asp Val Thr Asp Thr Thr Thr Thr Leu Lys Trp
            740                 745                 750

Arg Pro Pro Asp Arg Ile Gly Ala Gly Gly Ile Asp Gly Tyr Leu Val
        755                 760                 765

Glu Tyr Cys Leu Glu Gly Ser Glu Glu Trp Val Pro Ala Asn Lys Glu
    770                 775                 780

Pro Val Glu Arg Cys Gly Phe Thr Val Lys Asp Leu Pro Thr Gly Ala
785                 790                 795                 800

Arg Ile Leu Phe Arg Val Val Gly Val Asn Ile Ala Gly Arg Ser Glu
                805                 810                 815

Pro Ala Thr Leu Leu Gln Pro Val Thr Ile Arg Glu Ile Val Glu Gln
            820                 825                 830

Pro Lys Ile Arg Leu Pro Arg His Leu Arg Gln Thr Tyr Ile Arg Lys
        835                 840                 845

Val Gly Glu Ala Leu Asn Leu Val Ile Pro Phe Gln Gly Lys Pro Arg
    850                 855                 860

Pro Gln Val Val Trp Thr Lys Gly Gly Ala Pro Leu Asp Thr Ser Arg
865                 870                 875                 880

Val Asn Val Arg Thr Ser Asp Phe Asp Thr Val Phe Phe Val Arg Gln
                885                 890                 895

Ala Ala Arg Ser Asp Ser Gly Glu Tyr Glu Leu Ser Val Gln Ile Glu
            900                 905                 910

Asn Met Lys Asp Thr Ala Thr Ile Arg Ile Arg Val Val Glu Lys Ala
        915                 920                 925

Gly Pro Ala Glu Asn Val Met Val Lys Glu Val Trp Gly Thr Asn Ala
    930                 935                 940

Leu Val Glu Trp Gln Pro Pro Lys Asp Asp Gly Asn Ser Glu Ile Thr
945                 950                 955                 960

Gly Tyr Phe Val Gln Lys Ala Asp Lys Lys Thr Met Glu Trp Phe Asn
                965                 970                 975

Val Tyr Glu His Asn Arg His Thr Ser Cys Thr Val Ser Asp Leu Ile
            980                 985                 990

Val Gly Asn Glu Tyr Tyr Phe Arg  Ile Phe Ser Glu Asn  Ile Cys Gly
        995                 1000                1005

Leu Ser  Asp Ser Pro Gly Val  Ser Lys Asn Thr Ala  Arg Ile Leu
    1010                1015                1020

Lys Thr  Gly Ile Thr Leu Lys  Pro Leu Glu Tyr Lys  Glu His Asp
    1025                1030                1035

Phe Arg  Thr Ala Pro Lys Phe  Leu Thr Pro Leu Met  Asp Arg Val
    1040                1045                1050

Val Val  Ala Gly Tyr Thr Ala  Ala Leu Asn Cys Ala  Val Arg Gly
    1055                1060                1065

His Pro  Lys Pro Lys Val Val  Trp Met Lys Asn Lys  Met Glu Ile
    1070                1075                1080

His Glu  Asp Pro Lys Phe Leu  Ile Thr Asn Tyr Gln  Gly Ile Leu
    1085                1090                1095

Thr Leu  Asn Ile Arg Arg Pro  Ser Pro Phe Asp Ala  Gly Thr Tyr
    1100                1105                1110

Ser Cys  Arg Ala Phe Asn Glu  Leu Gly Glu Ala Leu  Ala Glu Cys
    1115                1120                1125
```

-continued

```
Lys Leu  Asp Val Arg Val Pro  Gln
    1130                 1135


<210> SEQ ID NO 19
<211> LENGTH: 3550
<212> TYPE: DNA
<213> ORGANISM: Mus musculus

<400> SEQUENCE: 19

atgccagaac ccactaagaa agaggaaaat gaagtgtccg ccccagcccc tcccccggaa     60

gaatggtctc ttggtgagtc acctgctggc ggggaagagc aggacaaaca gaatgccaac    120

tcccagctgt ccaccctgtt tgttgaaaaa cctcaaaccg gatcggtgaa agttggtgca    180

aacatcacct ttgtagccaa agttagggct gaagatcttc ttagaaaacc cactgtcaaa    240

tggttcaagg ggaaatggat ggatctggcc agcaaagccg ggaaacacct gcagctgaag    300

gagaccttcg agaggcaaac tcgggtatac acattcgaga tgcagatcat caaagccaaa    360

gagaactacg cagggaatta taggtgtgag gtcacctaca aggataaatt tgacagctgt    420

tcgtttgatc ttgaagtcca tgagtctact gggactactc caaacattga catcagatct    480

gccttcaaaa gaagtggaga aggtcaagag gatgcagggg aacttgactt tagtggtctc    540

ctgaaacgta gggaggtgaa gcagcaggaa gaggagcctg agatagacgt gtgggagctg    600

ctgaaaaatg ccaaccccaa cgaatacgag aagatcgctt tccagtatgg catcaccgac    660

ttgcgtggca tgcttaagcg gctcaagcgc atgcgcaggg tggaaaagaa gagcgcagct    720

tttgcaaaaa ttctcgatcc tgcatatcag gtggataaag gaggcaaagt gagatttgtc    780

gtggagttgg cagacccaaa actggaggtg aaatggttta aaaatggcca agagattcga    840

cccagcacaa aatacatctt tgagcacaaa ggaaacgaga gaatcatgtt tattaataac    900

tgttcgctga cagatgattc ggagtactat gtgacagctg gagatgagaa atgttctact    960

gagctctttg taagagagcc tccaatcatg gtgactaagc agctggaaga catgaacgct   1020

tactgtgggg agagggtaga gatggaagtt gaggtgtctg aagatgacgc caatgtaaaa   1080

tggtttaaga atggtgaaga gatcttccct ggtccaaagt caagatacaa gattaaagtt   1140

gaaggcaaaa agcacacgtt gatcatagaa ggggcaacaa aggctgacag tgcggagtac   1200

tcagccatga caaccggggg acaatcatct gccaaactca gcgttgactt gagacctcta   1260

aagatcacga cgcctctgac ggaccagaca gtaaaacttg ggaaagaagt atgcttgaag   1320

tgtgaaatct ctgaaaatgt accaggaaaa tggacaaaaa atggcctccc tgttcaggag   1380

ggtgagcgtc tgaaggttgt tcacaaggga agaatccaca agttagtcat agccaatgct   1440

ctcattgaag atgaaggtga atatgtattt acaccagatg cctacaatgt tcctttgtct   1500

gccaaagttc atgtcatcga ccctcccaag atcatcctgg atggcctgga tgctgataac   1560

acagtgacag tgatagctgg aagcaagctt cgcctggaga ttcctgtcac aggggaacca   1620

cctcccaaag ccatctggag ccgagcagat aaggctatta tggaaggcag tggtcggatc   1680

agggcagaat cctaccctga cagcagcaca ctggtcattg acgtggcaga gagagacgac   1740

tctggtgtgt acaacataaa tctgaaaaat gaggctggag aagcacatgc aagcatcaag   1800

attaaggttg tggatatccc tgatcctcca gtggcaccaa atgtgacaga agtgggagat   1860

gactggtgca tcatgaactg ggagcctcct gcctatgatg gagggtctcc aatcttagga   1920

tactttattg agaggaaaaa gaaacaaagc tccaggtgga tgagactgaa tttcgatctc   1980

tgcaaagaga caacttttga gcccaagaag atgattgaag gcgtggccta cgaggtccga   2040
```

```
atctttgcgg tcaacgccat tggcatctcc aagcccagta tgccctccaa gccctttgtt   2100

cctttggctg tgaccagccc tcctactctt ctggctgtcg actccgtgac tgactcgtct   2160

gtgacgatga agtggaggcc cccagatcag attggcgcag caggtttaga tggctatgtg   2220

ctagagtatt gctttgaagg aactgaggac tggatagttg caaacacaga cctgatcgac   2280

aagaccaagt tcaccatcaa tggtctgccc acggatgcga agatctttgt acgtgtgaag   2340

gctattaacg cggctggggc tagtgagccc aagtactatt ctcagcccat ccttgtgaag   2400

gaaatcattg agccaccaaa gattcgcatc ccaaggcatc tgaagcaaac ttacatccgc   2460

agagtcggag aagctgtcaa tctggtgatt cctttttcagg gtaaaccaag accagagttg   2520

acctggaaga aggacggtga agaaattgac aagaatcaaa taaacattcg caactcagaa   2580

actgatacca tcatattcat ccggaaagca gagcggagcc actcgggcaa gtacgacctg   2640

caggtcaaag tggataaata cgtggaaaat gcctctatcg acatccagat tgttgaccgt   2700

ccaggtccac cccagactgt gactattgaa gatgtgtggg gagagaatgt tgccctaaca   2760

tggacaccac caaaggacga tgggaatgct gccatcacag ggtacaccat ccagaaggcc   2820

gacaagaaaa gcatggaatg gttcaccgtc attgaacatt accaccgaac caacgccacc   2880

attactgagc tggtcatagg gaacgagtat tacttccggg tctttgctga aaacatgtgc   2940

ggccttagcg aggatgcaac tatgacgaag gagagtgcag tgattgccaa ggacggtaag   3000

atctataaaa atccagtgta cgaagacttc aatttcacag aggcccccat gtttactcaa   3060

cctttggtta acacctatgc catcgctggt tacaatgcca ccctgaactg cagcgtccga   3120

ggaaatccca agcccaaaat cacctggatg aaaaacaaag tggctattgt ggatgaccca   3180

agatacagaa tgttcagcaa ccaaggagtc tgtaccctgg agatccgcaa gcctagtcct   3240

tatgacggag gcacgtactg ctgcaaagca gtcaatgacc tcgggacggt ggagattgaa   3300

tgcaaactgg aggtgaaagg tgggctgtcc ttctgcaggc tcctcctgca aggcgtgcct   3360

ccaaacataa ttgattccta tttgcgagac ttacaatcaa gcaatcccga ggaatactga   3420

gggcagggca ttgcttctag acacacccac tgctttgaaa tctgattgaa aatggatagt   3480

actttctggt tttctcccag gcccccaagt gtggtcactt tctttctttc ctcctaactt   3540

tgaagaaagt                                                          3550
```

```
<210> SEQ ID NO 20
<211> LENGTH: 1141
<212> TYPE: PRT
<213> ORGANISM: Mus musculus

<400> SEQUENCE: 20

Met Pro Glu Pro Thr Lys Lys Glu Glu Asn Glu Val Pro Ala Pro Ala
1               5                   10                  15

Pro Pro Pro Glu Glu Pro Ser Lys Glu Lys Glu Ala Gly Thr Thr Pro
            20                  25                  30

Ala Lys Asp Trp Thr Leu Val Glu Thr Pro Pro Gly Glu Glu Gln Ala
        35                  40                  45

Lys Gln Asn Ala Asn Ser Gln Leu Ser Ile Leu Phe Ile Glu Lys Pro
    50                  55                  60

Gln Gly Gly Thr Val Lys Val Gly Glu Asp Ile Thr Phe Ile Ala Lys
65                  70                  75                  80

Val Lys Ala Glu Asp Leu Leu Arg Lys Pro Thr Ile Lys Trp Phe Lys
                85                  90                  95

Gly Lys Trp Met Asp Leu Ala Ser Lys Ala Gly Lys His Leu Gln Leu
```

```
            100                 105                 110

Lys Glu Thr Phe Glu Arg His Ser Arg Val Tyr Thr Phe Glu Met Gln
        115                 120                 125

Ile Ile Lys Ala Lys Asp Asn Phe Ala Gly Asn Tyr Arg Cys Glu Val
    130                 135                 140

Thr Tyr Lys Asp Lys Phe Asp Ser Cys Ser Phe Asp Leu Glu Val His
145                 150                 155                 160

Glu Ser Thr Gly Thr Thr Pro Asn Ile Asp Ile Arg Ser Ala Phe Lys
                165                 170                 175

Arg Ser Gly Glu Gly Gln Glu Asp Ala Gly Glu Leu Asp Phe Ser Gly
            180                 185                 190

Leu Leu Lys Arg Arg Glu Val Lys Gln Gln Glu Glu Glu Pro Gln Val
        195                 200                 205

Asp Val Trp Glu Leu Leu Lys Asn Ala Lys Pro Ser Glu Tyr Glu Lys
    210                 215                 220

Ile Ala Phe Gln Tyr Gly Ile Thr Asp Leu Arg Gly Met Leu Lys Arg
225                 230                 235                 240

Leu Lys Arg Met Arg Arg Glu Glu Lys Lys Ser Ala Ala Phe Ala Lys
                245                 250                 255

Ile Leu Asp Pro Ala Tyr Gln Val Asp Lys Gly Gly Arg Val Arg Phe
            260                 265                 270

Val Val Glu Leu Ala Asp Pro Lys Leu Glu Val Lys Trp Tyr Lys Asn
        275                 280                 285

Gly Gln Glu Ile Arg Pro Ser Thr Lys Tyr Ile Phe Glu His Lys Gly
    290                 295                 300

Cys Gln Arg Ile Leu Phe Ile Asn Asn Cys Gln Met Thr Asp Asp Ser
305                 310                 315                 320

Glu Tyr Tyr Val Thr Ala Gly Asp Glu Lys Cys Ser Thr Glu Leu Phe
                325                 330                 335

Val Arg Glu Pro Pro Ile Met Val Thr Lys Gln Leu Glu Asp Thr Thr
            340                 345                 350

Ala Tyr Cys Gly Glu Arg Val Glu Leu Glu Cys Glu Val Ser Glu Asp
        355                 360                 365

Asp Ala Asn Val Lys Trp Phe Lys Asn Gly Glu Glu Ile Ile Pro Gly
    370                 375                 380

Pro Lys Ser Arg Tyr Arg Ile Arg Val Glu Gly Lys Lys His Ile Leu
385                 390                 395                 400

Ile Ile Glu Gly Ala Thr Lys Ala Asp Ala Ala Glu Tyr Ser Val Met
                405                 410                 415

Thr Thr Gly Gly Gln Ser Ser Ala Lys Leu Ser Val Asp Leu Lys Pro
            420                 425                 430

Leu Lys Ile Leu Thr Pro Leu Thr Asp Gln Thr Val Asn Leu Gly Lys
        435                 440                 445

Glu Ile Cys Leu Lys Cys Glu Ile Ser Glu Asn Ile Pro Gly Lys Trp
    450                 455                 460

Thr Lys Asn Gly Leu Pro Val Gln Glu Ser Asp Arg Leu Lys Val Val
465                 470                 475                 480

His Lys Gly Arg Ile His Lys Leu Val Ile Ala Asn Ala Leu Thr Glu
                485                 490                 495

Asp Glu Gly Asp Tyr Val Phe Ala Pro Asp Ala Tyr Asn Val Thr Leu
            500                 505                 510

Pro Ala Lys Val His Val Ile Asp Pro Pro Lys Ile Ile Leu Asp Gly
        515                 520                 525
```

```
Leu Asp Ala Asp Asn Thr Val Thr Val Ile Ala Gly Asn Lys Leu Arg
    530                 535                 540

Leu Glu Ile Pro Ile Ser Gly Glu Pro Pro Pro Lys Ala Met Trp Ser
545                 550                 555                 560

Arg Gly Asp Lys Ala Ile Met Glu Gly Ser Gly Arg Ile Arg Thr Glu
                565                 570                 575

Ser Tyr Pro Asp Ser Ser Thr Leu Val Ile Asp Ile Ala Glu Arg Asp
            580                 585                 590

Asp Ser Gly Val Tyr His Ile Asn Leu Lys Asn Glu Ala Gly Glu Ala
        595                 600                 605

His Ala Ser Ile Lys Val Lys Val Val Asp Phe Pro Asp Pro Pro Val
    610                 615                 620

Ala Pro Thr Val Thr Glu Val Gly Asp Asp Trp Cys Ile Met Asn Trp
625                 630                 635                 640

Glu Pro Pro Ala Tyr Asp Gly Gly Ser Pro Ile Leu Gly Tyr Phe Ile
                645                 650                 655

Glu Arg Lys Lys Lys Gln Ser Ser Arg Trp Met Arg Leu Asn Phe Asp
            660                 665                 670

Leu Cys Lys Glu Thr Thr Phe Glu Pro Lys Lys Met Ile Glu Gly Val
        675                 680                 685

Ala Tyr Glu Val Arg Ile Phe Ala Val Asn Ala Ile Gly Ile Ser Lys
    690                 695                 700

Pro Ser Met Pro Ser Arg Pro Phe Val Pro Leu Ala Val Thr Ser Pro
705                 710                 715                 720

Pro Thr Leu Leu Thr Val Asp Ser Val Thr Asp Thr Thr Val Thr Met
                725                 730                 735

Arg Trp Arg Pro Pro Asp His Ile Gly Ala Ala Gly Leu Asp Gly Tyr
            740                 745                 750

Val Leu Glu Tyr Cys Phe Glu Gly Ser Thr Ser Ala Lys Gln Ser Asp
        755                 760                 765

Glu Asn Gly Glu Ala Ala Tyr Asp Leu Pro Ala Glu Asp Trp Ile Val
    770                 775                 780

Ala Asn Lys Asp Leu Ile Asp Lys Thr Lys Phe Thr Ile Thr Gly Leu
785                 790                 795                 800

Pro Thr Asp Ala Lys Ile Phe Val Arg Val Lys Ala Val Asn Ala Ala
                805                 810                 815

Gly Ala Ser Glu Pro Lys Tyr Tyr Ser Gln Pro Ile Leu Val Lys Glu
            820                 825                 830

Ile Ile Glu Pro Pro Lys Ile Arg Ile Pro Arg His Leu Lys Gln Thr
        835                 840                 845

Tyr Ile Arg Arg Val Gly Glu Ala Val Asn Leu Val Ile Pro Phe Gln
    850                 855                 860

Gly Lys Pro Arg Pro Glu Leu Thr Trp Lys Lys Asp Gly Ala Glu Ile
865                 870                 875                 880

Asp Lys Asn Gln Ile Asn Ile Arg Asn Ser Glu Thr Asp Thr Ile Ile
                885                 890                 895

Phe Ile Arg Lys Ala Glu Arg Ser His Ser Gly Lys Tyr Asp Leu Gln
            900                 905                 910

Val Lys Val Asp Lys Phe Val Glu Thr Ala Ser Ile Asp Ile Gln Ile
        915                 920                 925

Ile Asp Arg Pro Gly Pro Pro Gln Ile Val Lys Ile Glu Asp Val Trp
    930                 935                 940
```

Gly Glu Asn Val Ala Leu Thr Trp Thr Pro Pro Lys Asp Asp Gly Asn
945 950 955 960

Ala Ala Ile Thr Gly Tyr Thr Ile Gln Lys Ala Asp Lys Lys Ser Met
965 970 975

Glu Trp Phe Thr Val Ile Glu His Tyr His Arg Thr Ser Ala Thr Ile
980 985 990

Thr Glu Leu Val Ile Gly Asn Glu Tyr Tyr Phe Arg Val Phe Ser Glu
995 1000 1005

Asn Met Cys Gly Leu Ser Glu Asp Ala Thr Met Thr Lys Glu Ser
1010 1015 1020

Ala Val Ile Ala Arg Asp Gly Lys Ile Tyr Lys Asn Pro Val Tyr
1025 1030 1035

Glu Asp Phe Asp Phe Ser Glu Ala Pro Met Phe Thr Gln Pro Leu
1040 1045 1050

Val Asn Thr Tyr Ala Ile Ala Gly Tyr Asn Ala Thr Leu Asn Cys
1055 1060 1065

Ser Val Arg Gly Asn Pro Lys Pro Lys Ile Thr Trp Met Lys Asn
1070 1075 1080

Lys Val Ala Ile Val Asp Asp Pro Arg Tyr Arg Met Phe Ser Asn
1085 1090 1095

Gln Gly Val Cys Thr Leu Glu Ile Arg Lys Pro Ser Pro Tyr Asp
1100 1105 1110

Gly Gly Thr Tyr Cys Cys Lys Ala Val Asn Asp Leu Gly Thr Val
1115 1120 1125

Glu Ile Glu Cys Lys Leu Glu Val Lys Val Ile Ala Gln
1130 1135 1140

<210> SEQ ID NO 21
<211> LENGTH: 3201
<212> TYPE: DNA
<213> ORGANISM: Artificial Sequence
<220> FEATURE:
<223> OTHER INFORMATION: Wild-type cMyBP-C C0-C7 domains with SpyCatcher followed by a TEV recognition site, His Tag, and stop codon

<400> SEQUENCE: 21
atgccggagc cgggtaaaaa gccggttagc gcgttcaaca aaaaaccgcg tagcgcggaa 60
gtgaccgcgg gtagcgcggc ggtgtttgag gcggaaaccg agcgtagcgg cgttaaagtg 120
cgttggcaac gtgacggtag cgatattacc gcgaacgata aatacggtct ggcggcggaa 180
ggcaagcgtc acaccctgac cgttcgtgat gcgagcccgg acgatcaggg tagctatgcg 240
gtgatcgcgg gcagcagcaa ggtgaaattt gacctgaaag ttaccgagcc ggctccgccg 300
gaaaaagcgg aaagcgaggt ggcgccgggt gcgccgaagg aagttccggc gccggcgacc 360
gagctggagg aaagcgtgag cagcccggaa ggcagcgtta gcgtgaccca ggatggtagc 420
gcggcggaac atcaaggtgc gccggatgat ccgatcggtc tgttcctgat gcgtccgcaa 480
gacggtgagg ttaccgtggg tggcagcatt gtgtttagcg cgcgtgttgc gggtgcgagc 540
ctgctgaaac cgccggtggt taagtggttc aagggcaaat gggtggatct gagcagcaaa 600
gttggtcagc acctgcaact gcacgacagc tacgatcgtg cgagcaaggt ttacctgttc 660
gaactgcaca ttaccgatgc gcagaccacc agcgcgggtg gctaccgttg cgaggttagc 720
accaaggaca aattcgatag ctgcaacttt aacctgaccg tgcacgaagc gatcggtagc 780
ggcgacctgg atctgcgtag cgcgtttcgt cgtaccagcc tggcgggtgc gggtcgtcgt 840
accagcgaca gccatgagga tgcgggcacc ctggatttca gcagcctgct gaagaaacgt 900

```
gatagctttc gtcgtgacag caaactggaa gcgccggcgg aggaagacgt ttgggagatc    960
ctgcgtcaag ctccgccgag cgaatacgag cgtattgcgt tccagcacgg tgtgaccgat   1020
ctgcgtggca tgctgaagcg tctgaagggt atgaagcagg acgaaaagaa aagcaccgcg   1080
tttcagaaga aactggagcc ggcgtatcaa gtgaacaaag gccacaagat ccgtctgacc   1140
gtggaactgg cggacccgga tgcggaagtg aaatggctga agaacggcca ggaaatccaa   1200
atgagcggta gcaaatacat tttcgagagc gttggtgcga agcgtaccct gaccattagc   1260
caatgcagcc tggcggacga tgcggcgtat cagtgcgtgg ttggtggcga gaaatgcagc   1320
accgaactgt tcgtgaagga gccgccggtt ctgatcaccc gtagcctgga agatcagctg   1380
gttatggtgg gtcaacgtgt ggaatttgag tgcgaagtta gcgaggaagg cgcgcaagtg   1440
aaatggctga aggacggtgt tgagctgacc cgtgaggaaa ccttcaaata ccgttttaag   1500
aaagatggtc gtaagcacca cctgatcatt aacgaagcga ccctggagga tgcgggtcac   1560
tatgcggttc gtaccagcgg tggccagagc ctggcggaac tgatcgtgca agaaaagaaa   1620
ctggaagtgt atcagagcat tgcggatctg gcggtgggtg cgaaagacca ggcggtgttc   1680
aagtgcgaag ttagcgatga gaacgttcgt ggtgtgtggc tgaaaaacgg caaggagctg   1740
gttccggaca accgtatcaa agtgagccac attggtcgtg ttcacaagct gaccatcgac   1800
gatgttaccc cggcggacga agcggattat agcttcgtgc cggagggctt tgcgtgcaac   1860
ctgagcgcga aactgcactt catggaagtg aagatcgact ttgttccgcg tcaggagccg   1920
ccgaaaattc atctggattg cccgggtagc accccggaca ccattgtggt tgtggcgggt   1980
aacaaactgc gtctggatgt gccgattagc ggcgacccgg cgccgaccgt tgtgtggcag   2040
aagaccgtga cccaaggtaa gaaagcgagc accggtccgc acccggatgc gccggaggat   2100
gcgggtgcgg acgaggaatg ggttttcgat aagaaactgc tgtgcgaaac cgaaggccgt   2160
gttcgtgtgg aaaccaccaa ggatcgtagc gtttttaccg tggagggcgc ggagaaagaa   2220
gacgagggtg tttacaccgt taccgtgaag aacccggtgg gtgaagacca ggttaacctg   2280
accgttaaag ttattgatgt tccggatgcg ccggcggcgc cgaagattag caacgtgggt   2340
gaagatagct gcaccgttca atgggagccg ccggcgtatg atggtggcca gccggtgctg   2400
ggctatatcc tggagcgtaa gaaaaagaaa agctatcgtt ggatgcgtct gaacttcgac   2460
ctgctgcgtg aactgagcca cgaggcgcgt cgtatgattg aaggtgttgc gtacgagatg   2520
cgtgtttatg cggtgaacgc ggttggtatg agccgtccga gcccggcgag ccagccgttt   2580
atgccgattg gtccgccggg tgaaccgacc cacctggcgg tggaggacgt tagcgatacc   2640
accgtgagcc tgaaatggcg tccgccggaa cgtgttggtg cgggtggcct ggatggctac   2700
agcgtggaat attgccaaga gggctgcagc gaatggaccc cggcgctgca gggtctgacc   2760
gagcgtacca gcatgctggt taaagacctg ccgaccggtg cgcgtctgct gttccgtgtg   2820
cgtgcgcata acgttgcggg tccgggtggc ccgatcgtga ccaaggaacc ggttaccgtg   2880
caggagatta gcggtgatag cgcgacccac attaaattta gcaagcgtga cgaggatggt   2940
aaagaactgg cgggcgcgac catggaactg cgtgacagca gcggcaagac catcagcacc   3000
tggattagcg atggtcaggt taaagacttc tacctgtatc cgggcaagta cacctttgtg   3060
gaaaccgcgg cgccggatgg ttatgaggtg gcgaccgcga tcaccttcac cgttaacgag   3120
cagggtcaag ttaccgtgaa cggtaaagcg accaagggcg agaatctgta tttccagggt   3180
catcaccacc accatcacta a                                             3201
```

<210> SEQ ID NO 22
<211> LENGTH: 3201
<212> TYPE: DNA
<213> ORGANISM: Artificial Sequence
<220> FEATURE:
<223> OTHER INFORMATION: wild-type cMyBP-C C0-C7 domains containing a [E330K] mutation, SpyCatcher, TEV recognition site, His Tag, and Stop codon

<400> SEQUENCE: 22
atgccggagc cgggtaaaaa gccggttagc gcgttcaaca aaaaaccgcg tagcgcggaa 60
gtgaccgcgg gtagcgcggc ggtgtttgag gcggaaaccg agcgtagcgg cgttaaagtg 120
cgttggcaac gtgacggtag cgatattacc gcgaacgata aatacggtct ggcggcggaa 180
ggcaagcgtc acaccctgac cgttcgtgat gcgagcccgg acgatcaggg tagctatgcg 240
gtgatcgcgg gcagcagcaa ggtgaaattt gacctgaaag ttaccgagcc ggctccgccg 300
gaaaaagcgg aaagcgaggt ggcgccgggt gcgccgaagg aagttccggc gccggcgacc 360
gagctggagg aaagcgtgag cagcccggaa ggcagcgtta gcgtgaccca ggatggtagc 420
gcggcggaac atcaaggtgc gccggatgat ccgatcggtc tgttcctgat gcgtccgcaa 480
gacggtgagg ttaccgtggg tggcagcatt gtgtttagcg cgcgtgttgc gggtgcgagc 540
ctgctgaaac cgccggtggt taagtggttc aagggcaaat gggtggatct gagcagcaaa 600
gttggtcagc acctgcaact gcacgacagc tacgatcgtg cgagcaaggt ttacctgttc 660
gaactgcaca ttaccgatgc gcagaccacc agcgcgggtg gctaccgttg cgaggttagc 720
accaaggaca aattcgatag ctgcaacttt aacctgaccg tgcacgaagc gatcggtagc 780
ggcgacctgg atctgcgtag cgcgtttcgt cgtaccagcc tggcgggtgc gggtcgtcgt 840
accagcgaca gccatgagga tgcgggcacc ctggatttca gcagcctgct gaagaaacgt 900
gatagctttc gtcgtgacag caaactggaa gcgccggcgg aggaagacgt ttgggagatc 960
ctgcgtcaag ctccgccaag cgaatacgag cgtattgcgt tccagcacgg tgtgaccgat 1020
ctgcgtggca tgctgaagcg tctgaagggt atgaagcagg acgaaaagaa aagcaccgcg 1080
tttcagaaga aactggagcc ggcgtatcaa gtgaacaaag gccacaagat ccgtctgacc 1140
gtggaactgg cggacccgga tgcggaagtg aaatggctga agaacggcca ggaaatccaa 1200
atgagcggta gcaaatacat tttcgagagc gttggtgcga agcgtaccct gaccattagc 1260
caatgcagcc tggcggacga tgcggcgtat cagtgcgtgg ttggtggcga gaaatgcagc 1320
accgaactgt tcgtgaagga gccgccggtt ctgatcaccc gtagcctgga agatcagctg 1380
gttatggtgg gtcaacgtgt ggaatttgag tgcgaagtta gcgaggaagg cgcgcaagtg 1440
aaatggctga aggacggtgt tgagctgacc cgtgaggaaa ccttcaaata ccgttttaag 1500
aaagatggtc gtaagcacca cctgatcatt aacgaagcga ccctggagga tgcgggtcac 1560
tatgcggttc gtaccagcgg tggccagagc ctggcggaac tgatcgtgca agaaaagaaa 1620
ctggaagtgt atcagagcat tgcggatctg gcggtgggtg cgaaagacca ggcggtgttc 1680
aagtgcgaag ttagcgatga gaacgttcgt ggtgtgtggc tgaaaaacgg caaggagctg 1740
gttccggaca accgtatcaa agtgagccac attggtcgtg ttcacaagct gaccatcgac 1800
gatgttaccc cggcggacga agcggattat agcttcgtgc cggagggctt tgcgtgcaac 1860
ctgagcgcga aactgcactt catggaagtg aagatcgact ttgttccgcg tcaggagccg 1920
ccgaaaattc atctggattg cccgggtagc accccggaca ccattgtggt tgtggcgggt 1980
aacaaactgc gtctggatgt gccgattagc ggcgacccgg cgccgaccgt tgtgtggcag 2040

```
aagaccgtga cccaaggtaa gaaagcgagc accggtccgc acccggatgc gccggaggat   2100

gcgggtgcgg acgaggaatg ggttttcgat aagaaactgc tgtgcgaaac cgaaggccgt   2160

gttcgtgtgg aaaccaccaa ggatcgtagc gtttttaccg tggagggcgc ggagaaagaa   2220

gacgagggtg tttacaccgt taccgtgaag aacccggtgg gtgaagacca ggttaacctg   2280

accgttaaag ttattgatgt tccggatgcg ccggcggcgc cgaagattag caacgtgggt   2340

gaagatagct gcaccgttca atgggagccg ccggcgtatg atggtggcca gccggtgctg   2400

ggctatatcc tggagcgtaa gaaaaagaaa agctatcgtt ggatgcgtct gaacttcgac   2460

ctgctgcgtg aactgagcca cgaggcgcgt cgtatgattg aaggtgttgc gtacgagatg   2520

cgtgtttatg cggtgaacgc ggttggtatg agccgtccga gcccggcgag ccagccgttt   2580

atgccgattg gtccgccggg tgaaccgacc cacctggcgg tggaggacgt tagcgatacc   2640

accgtgagcc tgaaatggcg tccgccggaa cgtgttggtg cgggtggcct ggatggctac   2700

agcgtggaat attgccaaga gggctgcagc gaatggaccc cggcgctgca gggtctgacc   2760

gagcgtacca gcatgctggt taaagacctg ccgaccggtg cgcgtctgct gttccgtgtg   2820

cgtgcgcata acgttgcggg tccgggtggc ccgatcgtga ccaaggaacc ggttaccgtg   2880

caggagatta gcggtgatag cgcgacccac attaaattta gcaagcgtga cgaggatggt   2940

aaagaactgg cgggcgcgac catggaactg cgtgacagca gcggcaagac catcagcacc   3000

tggattagcg atggtcaggt taaagacttc tacctgtatc cgggcaagta cacctttgtg   3060

gaaaccgcgg cgccggatgg ttatgaggtg gcgaccgcga tcaccttcac cgttaacgag   3120

cagggtcaag ttaccgtgaa cggtaaagcg accaagggcg agaatctgta tttccagggt   3180

catcaccacc accatcacta a                                             3201
```

<210> SEQ ID NO 23
<211> LENGTH: 3201
<212> TYPE: DNA
<213> ORGANISM: Artificial Sequence
<220> FEATURE:
<223> OTHER INFORMATION: wild-type cMyBP-C C0-C7 domains containing a [L348P] mutation, SpyCatcher, TEV recognition site, His Tag, and stop codon

<400> SEQUENCE: 23

```
atgccggagc cgggtaaaaa gccggttagc gcgttcaaca aaaaaccgcg tagcgcggaa     60

gtgaccgcgg gtagcgcggc ggtgtttgag gcggaaaccg agcgtagcgg cgttaaagtg    120

cgttggcaac gtgacggtag cgatattacc gcgaacgata aatacggtct ggcggcggaa    180

ggcaagcgtc acaccctgac cgttcgtgat gcgagcccgg acgatcaggg tagctatgcg    240

gtgatcgcgg gcagcagcaa ggtgaaattt gacctgaaag ttaccgagcc ggctccgccg    300

gaaaaagcgg aaagcgaggt ggcgccgggt gcgccgaagg aagttccggc gccggcgacc    360

gagctggagg aaagcgtgag cagcccggaa ggcagcgtta gcgtgaccca ggatggtagc    420

gcggcggaac atcaaggtgc gccggatgat ccgatcggtc tgttcctgat gcgtccgcaa    480

gacggtgagg ttaccgtggg tggcagcatt gtgtttagcg cgcgtgttgc gggtgcgagc    540

ctgctgaaac cgccggtggt taagtggttc aagggcaaat gggtggatct gagcagcaaa    600

gttggtcagc acctgcaact gcacgacagc tacgatcgtg cgagcaaggt ttacctgttc    660

gaactgcaca ttaccgatgc gcagaccacc agcgcgggtg gctaccgttg cgaggttagc    720

accaaggaca aattcgatag ctgcaacttt aacctgaccg tgcacgaagc gatcggtagc    780
```

```
ggcgacctgg atctgcgtag cgcgtttcgt cgtaccagcc tggcgggtgc gggtcgtcgt    840
accagcgaca gccatgagga tgcgggcacc ctggatttca gcagcctgct gaagaaacgt    900
gatagctttc gtcgtgacag caaactggaa gcgccggcgg aggaagacgt ttgggagatc    960
ctgcgtcaag ctccgccgag cgaatacgag cgtattgcgt tccagcacgg tgtgaccgat   1020
ctgcgtggca tgctgaagcg tccgaagggt atgaagcagg acgaaaagaa aagcaccgcg   1080
tttcagaaga aactggagcc ggcgtatcaa gtgaacaaag gccacaagat ccgtctgacc   1140
gtggaactgg cggacccgga tgcggaagtg aaatggctga agaacggcca ggaaatccaa   1200
atgagcggta gcaaatacat tttcgagagc gttggtgcga agcgtaccct gaccattagc   1260
caatgcagcc tggcggacga tgcggcgtat cagtgcgtgg ttggtggcga gaaatgcagc   1320
accgaactgt tcgtgaagga gccgccggtt ctgatcaccc gtagcctgga agatcagctg   1380
gttatggtgg gtcaacgtgt ggaatttgag tgcgaagtta gcgaggaagg cgcgcaagtg   1440
aaatggctga aggacggtgt tgagctgacc cgtgaggaaa ccttcaaata ccgttttaag   1500
aaagatggtc gtaagcacca cctgatcatt aacgaagcga ccctggagga tgcgggtcac   1560
tatgcggttc gtaccagcgg tggccagagc ctggcggaac tgatcgtgca agaaaagaaa   1620
ctggaagtgt atcagagcat tgcggatctg gcggtgggtg cgaaagacca ggcggtgttc   1680
aagtgcgaag ttagcgatga gaacgttcgt ggtgtgtggc tgaaaaacgg caaggagctg   1740
gttccggaca accgtatcaa agtgagccac attggtcgtg ttcacaagct gaccatcgac   1800
gatgttaccc cggcggacga agcggattat agcttcgtgc cggagggctt tgcgtgcaac   1860
ctgagcgcga aactgcactt catggaagtg aagatcgact ttgttccgcg tcaggagccg   1920
ccgaaaattc atctggattg cccgggtagc accccggaca ccattgtggt tgtggcgggt   1980
aacaaactgc gtctggatgt gccgattagc ggcgacccgg cgccgaccgt tgtgtggcag   2040
aagaccgtga cccaaggtaa gaaagcgagc accggtccgc acccggatgc gccggaggat   2100
gcgggtgcgg acgaggaatg ggttttcgat aagaaactgc tgtgcgaaac cgaaggccgt   2160
gttcgtgtgg aaaccaccaa ggatcgtagc gtttttaccg tggagggcgc ggagaaagaa   2220
gacgagggtg tttacaccgt taccgtgaag aacccggtgg gtgaagacca ggttaacctg   2280
accgttaaag ttattgatgt tccggatgcg ccggcggcgc cgaagattag caacgtgggt   2340
gaagatagct gcaccgttca atgggagccg ccggcgtatg atggtggcca gccggtgctg   2400
ggctatatcc tggagcgtaa gaaaaagaaa agctatcgtt ggatgcgtct gaacttcgac   2460
ctgctgcgtg aactgagcca cgaggcgcgt cgtatgattg aaggtgttgc gtacgagatg   2520
cgtgtttatg cggtgaacgc ggttggtatg agccgtccga gcccggcgag ccagccgttt   2580
atgccgattg gtccgccggg tgaaccgacc cacctggcgg tggaggacgt tagcgatacc   2640
accgtgagcc tgaaatggcg tccgccggaa cgtgttggtg cgggtggcct ggatggctac   2700
agcgtggaat attgccaaga gggctgcagc gaatggaccc cggcgctgca gggtctgacc   2760
gagcgtacca gcatgctggt taaagacctg ccgaccggtg cgcgtctgct gttccgtgtg   2820
cgtgcgcata acgttgcggg tccgggtggc ccgatcgtga ccaaggaacc ggttaccgtg   2880
caggagatta gcggtgatag cgcgacccac attaaattta gcaagcgtga cgaggatggt   2940
aaagaactgg cgggcgcgac catggaactg cgtgacagca gcggcaagac catcagcacc   3000
tggattagcg atggtcaggt taaagacttc tacctgtatc cgggcaagta cacctttgtg   3060
gaaaccgcgg cgccggatgg ttatgaggtg gcgaccgcga tcaccttcac cgttaacgag   3120
cagggtcaag ttaccgtgaa cggtaaagcg accaagggcg agaatctgta tttccagggt   3180
```

catcaccacc accatcacta a 3201

<210> SEQ ID NO 24
<211> LENGTH: 1374
<212> TYPE: PRT
<213> ORGANISM: Artificial Sequence
<220> FEATURE:
<223> OTHER INFORMATION: cMyBP-c with SpyCatcher and SpyTag inserted in between domains C7 and C8 of cMyBP-c

<400> SEQUENCE: 24

Met Pro Glu Pro Gly Lys Lys Pro Val Ser Ala Phe Asn Lys Lys Pro
1 5 10 15

Arg Ser Ala Glu Val Thr Ala Gly Ser Ala Ala Val Phe Glu Ala Glu
20 25 30

Thr Glu Arg Ser Gly Val Lys Val Arg Trp Gln Arg Asp Gly Ser Asp
35 40 45

Ile Thr Ala Asn Asp Lys Tyr Gly Leu Ala Ala Glu Gly Lys Arg His
50 55 60

Thr Leu Thr Val Arg Asp Ala Ser Pro Asp Asp Gln Gly Ser Tyr Ala
65 70 75 80

Val Ile Ala Gly Ser Ser Lys Val Lys Phe Asp Leu Lys Val Thr Glu
85 90 95

Pro Ala Pro Pro Glu Lys Ala Glu Ser Glu Val Ala Pro Gly Ala Pro
100 105 110

Lys Glu Val Pro Ala Pro Ala Thr Glu Leu Glu Glu Ser Val Ser Ser
115 120 125

Pro Glu Gly Ser Val Ser Val Thr Gln Asp Gly Ser Ala Ala Glu His
130 135 140

Gln Gly Ala Pro Asp Asp Pro Ile Gly Leu Phe Leu Met Arg Pro Gln
145 150 155 160

Asp Gly Glu Val Thr Val Gly Gly Ser Ile Val Phe Ser Ala Arg Val
165 170 175

Ala Gly Ala Ser Leu Leu Lys Pro Pro Val Val Lys Trp Phe Lys Gly
180 185 190

Lys Trp Val Asp Leu Ser Ser Lys Val Gly Gln His Leu Gln Leu His
195 200 205

Asp Ser Tyr Asp Arg Ala Ser Lys Val Tyr Leu Phe Glu Leu His Ile
210 215 220

Thr Asp Ala Gln Thr Thr Ser Ala Gly Gly Tyr Arg Cys Glu Val Ser
225 230 235 240

Thr Lys Asp Lys Phe Asp Ser Cys Asn Phe Asn Leu Thr Val His Glu
245 250 255

Ala Ile Gly Ser Gly Asp Leu Asp Leu Arg Ser Ala Phe Arg Arg Thr
260 265 270

Ser Leu Ala Gly Ala Gly Arg Arg Thr Ser Asp Ser His Glu Asp Ala
275 280 285

Gly Thr Leu Asp Phe Ser Ser Leu Leu Lys Lys Arg Asp Ser Phe Arg
290 295 300

Arg Asp Ser Lys Leu Glu Ala Pro Ala Glu Glu Asp Val Trp Glu Ile
305 310 315 320

Leu Arg Gln Ala Pro Pro Ser Glu Tyr Glu Arg Ile Ala Phe Gln His
325 330 335

Gly Val Thr Asp Leu Arg Gly Met Leu Lys Arg Leu Lys Gly Met Lys
340 345 350

```
Gln Asp Glu Lys Lys Ser Thr Ala Phe Gln Lys Lys Leu Glu Pro Ala
        355                 360                 365

Tyr Gln Val Asn Lys Gly His Lys Ile Arg Leu Thr Val Glu Leu Ala
    370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                405                 410                 415

Leu Thr Ile Ser Gln Cys Ser Leu Ala Asp Asp Ala Ala Tyr Gln Cys
            420                 425                 430

Val Val Gly Gly Glu Lys Cys Ser Thr Glu Leu Phe Val Lys Glu Pro
        435                 440                 445

Pro Val Leu Ile Thr Arg Ser Leu Glu Asp Gln Leu Val Met Val Gly
    450                 455                 460

Gln Arg Val Glu Phe Glu Cys Glu Val Ser Glu Glu Gly Ala Gln Val
465                 470                 475                 480

Lys Trp Leu Lys Asp Gly Val Glu Leu Thr Arg Glu Glu Thr Phe Lys
                485                 490                 495

Tyr Arg Phe Lys Lys Asp Gly Arg Lys His His Leu Ile Ile Asn Glu
            500                 505                 510

Ala Thr Leu Glu Asp Ala Gly His Tyr Ala Val Arg Thr Ser Gly Gly
        515                 520                 525

Gln Ser Leu Ala Glu Leu Ile Val Gln Glu Lys Lys Leu Glu Val Tyr
    530                 535                 540

Gln Ser Ile Ala Asp Leu Ala Val Gly Ala Lys Asp Gln Ala Val Phe
545                 550                 555                 560

Lys Cys Glu Val Ser Asp Glu Asn Val Arg Gly Val Trp Leu Lys Asn
                565                 570                 575

Gly Lys Glu Leu Val Pro Asp Asn Arg Ile Lys Val Ser His Ile Gly
            580                 585                 590

Arg Val His Lys Leu Thr Ile Asp Asp Val Thr Pro Ala Asp Glu Ala
        595                 600                 605

Asp Tyr Ser Phe Val Pro Glu Gly Phe Ala Cys Asn Leu Ser Ala Lys
    610                 615                 620

Leu His Phe Met Glu Val Lys Ile Asp Phe Val Pro Arg Gln Glu Pro
625                 630                 635                 640

Pro Lys Ile His Leu Asp Cys Pro Gly Ser Thr Pro Asp Thr Ile Val
                645                 650                 655

Val Val Ala Gly Asn Lys Leu Arg Leu Asp Val Pro Ile Ser Gly Asp
            660                 665                 670

Pro Ala Pro Thr Val Val Trp Gln Lys Thr Val Thr Gln Gly Lys Lys
        675                 680                 685

Ala Ser Thr Gly Pro His Pro Asp Ala Pro Glu Asp Ala Gly Ala Asp
    690                 695                 700

Glu Glu Trp Val Phe Asp Lys Lys Leu Leu Cys Glu Thr Glu Gly Arg
705                 710                 715                 720

Val Arg Val Glu Thr Thr Lys Asp Arg Ser Val Phe Thr Val Glu Gly
                725                 730                 735

Ala Glu Lys Glu Asp Glu Gly Val Tyr Thr Val Thr Val Lys Asn Pro
            740                 745                 750

Val Gly Glu Asp Gln Val Asn Leu Thr Val Lys Val Ile Asp Val Pro
        755                 760                 765
```

-continued

```
Asp Ala Pro Ala Ala Pro Lys Ile Ser Asn Val Gly Glu Asp Ser Cys
    770                 775                 780

Thr Val Gln Trp Glu Pro Pro Ala Tyr Asp Gly Gly Gln Pro Val Leu
785                 790                 795                 800

Gly Tyr Ile Leu Glu Arg Lys Lys Lys Lys Ser Tyr Arg Trp Met Arg
                805                 810                 815

Leu Asn Phe Asp Leu Leu Arg Glu Leu Ser His Glu Ala Arg Arg Met
            820                 825                 830

Ile Glu Gly Val Ala Tyr Glu Met Arg Val Tyr Ala Val Asn Ala Val
        835                 840                 845

Gly Met Ser Arg Pro Ser Pro Ala Ser Gln Pro Phe Met Pro Ile Gly
    850                 855                 860

Pro Pro Gly Glu Pro Thr His Leu Ala Val Glu Asp Val Ser Asp Thr
865                 870                 875                 880

Thr Val Ser Leu Lys Trp Arg Pro Pro Glu Arg Val Gly Ala Gly Gly
                885                 890                 895

Leu Asp Gly Tyr Ser Val Glu Tyr Cys Gln Glu Gly Cys Ser Glu Trp
            900                 905                 910

Thr Pro Ala Leu Gln Gly Leu Thr Glu Arg Thr Ser Met Leu Val Lys
        915                 920                 925

Asp Leu Pro Thr Gly Ala Arg Leu Leu Phe Arg Val Arg Ala His Asn
    930                 935                 940

Val Ala Gly Pro Gly Gly Pro Ile Val Thr Lys Glu Pro Val Thr Val
945                 950                 955                 960

Gln Glu Ile Ser Gly Asp Ser Ala Thr His Ile Lys Phe Ser Lys Arg
                965                 970                 975

Asp Glu Asp Gly Lys Glu Leu Ala Gly Ala Thr Met Glu Leu Arg Asp
            980                 985                 990

Ser Ser Gly Lys Thr Ile Ser Thr  Trp Ile Ser Asp Gly  Gln Val Lys
        995                 1000                1005

Asp Phe  Tyr Leu Tyr Pro Gly  Lys Tyr Thr Phe Val  Glu Thr Ala
    1010                1015                1020

Ala Pro  Asp Gly Tyr Glu Val  Ala Thr Ala Ile Thr  Phe Thr Val
    1025                1030                1035

Asn Glu  Gln Gly Gln Val Thr  Val Asn Gly Lys Ala  Thr Lys Gly
    1040                1045                1050

Gly Ala  His Ile Val Met Val  Asp Ala Tyr Lys Pro  Thr Lys Leu
    1055                1060                1065

Gln Arg  Pro Arg Leu Gln Leu  Pro Arg His Leu Arg  Gln Thr Ile
    1070                1075                1080

Gln Lys  Lys Val Gly Glu Pro  Val Asn Leu Leu Ile  Pro Phe Gln
    1085                1090                1095

Gly Lys  Pro Arg Pro Gln Val  Thr Trp Thr Lys Glu  Gly Gln Pro
    1100                1105                1110

Leu Ala  Gly Glu Glu Val Ser  Ile Arg Asn Ser Pro  Thr Asp Thr
    1115                1120                1125

Ile Leu  Phe Ile Arg Ala Ala  Arg Arg Thr His Ser  Gly Thr Tyr
    1130                1135                1140

Gln Val  Thr Val Arg Ile Glu  Asn Met Glu Asp Lys  Ala Thr Leu
    1145                1150                1155

Ile Leu  Gln Ile Val Asp Lys  Pro Ser Pro Pro Gln  Asp Ile Arg
    1160                1165                1170

Ile Val  Glu Thr Trp Gly Phe  Asn Val Ala Leu Glu  Trp Lys Pro
```

```
    1175                1180                1185

Pro Gln  Asp Asp Gly Asn Thr  Glu Ile Trp Gly Tyr  Thr Val Gln
    1190                1195                1200

Lys Ala  Asp Lys Lys Thr Met  Glu Trp Phe Thr Val  Leu Glu His
    1205                1210                1215

Tyr Arg  Arg Thr His Cys Val  Val Ser Glu Leu Ile  Ile Gly Asn
    1220                1225                1230

Gly Tyr  Tyr Phe Arg Val Phe  Ser His Asn Met Val  Gly Ser Ser
    1235                1240                1245

Asp Lys  Ala Ala Ala Thr Lys  Glu Pro Val Phe Ile  Pro Arg Pro
    1250                1255                1260

Gly Ile  Thr Tyr Glu Pro Pro  Lys Tyr Lys Ala Leu  Asp Phe Ser
    1265                1270                1275

Glu Ala  Pro Ser Phe Thr Gln  Pro Leu Ala Asn Arg  Ser Ile Ile
    1280                1285                1290

Ala Gly  Tyr Asn Ala Ile Leu  Cys Cys Ala Val Arg  Gly Ser Pro
    1295                1300                1305

Lys Pro  Lys Ile Ser Trp Phe  Lys Asn Gly Leu Asp  Leu Gly Glu
    1310                1315                1320

Asp Ala  Arg Phe Arg Met Phe  Cys Lys Gln Gly Val  Leu Thr Leu
    1325                1330                1335

Glu Ile  Arg Lys Pro Cys Pro  Tyr Asp Gly Gly Val  Tyr Val Cys
    1340                1345                1350

Arg Ala  Thr Asn Leu Gln Gly  Glu Ala Gln Cys Glu  Cys Arg Leu
    1355                1360                1365

Glu Val  Arg Val Pro Gln
    1370


<210> SEQ ID NO 25
<211> LENGTH: 7
<212> TYPE: PRT
<213> ORGANISM: Mus musculus

<400> SEQUENCE: 25

Val Gln Glu Ile Leu Gln Arg
1               5


<210> SEQ ID NO 26
<211> LENGTH: 8
<212> TYPE: PRT
<213> ORGANISM: Mus musculus

<400> SEQUENCE: 26

Pro Arg Leu Gln Leu Pro Arg His
1               5


<210> SEQ ID NO 27
<211> LENGTH: 10
<212> TYPE: PRT
<213> ORGANISM: Mus musculus

<400> SEQUENCE: 27

Pro Val Thr Ile Arg Glu Ile Val Glu Gln
1               5                   10


<210> SEQ ID NO 28
<211> LENGTH: 9
<212> TYPE: PRT
<213> ORGANISM: Mus musculus
```

<400> SEQUENCE: 28

Pro Lys Ile Arg Leu Pro Arg His Leu
1 5

METHODS AND COMPOSITIONS FOR RAPIDLY REPLACING CARDIAC MYOSIN BINDING PROTEIN-C IN SARCOMERES

CROSS-REFERENCES TO RELATED APPLICATIONS

This application is a continuation-in-part and claims benefit of U.S. patent application Ser. No. 16/579,445 filed Sep. 23, 2019, which is a non-provisional application and claims benefit of U.S. Patent Application No. 62/734,785 filed Sep. 21, 2018, the specification(s) of which is/are incorporated herein in their entirety by reference.

STATEMENT REGARDING FEDERALLY SPONSORED RESEARCH OR DEVELOPMENT

This invention was made with government support under Grant Nos. HL080367 and HL140925 awarded by National Institutes of Health. The government has certain rights in the invention.

REFERENCE TO A SEQUENCE LISTING

Applicant asserts that the paper copy of the Sequence Listing is identical to the Sequence Listing in computer readable form found on the accompanying computer file, entitled >>>UNIA_18_20_CIP_Sequence_Listing_ST25<<<. The content of the sequence listing is incorporated herein by reference in its entirety.

FIELD OF THE INVENTION

The present invention relates to myosin binding protein-C (MyBP-C), more particularly to methods and compositions for modifying MyBP-C in sarcomeres, e.g., protein engineering for studying MyBP-C in sarcomeres.

BACKGROUND OF THE INVENTION

Cardiac myosin binding protein-C (cMyBP-C) is a thick filament-associated protein localized to the C zones of striated muscle sarcomeres. cMyBP-C has a series of 11 folded domains numbered C0-C10, along with a regulatory "M"-domain between C1 and C2. The M-domain contains 3 cardiac-specific phosphorylation sites known to regulate effects of cMyBP-C in response to inotropic agonists, but 14 additional phosphorylation sites have been identified whose function is unknown. The N-terminal domains C0-C2 contribute to the regulatory effects of cMyBP-C on contraction in part by binding to the thin filament in a phosphorylation dependent manner. Domains C8-C10 anchor cMyBP-C to the thick filament.

cMyBP-C is a critical regulator of heart muscle contraction. Mutations in the gene that encodes cMyBP-C, MYPBC3, lead to hypertrophic cardiomyopathy (HCM), a heart muscle disease characterized by an abnormal thickening of the heart muscle.

There are currently no methods to rapidly replace cMyBP-C in sarcomeres, which creates a hurdle to evaluating aspects of cMyBP-C, such as determining the role of phosphorylation sites or the effects of mutations on the function of the protein. Unfortunately, cMyBP-C has an abundance of dynamic interactions that occur with binding partners in the sarcomere, making the study of this protein extremely complex. Also, manipulation of large, thick filaments such as myosin, titin, and cMyBP-C within muscle cells is very difficult.

Others have attempted to manipulate cMyBP-C using AAV methods or adenoviral methods but have achieved limited success. In vitro assays are also limited because they do not preserve the unique localization of cMyBP-C within the sarcomere and often use partial fragments of cMyBP-C (e.g., N-terminal domains only) in excess of the stoichiometry in sarcomeres.

BRIEF SUMMARY OF THE INVENTION

It is an objective of the present invention to provide methods and compositions that allow for a single gene-edited mouse model platform that allows for rapid exchange of new combinations of modified or mutant MyBP-C (e.g., phosphorylation site mutants, insertions, deletions, fluorescent probes, etc), as specified in the independent claims. Embodiments of the invention are given in the dependent claims. Embodiments of the present invention can be freely combined with each other if they are not mutually exclusive.

The present invention features recombinant protein comprising myosin binding protein C (MyBP-C) with an internal insertion therein, the internal insertion comprises at least a portion of a split-protein pair adjacent to a protease recognition site. In some embodiments, the internal insertion is within or between C1 and C8 domains of MyBP-C.

The present invention features methods and compositions for rapidly replacing cMyBP-C in its normal position in sarcomeres. The methods herein feature the use of a single gene-edited mouse model platform (Spy-C mice) that allows for rapid exchange of new combinations of modified or mutant cMyBP-C, such as phosphorylation site mutants, insertions, deletions, fluorescent probes, etc. Briefly, mice are genetically engineered to express cMyBP-C with a protease recognition site and SpyTag peptide introduced into the cMyBP-C gene. Surprisingly, as discussed below, these mice had overtly normal phenotypes. The protease recognition site allows the cMyBP-C protein to be cleaved to eliminate the N-Terminus, and the SpyTag peptide allows a different peptide to be attached to the remaining portion of cMyBP-C, thereby creating a modified or recombinant cMyBP-C protein. The methods and compositions of the present invention allow for a variety of modifications to be introduced to cMyBP-C in situ The methods and/or compositions of present invention may be used as a research tool, for example to study cMyBP-C (e.g., to study its function, its features, drug interactions, mutations that lead to diseases, etc.), or to study diseases such as hypertrophic cardiomyopathy, etc. In certain embodiments the methods and/or compositions of the present invention are used for drug screening assays (e.g., motility assays testing the effects of drugs). The present invention may also be applied to other proteins, such as skeletal muscle MyBP-C isoforms or other sarcomere proteins. There is also the potential to develop cell lines (e.g., stem cells) with a cassette (e.g., TEV/SpyTag cassette) in cMyBP-C or other sarcomere proteins.

Without wishing to limit the present invention to any theory or mechanisms, it is believed that the methods and compositions of the present invention are advantageous because they allow for the rapid introduction of genetic modifications to MyBP-C (e.g., cMyBP-C) in its native position in the sarcomere, allow for the study of MyBP-C (e.g, cMyBP-C) in living cells or animal models, and provide a platform to modify other sarcomeric proteins that cannot be manipulated using traditional methods.

Furthermore, the prior references teach away from the present invention. For example, all other approaches for studying MyBP-C in the sarcomere rely on genetic replacement of the whole or partial protein using transgenic animals or genetically modified cells (e.g., using viral infection and expression of MyBP-C). These methods can be costly and time consuming and only permit the study of one modification at a time (e.g., phosphorylation site modifications). By contrast, the present invention allows MyBP-C to be rapidly modified in sarcomeres within minutes increasing the throughput for testing effects of multiple modifications of MyBP-C using different recombinant proteins.

The present invention features methods of producing recombinant cMyBP-C proteins. In certain embodiments, the method comprises introducing a cassette for expressing a first recombinant cMyBP-C into a genome of a host (e.g., mouse, etc.), wherein the cassette comprises MYPBC3, nucleotides encoding a protease recognition site (e.g., TEV protease recognition site) positioned between nucleotides encoding C7 domain and C8 domain, and nucleotides encoding SpyTag positioned in between nucleotides encoding C7 domain and C8 domain (the nucleotides encoding the protease recognition site are 5' to the nucleotides encoding SpyTag); isolating myocytes from the host; introducing to the myocytes a protease that cleaves the first cMyBP-C protein at the protease recognition site to remove its N-terminus; and introducing an N-terminus of cMyBP-C comprising a SpyCatcher peptide C-terminal to the N-terminus of cMyBP-C, wherein the SpyCatcher peptide binds to SpyTag on the first recombinant cMyBP-C to produce a second recombinant cMyBP-C protein.

The present invention features methods of producing a recombinant cMyBP-C protein. In some embodiments, the method comprises introducing into a genome of a host a cassette for expressing a first recombinant cMyBP-C, the first recombinant cMyBP-C being a cMyBP-C peptide with an insertion therein, the insertion comprising a protease recognition site (e.g., TEV protease recognition site or other appropriate protease recognition site) adjacent to and 5' to a SpyTag peptide; isolating myocytes from the host; introducing to the myocytes a protease that cleaves the first cMyBP-C protein at the protease recognition site to remove its N-terminus and expose the SpyTag peptide; introducing a recombinant cMyBP-C N-terminus, the recombinant cMyBP-C N-terminus being at least a portion of cMyBP-C with a SpyCatcher peptide at its C-terminus. The SpyCatcher peptide of the cMyBP-C N-terminus binds to the SpyTag peptide of the first recombinant cMyBP-C to produce a second recombinant cMyBP-C protein. In some embodiments, the host is a mouse. The second recombinant cMyBP-C protein has at least one modified amino acid compared to wild type cMyBP-C.

For the embodiments herein, in some embodiments, the insertion is within or between C7 and C8 domains of cMyBP-C. In some embodiments, the insertion is within or between C2 and C3 domains of cMyBP-C. In some embodiments, the insertion is within or between C3 and C4 domains of cMyBP-C. In some embodiments, the insertion is within or between C4 and C5 domains of cMyBP-C. In some embodiments, the insertion is within or between C5 and C6 domains of cMyBP-C. In some embodiments, the insertion is within or between C6 and C7 domains of cMyBP-C. In some embodiments, the insertion is in between residues VQEILQR (SEQ ID NO: 25) in domain C7 and residues PRLQLPRH (SEQ ID NO: 26) of domain C8 of cMyBP-C. In some embodiments, the insertion is within or between C2 and C8 domains of cMyBP-C.

The present invention also features recombinant proteins comprising cMyBP-C with an insertion therein, the insertion comprises at least a SpyTag peptide adjacent to a protease recognition site. In some embodiments, the protease recognition site is a TEV protease recognition site.

The present invention also features motility assay platforms. In certain embodiments, the assay platform comprises a coverslip with a thick filament disposed thereon, wherein the thick filament comprises a recombinant cMyBP-C protein. The recombinant cMyBP-C protein is produced according to the methods of the present invention. As an example, the thick filaments may be adhered to a SigmaCote-treated (SigmaAldrich) glass coverslip. In some embodiments, the recombinant cMyBP-C protein has at least one modified amino acid compared to wild type cMyBP-C.

The present invention also features nucleic acid sequences encoding cMyBP-C proteins, e.g., recombinant cMyBP-C proteins, etc. In certain embodiments, the nucleic acid sequence comprises MYPBC3, nucleotides encoding a protease recognition site (e.g., TEV protease recognition site) positioned between nucleotides encoding C7 domain and C8 domain, and nucleotides encoding SpyTag positioned in between nucleotides encoding C7 domain and C8 domain (the nucleotides encoding the protease recognition site being 5' to the nucleotides encoding SpyTag).

The present invention also features recombinant proteins, e.g., cMyBP-C recombinant proteins. In certain embodiments, the recombinant protein comprises cMyBP-C with a protease recognition site (e.g., TEV protease recognition site) and a SpyTag peptide positioned in between domain C7 and C8. In certain embodiments, the recombinant protein comprises cMyBP-C with a protease recognition site (e.g., TEV protease recognition site) and a SpyTag peptide positioned in an insertion site in the protein. The insertion site is not limited to a site between domain C7 and domain C8.

The present invention also features genetically engineered hosts (e.g., mice) expressing a recombinant cMyBP-C protein. In some embodiments, the host (e.g., mouse) expresses a recombinant cMyBP-C protein comprising cMyBP-C with a protease recognition site (e.g., TEV protease recognition site) and a SpyTag peptide positioned in between domain C7 and C8. In certain embodiments, the genetically engineered mouse expresses a recombinant cMyBP-C protein with a protease recognition site (e.g., TEV protease recognition site) and SpyTag peptide position in an insertion site in the protein. The insertion site is not limited to between domains C7 and C8. In certain embodiments, the protease recognition site is N-terminal to the SpyTag peptide. In certain embodiments, the protease recognition site is positioned directly next to the SpyTag peptide.

The present invention also features methods of evaluating a mutation in cMyBP-C. In certain embodiments, the method comprises producing a thick filament expressing a recombinant cMyBP-C peptide according to the present invention, wherein the recombinant cMyBP-C has at least one modification compared to wild type cMyBP-C; attaching the thick filament to a substrate; introducing fluorescently labeled actin filaments to the thick filament on the substrate; and tracking sliding of the actin filaments along the thick filaments. In certain embodiments, if the sliding of the actin filaments is different than that observed using thick filaments with wild type cMyBP-C, then at least one modification in the recombinant cMyBP-C has an impact on actin filament sliding. In certain embodiments, the thick filament is obtained from a host (e.g., mouse) in which the recombinant cMyBP-C is expressed. In certain embodiments, the thick filament is obtained from permeabilized myocytes derived from the host (e.g., mouse) in which the recombinant cMyBP-C is expressed.

The present invention also features methods of evaluating effects of a drug. In some embodiments, the method comprises producing a thick filament expressing a recombinant cMyBP-C peptide according to the present invention, wherein the recombinant cMyBP-C has at least one modification compared to wild type cMyBP-C; attaching the thick filament to a substrate; introducing fluorescently labeled actin filaments to the thick filament on the substrate; introducing a drug to the thick filament on the substrate; and tracking sliding of the actin filaments along the thick filaments. In certain embodiments, if the sliding of the actin filaments is different than that observed when a control is introduced to the thick filament on the substrate in lieu of the drug, then the drug has an impact on actin filament sliding. In some embodiments, the thick filament is obtained from a host in which the recombinant cMyBP-C is expressed. In some embodiments, the thick filament is obtained from permeabilized myocytes derived from the host in which the recombinant cMyBP-C is expressed.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1. Shows a schematic view of the structure of cMyBP-C as a series of 11 folded domains (circles) numbered C0-C10 along with the regulatory M-domain between C1 and C2. The M-domain contains 3 cardiac-specific phosphorylation sites known to regulate effects of cMyBP-C in response to inotropic agonists, but 14 additional phosphorylation sites have been identified whose function is unknown. The N'-terminal domains C0-C2 contribute to the regulatory effects of cMyBP-C on contraction in part by binding to the thin filament in a phosphorylation dependent manner. Domains C8-C10 anchor cMyBP-C to the thick filament.

Figure 2:
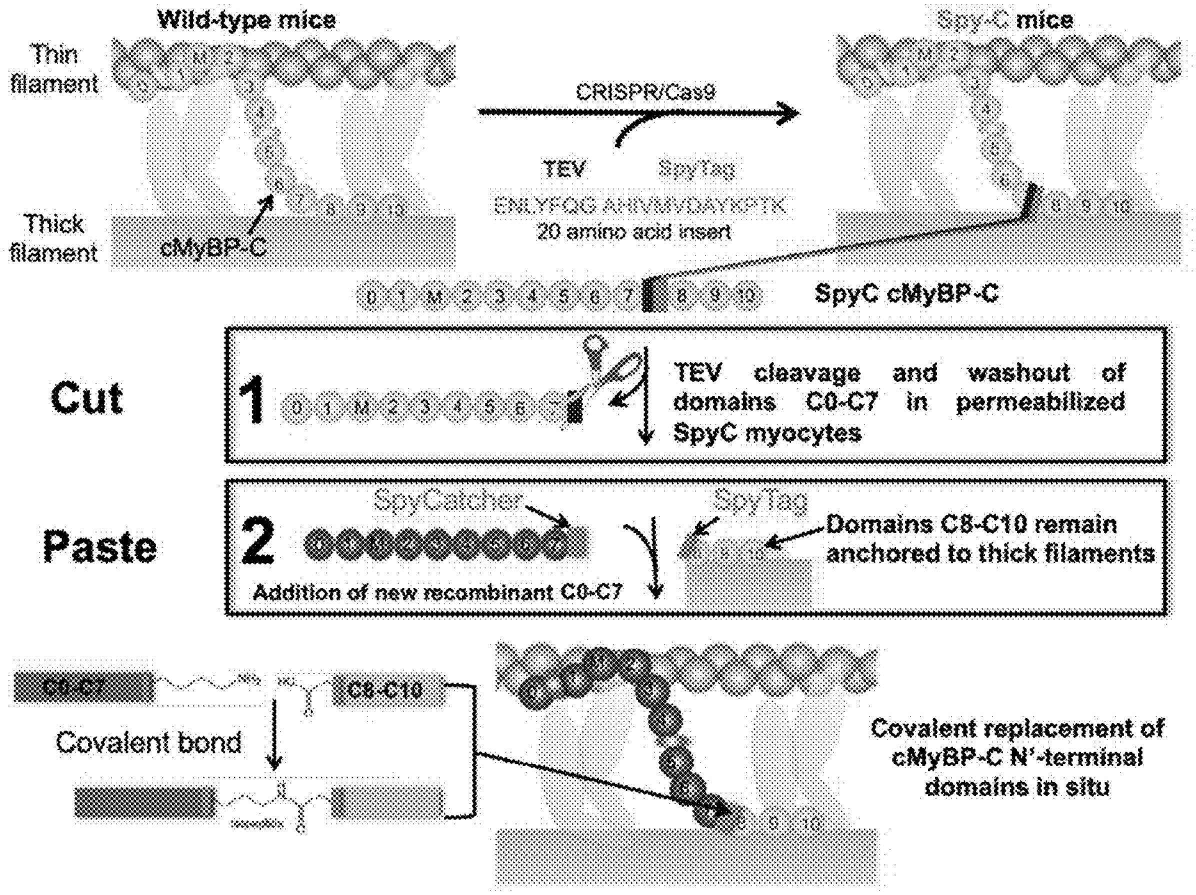

FIG. 2 shows a schematic view of the method of the present invention, e.g., the rapid exchange of cMyBP-C in Spy-C permeabilized myocytes. Spy-C mice express cMyBP-C with a TEV protease recognition site (SEQ ID NO: 12; ENLYFQG) and a SpyTag sequence (SEQ ID NO: 4; AHIVMVDAYKPTK) inserted between domains C7 and C8. (1) TEV cleavage of Spy-C cMyBP-C in permeabilized myocytes first removes domains C0-C7, which (2) are subsequently replaced by new recombinant C0-C7 domains containing desired phosphorylation site mutations (for example, sites in C0, M, and C4). The new C0-C7 domains covalently attach to C8-C10 via the SpyCatcher and SpyTag bond. Because domains C8-C10 remain anchored to the thick filament after TEV cleavage, the Spy-C method efficiently achieves replacement of cMyBP-C in situ.

Figure 3:
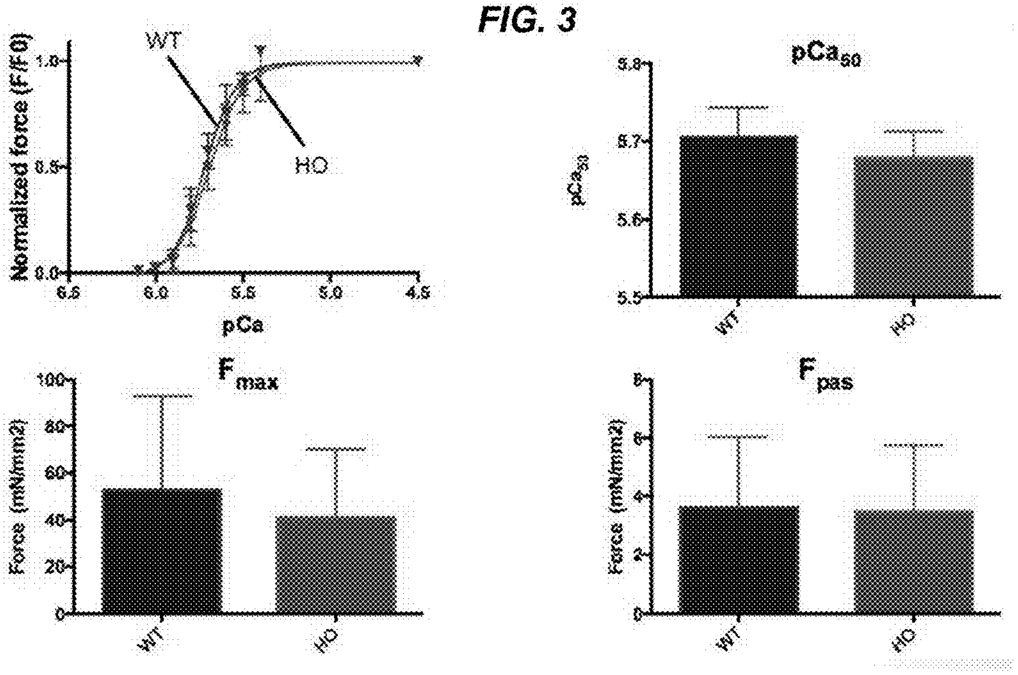

FIG. 3 shows force measurements in cardiomyocytes from wild type (WT) and homozygous (HO) Spy-C mice, demonstrating overtly normal force generation in cardiomyocytes from Spy-C mice. Top left panel shows normal tension-pCa relationships in WT and HO myocytes, while the top right panel shows summary data illustrating that the midpoints of the tension-pCa relationships are not different. Bottom panels show that maximal force ($F_{max}$) and passive tension ($F_{pas}$) also are not different between WT and HO myocytes.

Figure 4:
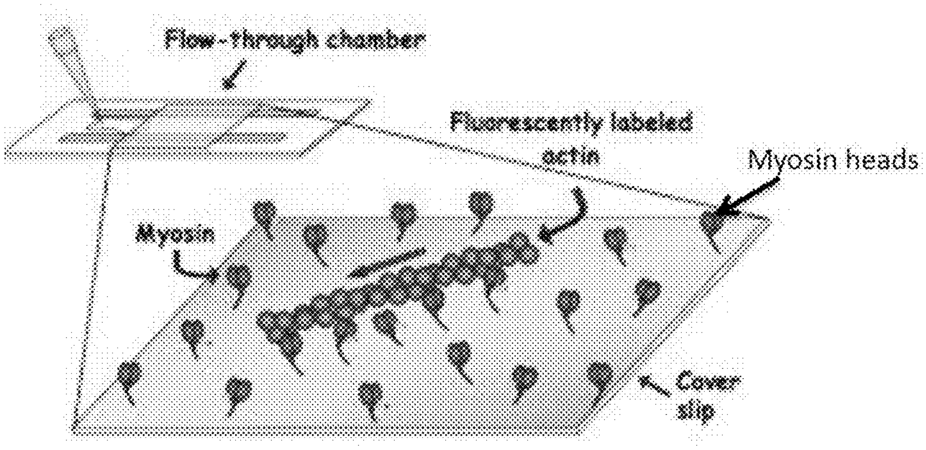
FIG. 4 Prior Art

FIG. 4 shows a typical in vitro motility assay.

Figure 5:
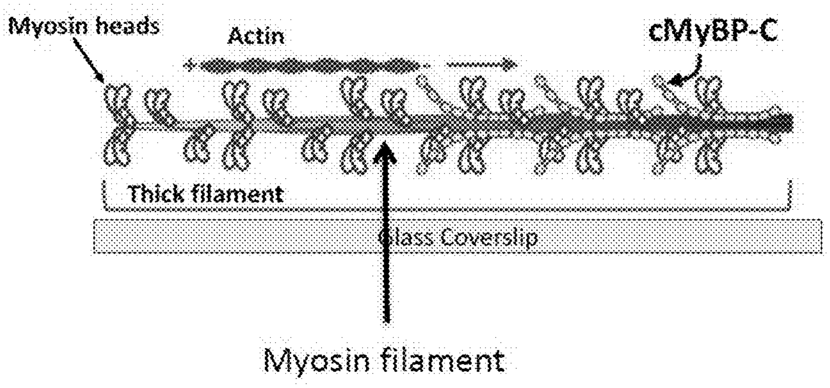

FIG. 5 shows a motility assay using thick filaments, highlighting where cMyBP-C proteins (e.g., recombinant cMyBP-C proteins made using the methods and compositions herein) are located (image source: Previs et al., Science 2012, 337:1215-1218). Myosin molecules are maintained in their native filamentous state. Full-length cMyBP-C can be retained at its proper locations on thick filaments.

Figure 6A:
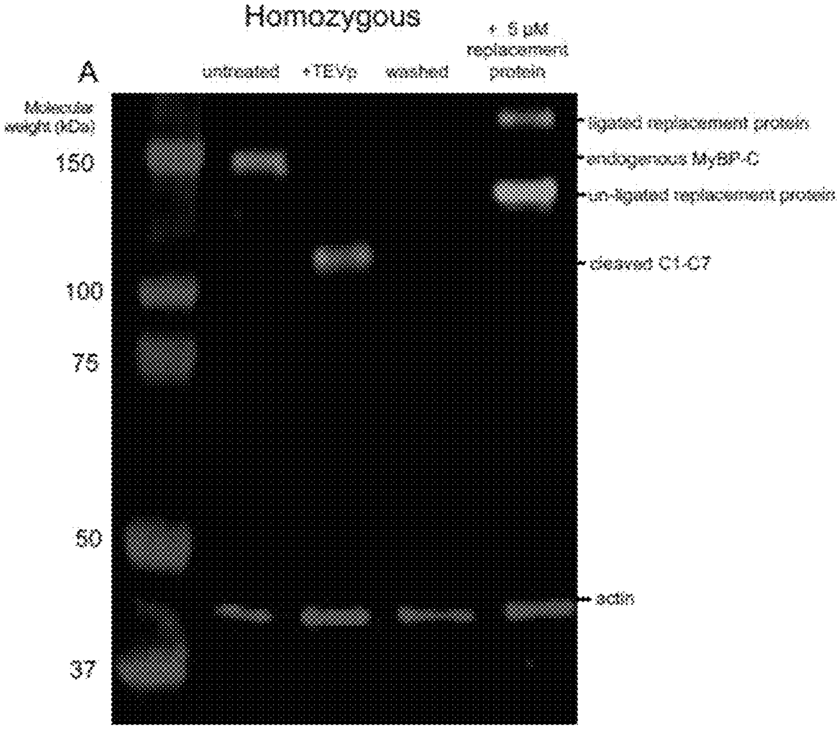
Figure 6B:
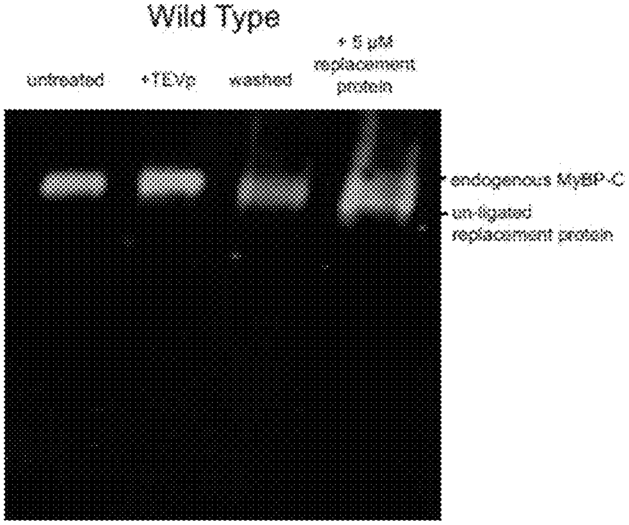

FIGS. 6A and 6B show western blots of detergent-permeabilized soleus myocytes. FIG. 6A shows endogenous MyBP-C domains C1-C7 in homozygous tissue are cleaved with TEV protease (TEVp), shown by a decrease in molecular weight. Cleaved C1-C7 is removed via washing steps and replaced with recombinant replacement SpyCatcher-tagged protein; the resulting upper band is replacement protein ligated to SpyTag in situ, with the size of the SpyCatcher/Tag pair causing an increase in molecular weight relative to endogenous MyBP-C. The lower band is excess (unligated) replacement protein. FIG. 6B shows the size of endogenous MyBP-C in wild type tissue is unaffected by TEVp, washing and addition of replacement protein. Endogenous and replacement MyBP-C detected by anti-MYBPC1 rabbit polyclonal antibody (Novus Biologicals) and fluorescent goat anti-rabbit secondary antibody (LICOR) at 800 nm. Actin, as a loading control, detected by anti-pan actin mouse monoclonal antibody (Invitrogen) and fluorescent goat anti-mouse secondary antibody (LICOR) at 680 nm.

TERMS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise.

Suitable methods and materials for the practice and/or testing of embodiments of the disclosure are described below. Such methods and materials are illustrative only and are not intended to be limiting. Other methods and materials similar or equivalent to those described herein can be used.

For example, conventional methods well known in the art to which the disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999*, Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique,* $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.), the disclosures of which are incorporated in their entirety herein by reference.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

CRISPR/Cas9: A genome editing tool that enables the editing of parts of the genome by removing, adding, or altering sections of the DNA sequence. Cas9 is an enzyme that acts as a pair of molecular scissors to cut the two strands of DNA at a specific location in the genome so that other DNA can be added or removed. Guide RNA (gRNA) is a small piece of pre-designed RNA located within a longer RNA scaffold. The scaffold part binds to DNA and the pre-designed sequence guides Cas9 to the right part of the genome. The gRNA has a sequence that is complementary to the target DNA sequence. After the DNA is cut, the cell recognizes the DNA damage and tries to repair it. The DNA repair machinery can be used to introduce changes to the gene.

Modification: Changes to a protein sequence, structure, etc., or changes to a nucleic acid sequence, etc. As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well.

Recombinant nucleic acid: A nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Recombinant protein: For a recombinant nucleic acid, see "Recombinant Nucleic Acid" above. A recombinant protein or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. Recombinant proteins may be made in cells transduced, transfected, or transformed with genetic elements to direct the synthesis of the heterologous protein. They may also be made in cell-free systems.

DETAILED DESCRIPTION OF THE INVENTION

The present invention features methods and compositions for rapidly replacing MyBP-C (e.g. cMyBP-C) in its normal position in sarcomeres. The methods herein feature the use of a gene-edited mouse model platform that allows for rapid exchange of new combinations of modified or mutant cMyBP-C, such as phosphorylation site mutants, insertions, deletions, fluorescent probes, etc.

Split Peptide Pairs

The present invention features the use of a split peptide pair, e.g., a pair of peptides derived from the splitting of a protein into two halves, each with reactive residues. The split peptide pair is engineered to recombine and form covalent bonds (irreversible isopeptide linkages), thereby creating a new fusion protein. A non-limiting example of a split peptide pair includes SpyCatcher/SpyTag or SnoopCatcher/SnoopTag. Both SpyCatcher/SpyTag and SnoopCatcher/SnoopTag are well known to one of ordinary skill in the art. SpyTag and SpyCatcher were generated by splitting the CnaB2 domain from the fibronectin-binding protein FbaB from *Streptococcus pyogenes* (Spy). CnaB2 was split into a 13 residue peptide (SpyTag) and the 116 residue complementary domain (SpyCatcher). These two parts spontaneously reconstitute to form an isopeptide bond under a range of temperatures, pH values, buffers, and even with non-ionic detergents. SpyTag and SpyCatcher function well when fused at either the N-terminus or C-terminus (see Zakeri et al., PNAS 2012, 109:E690-697; Reddington and Howarth, Current Opinion in Chemical Biology 2015, 29:94-99. SpyCatcher/SpyTag has been used previously to create genetic fusions including several platform technologies such as synthetic vaccine production and catalytic circulation).

SnoopTag and SnoopCatcher were generated by splitting the D4 domain from the pilus associated adhesin protein RrgA. D4 was split into a 15 residue peptide (SnoopTag) and the 134 complementary domain (SnoopCatcher). These two parts spontaneously reconstitute to form an isopeptide bond under a range of temperatures, pH values, buffers, and even with non-ionic detergents. SnoopTag and SnoopCatcher function well when fused at either the N-terminus or C-terminus (see Veggiani et al., PNAS 2016, DOI: 10.1073/pnas.1519214113).

As used in the present invention. The SpyCatcher and SpyTag pair form a spontaneous isopeptide bond between a reactive lysine of SpyCatcher and a reactive aspartate of SpyTag when each half of the pair is expressed as a fusion protein with cMyBP-C. The present invention is not limited to SpyCatcher/SpyTag. Any appropriate split peptide pair that is currently available or that may be developed in the future may be contemplated. For example, in certain embodiments, the split peptide pair is Snoopcatcher/SnoopTag.

Table 1 shows non-limiting examples of sequences for the split protein pairs described herein (e.g., SpyTag, SpyCatcher, SnoopTag, and SnoopCatcher).

Spy-C Method

In the present invention, the SpyCatcher/SpyTag technology was applied to genetically engineered mice (see FIG. 2). Spy-C mice were created using CRISPR/Cas9 gene editing to introduce a protease recognition site (e.g., tobacco etch virus (TEV) protease recognition site, FIG. 2) and a SpyTag sequence (FIG. 2) in the linker between domains C7 and C8 of cMyBP-C. The protease recognition site allows a portion (e.g., the N-terminus) of cMyBP-C to be cut and removed, and the SpyTag sequence allows another peptide with a SpyCatcher sequence to be attached to the remaining portion of cMyBP-C. Note that TEV is highly specific for a consensus sequence. The sequence is rare in mammalian proteins.

To achieve rapid exchange of cMyBP-C in permeabilized myocytes, Spy-C cMyBP-C was cleaved at the TEV site. Domains C0-C7 of Spy-C cMyBP-C were then readily washed out and replaced with novel recombinant cMyBP-C-SpyCatcher containing desired phosphorylation site mutations by adding proteins directly to the bath surrounding the

| Description | Sequence | SEQ NO ID: |
|---|---|---|
| SpyCatcher (nucleotides) | agcggtgatagcgcgacccacattaaatttagcaagcgtgacgaggatggtaaaga<br>actggcgggcgcgaccatggaactgcgtgacagcagcggcaagaccatcagcac<br>ctggattagcgatggtcaggttaaagacttctacctgtatccgggcaagtacacctttgt<br>ggaaaccgcggcgccggatggttatgaggtggcgaccgcgatcaccttcaccgtta<br>acgagcagggtcaagttaccgtgaacggtaaagcgaccaagggc | 1 |
| SpyCatcher protein | SGDSATHIKFSKRDEDGKELAGATMELRDSSGKTISTWISDG<br>QVKDFYLYPGKYTFVETAAPDGYEVATAITFTVNEQGQVTVN<br>GKATKG | 2 |
| SpyTag (nucleotides) | cgcccacatcgtgatggtcgacgcctacaagcccaccaag | 3 |
| SpyTag protein | AHIVMVDAYKPTK | 4 |
| SnoopCatcher (nucleotides) | atgggcagcagccatcatcatcatcatcacagcagcggcctggtgccgcgcggcag<br>ccatatgaagccgctgcgtggtgccgtgtttagcctgcagaaacagcatcccgactat<br>cccgatatctatggcgcgattgatcagaatgggacctatcaaaatgtgcgtaccggcg<br>aagatggtaaactgacctttaagaatctgagcgatggcaaatatcgcctgtttgaaaat<br>agcgaacccgctggctataaaccggtgcagaataagccgattgtggcgtttcagattg<br>tgaatggcgaagtgcgtgatgtgaccagcattgtgccgcaggatattccggctacatat<br>gaatttaccaacggtaaacattatatcaccaatgaaccgataccgccgaaataataa | 5 |
| SnoopCatcher protein | MGSSHHHHHHSSGLVPRGSHMKPLRGAVFSLQKQHPDYPD<br>IYGAIDQNGTYQNVRTGEDGKLTFKNLSDGKYRLFENSEPAG<br>YKPVQNKPIVAFQIVNGEVRDVTSIVPQDIPATYEFTNGKHYIT<br>NEPIPPK | 6 |
| SnoopTag (nucleotides) | ggcggagaacctgtacttccagggcaagctgggcgacatcgagttcatcaaggtga<br>acaagggctac | 7 |
| SnoopTag protein | GKLGDIEFIKVNKGY | 8 |

Table 2 shows Non-limiting examples of TEV protease consensus recognition site

| Description | Sequence | SEQ NO ID: |
|---|---|---|
| TEV Protease recognition site | gagaatctgtatttccagggt | 9 |
| TEV Protease recognition site | E-Xaa-Xaa-Y-Xaa-Q-G<br>where Xaa is any naturally occurring amino acid. | 10 |
| TEV Protease recognition site | E-Xaa-Xaa-Y-Xaa-Q-S<br>where Xaa is any naturally occurring amino acid. | 11 |
| TEV Protease recognition site | ENLYFQG | 12 |

permeabilized myocytes. Added C0-C7-SpyCatcher (FIG. 2) formed a permanent covalent bond with SpyTag (FIG. 2) encoded at the beginning of domains C8-C10. Domains C8-C10 remained anchored to the thick filament because these domains contain the major binding sites for myosin and titin and densities attributable to domains C8-C10 are visible in EM reconstructions of isolated thick filaments. Note that other insertion sites may be possible.

By fusing the SpyCatcher sequence to new recombinant cMyBP-C N-terminal sequences, it is possible to reconstitute full-length cMyBP-C at the precise position of native cMyBP-C in the sarcomere. Thus, the present invention provides methods for efficiently cutting and pasting cMyBP-C in situ to introduce virtually any desired modification (e.g., point mutations, FRET probes, etc.) to study cMyBP-C interactions with its binding partners in sarcomeres or to provide recombinant cMyBP-C peptides for various purposes.

It was surprisingly found that the Spy-C mice generated were phenotypically normal. Given the importance of the cMyBP-C protein, it was expected that disruption of the cMyBP-C protein would have deleterious effects that might preclude the usefulness of the mouse model. However, echocardiography demonstrated the Spy-C mice had no overt cardiac phenotype up to 12 months of age in founders or progeny. Further, cMyBP-C expression was normal and cMyBP-C was properly localized in sarcomeres in Spy-C mice. FIG. 3 shows force measurements in wild type and Spy-C mice, demonstrating overtly normal force generation in cardiomyocytes from Spy-C mice. Inventors were also surprised that the protein was not destabilized by the insertion of the TEV protease site and SpyTag between the C7-C8 regions. There is not much known about the C-terminal end of the cMyBP-C protein, so it was not clear if the insertion would work, or where the insertion should be placed.

Snoop-C Method

In the present invention, the SnoopCatcher/SnoopTag technology was applied to genetically engineered mice. Snoop-C mice were created using CRISPR/Cas9 gene editing to introduce a protease recognition site (e.g., tobacco etch virus (TEV) protease recognition site) and a SnoopTag sequence in the linker between domains C7 and C8 of fMyBP-C. The protease recognition site allows a portion (e.g., the N-terminus) of fMyBP-C to be cut and removed, and the SnoopTag sequence allows another peptide with a SnoopCatcher sequence to be attached to the remaining portion of fMyBP-C. Note that TEV is highly specific for a consensus sequence. The sequence is rare in mammalian proteins. SnoopC mice comprising a SnoopTag sequence adjacent to a protease site internally inserted into the fMyBP-C protein have been created. Additionally, homozygous mice are viable.

Myosin Binding Protein C Constructs

In some embodiments, the present invention features a recombinant protein comprising myosin binding protein C (MyBP-C) with an internal insertion therein. In other embodiments, the present invention features a recombinant myosin binding protein C. In further embodiments, the present invention features a recombinant myosin binding protein C with an insertion therein.

The present invention features a recombinant protein comprising myosin binding protein C (MyBP-C) with an internal insertion therein. In some embodiments, the internal insertion comprises at least a portion of a split-protein pair adjacent to a protease recognition site. In some embodiments, the internal insertion is within or between C1 and C8 domains of MyBP-C.

In some embodiments, the myosin binding protein C (MyBP-C) is cardiac myosin binding protein C (cMyBP-C). In some embodiments, the myosin binding protein C (MyBP-C) is fast skeletal myosin binding protein C (fMyBP-C). In other embodiments, the myosin binding protein C (MyBP-C) is slow skeletal myosin binding protein C (sMyBP-C).

In some embodiments, the present invention features a recombinant cardiac myosin binding protein-C. In other embodiments, the present invention features a recombinant cardiac myosin binding protein C (cMyBP-C) with an internal insertion therein.

In some embodiments, the present invention features a recombinant protein comprising a cardiac myosin binding protein C (cMyBP-C) with an internal insertion therein. In other embodiments, the present invention features a recombinant protein comprising a skeletal myosin binding protein C with an internal insertion therein. In some embodiments, the present invention features a recombinant protein comprising fast skeletal myosin binding protein C (fMyBP-C) with an internal insertion therein. In other embodiments, the present invention features a recombinant protein comprising slow skeletal myosin binding protein C (sMyBP-C) with an internal insertion therein.

In some embodiments, the internal insertion comprises at least a portion of a SpyTag peptide adjacent to a protease recognition site. In other embodiments, the internal insertion comprises at least a portion of a SnoopTag peptide adjacent to a protease recognition site. In some embodiments, the internal insertion comprises at least a portion of a SpyCatcher peptide adjacent to a protease recognition site. In other embodiments, the internal insertion comprises at least a portion of a SnoopCatcher peptide adjacent to a protease recognition site.

In some embodiments, the internal insertion comprises at least a SpyTag peptide adjacent to a protease recognition site. In other embodiments, the internal insertion comprises at least a SnoopTag peptide adjacent to a protease recognition site. In some embodiments, the internal insertion comprises at least a SpyCatcher peptide adjacent to a protease recognition site. In other embodiments, the internal insertion comprises at least a SnoopCatcher peptide adjacent to a protease recognition site.

In some embodiments, the portion of the split protein pair is a SpyTag. In other embodiments, the portion of the split protein pair is a SnoopTag. In some embodiments, the portion of the split-protein pair is capable of self-complementation with a polypeptide corresponding to a second portion of the split protein pair. In some embodiments, the second portion of the split protein pair is a SpyCatcher. In other embodiments, the second portion of the split protein pair is a SnoopCatcher.

For the embodiments herein, in some embodiments, the insertion is within or between C7 and C8 domains of MyBP-C. In some embodiments, the insertion is within or between C0 and C1 domains of MyBP-C. In some embodiments, the insertion is within or between C1 and C2 domains of MyBP-C. In some embodiments, the insertion is within or between C2 and C3 domains of MyBP-C. In some embodiments, the insertion is within or between C3 and C4 domains of MyBP-C. In some embodiments, the insertion is within or between C4 and C5 domains of MyBP-C. In some embodiments, the insertion is within or between C5 and C6 domains of MyBP-C. In some embodiments, the insertion is within or between C6 and C7 domains of MyBP-C.

In some embodiments, the insertion is within or between C0 and C8 domains of MyBP-C. In some embodiments, the insertion is within or between C0 and C7 domains of MyBP-C. In some embodiments, the insertion is within or between C0 and C6 domains of MyBP-C. In some embodiments, the insertion is within or between C0 and C5 domains of MyBP-C. In some embodiments, the insertion is within or between C0 and C4 domains of MyBP-C. In some embodiments, the insertion is within or between C0 and C3 domains of MyBP-C. In some embodiments, the insertion is within or between C0 and C2 domains of MyBP-C.

For the embodiments herein, in some embodiments, the insertion is within or between C7 and C8 domains of cMyBP-C. In some embodiments, the insertion is within or between C0 and C1 domains of cMyBP-C. In some embodiments, the insertion is within or between C1 and C2 domains of cMyBP-C. In some embodiments, the insertion is within or between C2 and C3 domains of cMyBP-C. In some embodiments, the insertion is within or between C3 and C4 domains of cMyBP-C. In some embodiments, the insertion is within or between C4 and C5 domains of cMyBP-C. In some embodiments, the insertion is within or between C5 and C6 domains of cMyBP-C. In some embodiments, the insertion is within or between C6 and C7 domains of cMyBP-C. In some embodiments, the insertion is in between residues VQEILQR (SEQ ID NO: 25) in domain C7 and residues PRLQLPRH (SEQ ID NO: 26) of domain C8 of cMyBP-C.

In some embodiments, the insertion is within or between C0 and C8 domains of cMyBP-C. In some embodiments, the insertion is within or between C0 and C7 domains of cMyBP-C. In some embodiments, the insertion is within or between C0 and C6 domains of cMyBP-C. In some embodiments, the insertion is within or between C0 and C5 domains of cMyBP-C. In some embodiments, the insertion is within or between C0 and C4 domains of cMyBP-C. In some embodiments, the insertion is within or between C0 and C3 domains of cMyBP-C. In some embodiments, the insertion is within or between C0 and C2 domains of cMyBP-C.

In some embodiments, the present invention features a recombinant fast skeletal myosin binding protein-C (fMyBP-C) or a recombinant slow skeletal myosin binding protein C (sMyBP-C). In other embodiments, the present invention features a recombinant recombinant fast skeletal myosin binding protein-C (fMyBP-C) or a recombinant slow skeletal myosin binding protein C (sMyBP-C) with an internal insertion therein.

For the embodiments herein, in some embodiments, the insertion is within or between C7 and C8 domains of fMyBP-C or sMyBP-C. In some embodiments, the insertion is within or between C1 and C2 domains of fMyBP-C or sMyBP-C. In some embodiments, the insertion is within or between C2 and C3 domains of fMyBP-C or sMyBP-C. In some embodiments, the insertion is within or between C3 and C4 domains of fMyBP-C or sMyBP-C. In some embodiments, the insertion is within or between C4 and C5 domains of fMyBP-C or sMyBP-C. In some embodiments, the insertion is within or between C5 and C6 domains of fMyBP-C or sMyBP-C. In some embodiments, the insertion is within or between C6 and C7 domains of fMyBP-C or sMyBP-C. In some embodiments, the insertion is within or between C1 and C8 domains of fMyBP-C or sMyBP-C.

In some embodiments, the insertion is within or between C0 and C8 domains of fMyBP-C or sMyBP-C. In some embodiments, the insertion is within or between C0 and C7 domains of fMyBP-C or sMyBP-C. In some embodiments, the insertion is within or between C0 SEQ ID no; and C6 domains of fMyBP-C or sMyBP-C. In some embodiments, the insertion is within or between C0 and C5 domains of fMyBP-C or sMyBP-C. In some embodiments, the insertion is within or between C0 and C4 domains of fMyBP-C or sMyBP-C. In some embodiments, the insertion is within or between C0 and C3 domains of fMyBP-C or sMyBP-C. In some embodiments, the insertion is within or between C0 and C2 domains of fMyBP-C or sMyBP-C. In some embodiments, the insertion is in between residues PVTIREIVEQ (SEQ ID NO: 27) in domain C7 and residues PKIRLPRHL (SEQ ID NO: 28) of domain C8 of fMyBP-C.

Table 3 shows non-limiting examples of sequences encoding MyBP-C nucleotides and proteins:

| Description | Sequence | SEQ ID NO: |
|---|---|---|
| cMyBP-C (nucleotides) | atgccggagccagggaagaaaccagtgtcagccttcaacaagaagccaaggtcagcgga<br>ggtgaccgctggcagtgctgccgtgttcgaggctgggacggagcggtcaggcgtgaaggtg<br>cggtggcagcgggatggcagcgacatcaccgccaatgacaagtatggtttggcagcagag<br>ggcaagcgacacacactgacagtgcgggatgcgagccctgatgaccagggttcctacgcg<br>gtcattgcaggctcctcaaaggtcaagtttgacctcaaggtcacagagccagcccctccaga<br>gaaggcagaatctgaagttgctccaggagcccccaaagaagtccctgctccagccactgag<br>ttggaagaaagtgtctcaagtcctgaagggtcagtctcggtaacccaggatggctcagctgca<br>gagcatcagggagcccctgatgaccctattggcctctttctgatgcgaccacaggatggtgag<br>gtgaccgtgggcggcagcattgtcttctcagcccgagtggctggggccagcctcctgaaacc<br>gcctgtggtcaagtggttcaagggcaagtgggtggacctgagcagcaaagtgggccagca<br>cctgcagctgcatgacagctatgacagagccagcaaggtctacttgtttgagttgcacatcac<br>agatgctcagaccacttctgctgggggctaccgctgtgaggtgtctaccaaggacaaatttga<br>cagctgtagcttcaacctcactgtccatgaggccattggttctggagacctggacctcagatca<br>gctttccgacgcacgagcctggcgggagcaggtcggagaaccagtgacagccatgaagat<br>gctgggactctggactttagttccctgctgaagaagagagacagtttccggagggactcaaa<br>gctggaggcacctgctgaagaagacgtgtgggagatcctgagacaggcaccgccgtcaga<br>atatgagcgcatcgccttccagcacggagtcacagaccttcgaggcatgctgaagaggctc<br>aagggcatgaagcaggatgaaaagaagagcacagcctttcagaagaagctggagcctgc<br>ctaccaggtaaacaagggccacaagattcggcttactgtggaactggctgatccggacgcc<br>gaagtcaagtggcttaagaatggacaggagatccagatgagtggcagcaagtacatcttcg<br>agtccgtcggtgccaagcgcaccctgaccatcagccagtgctcactggctgacgacgcagc<br>ctaccagtgtgtggtgggggcgagaagtgcagcacggagctctttgtcaaagagcccccg<br>gtgctgatcactcggtccctggaagaccagctggtgatggtgggtcagcgggtggagtttgag<br>tgtgaggtctcagaagaaggggcccaagtcaaatggctgaaggatggggttgaactgacac<br>gtgaggagaccttcaaataccggttcaagaaagatgggcggaaacaccacttgatcatcaa<br>tgaagcaaccctggaggatgcaggacactatgcagtacgcacaagtggaggccagtcact<br>ggctgagctcattgtgcaagagaagaagttggaggtataccaaagcatcgcggacctggca<br>gtgggagccaaggaccaggctgtgtttaagtgtgaggtttcagatgagaatgtacgcggcgtg | 13 |

-continued

| Description | Sequence | SEQ ID NO: |
|---|---|---|
| | tggctgaagaatgggaaggaactggtgcctgacaaccgcataaaggtgtcccatataggcc<br>gggtccacaaactgaccattgacgatgtcacacctgctgatgaggctgactacagctttgtccc<br>tgaagggtttgcctgcaacctgtctgccaagctccacttcatggaggtcaagattgactttgtgc<br>ctaggcaggaacctcccaagatccacttggattgtcccggcagcacaccagacaccattgtg<br>gttgttgctgggaacaagttacgcctggatgtccctatttctggagaccctgctcccactgtggtc<br>tggcagaagactgtaacacaggggaagaaggcctcaactgggccacaccctgatgcccc<br>agaagatgctggtgctgatgaggagtgggtgtttgataagaagctgttgtgtgagactgaggg<br>ccgggtccgggtggagaccaccaaagaccgcagcgtctttacagtcgaaggggcaggga<br>aggaagatgaaggtgtctacacagtcacagtaaagaaccccgtgggcgaggaccaggtc<br>aacctcacagtcaaggtcatcgatgtcccagatgctcctgcggcccctaagatcagcaacgt<br>gggcgaggactcctgcactgtgcagtgggaaccgcctgcctatgatggcgggcagccggtc<br>ctgggatacatcctggagcgcaagaagaaaaagagctacaggtggatgaggctcaactttg<br>atctgctgcgggagctgagccacgaggcgaggcgcatgatcgagggtgtagcctatgagat<br>gcgagtctacgcagtcaatgccgtgggaatgtccaggcccagccctgcctctcagcccttcat<br>gcctattgggcccccctggcgaaccaacccacttggctgtggaggatgtgtcagacaccactgt<br>ctcactcaagtggcggcccccagagcgcgtgggggccggtggcctggacggatacagcgt<br>ggagtactgccaggagggatgctccgagtggacacctgctctgcaggggctgacagagcg<br>cacatcgatgctggtgaaggacctacccactggggcacggctgctgttccgagtacgggcac<br>acaatgtggcaggtcctggaggccctatcgtcaccaaggagcctgtgacagtgcaggagat<br>actgcaacgaccacggctccaactgcccagacacctgcgccagaccatccagaagaaag<br>ttggggagcctgtgaacctcctcatccctttccagggcaaaccccggcctcaggtgacctgga<br>ccaaagaggggcagcccctggcaggtgaggaggtgagcatccggaacagccccacaga<br>cacgatcttgttcatccgagctgcccgccgcacccactcgggcacctaccaggtgacagttcg<br>cattgagaacatggaggacaaggcaacgctgatcctgcagattgtggacaagccaagtcct<br>ccccaggatatccggatcgttgagacttggggtttcaatgtggctctggagtggaagccaccc<br>caagatgatggcaatacagagatctggggttatactgtacagaaagctgacaagaagacca<br>tggagtggttcacggttttggaacactaccgacgcactcactgtgtggtatcagagcttatcattg<br>gcaatggctactacttccgggtcttcagccataacatggtgggttccagtgacaaagctgccg<br>ccaccaaggagccagtctttattccaagaccaggcatcacatatgagccacccaaatacaa<br>ggccctggacttctctgaggccccaagcttcacccagcccttggcaaatcgctccatcattgca<br>ggctataatgccatcctctgctgtgctgtccgaggtagtcctaagcccaagatttcctggttcaa<br>gaatggcctggatctgggagaagatgctcgcttccgcatgttctgcaagcagggagtattgac<br>cctggagatcaggaaaccctgcccctatgatggtggtgtctatgtctgcagggccaccaactt<br>gcagggcgaggcacagtgtgagtgccgcctggaggtgcgagttcctcagtga | |
| cMyBP-C<br>protein | MPEPGKKPVSAFNKKPRSAEVTAGSAAVFEAETERSGVMVRWQR<br>DGSDITANDKYGLAAEGKRHTLTVRDASPDDQGSYAVIAGSSKVK<br>FDLKVTEPAPPEKAESEVAPGAPEEVPAPATELEESVSSPEGSVSV<br>TQDGSAAEHQGAPDDPIGLFLMRPQDGEVTVGGSIVFSARVAGAS<br>LLKPPVVKWFKGKWVDLSSKVGQHLQLHDSYDRASKVYLFELHIT<br>DAQTTSAGGYRCEVSTKDKFDSCNFNLTVHEAIGSGDLDLRSAFR<br>RTSLAGAGRRTSDSHEDAGTPDFSSLLKKRDSFRRDSKLEAPAEE<br>DVWEILRQAPPSEYERIAFQHGVEACHRPLKRLKGMKQDEKKSTA<br>FQKKLEPAYQVNKGHKIRLTVELADPDAEVKWLKNGQEIQMSGSK<br>YIFESVGAKRTLTISQCSLADDAAYQCVVGGEKCSTELFVKEPPVLI<br>TRSLEDQLVMVGQRVEFECEVSEEGAQVKWLKDGVELTREETFK<br>YRFKKDGRKHHLIINEATLEDAGHYAVRTSGGQSLAELIVQEKKLE<br>VYQSIADLAVGAKDQAVFKCEVSDENVRGVWLKNGKELVPDNRIK<br>VSHIGRVHKLTIDDVTPADEADYSFVPEGFACNLSAKLHFMEVKIDF<br>VPRQEPPKIHLDCPGSTPDTIVVVTGNKLRLDVPISGDPAPTVVWQ<br>KTVTQGKKASAGPHPDAPEDAGADEEWVFDKKLLCETEGRVRVE<br>TTKDRSVFTVEGAEKEDEGVYTVTVKNPVGEDQVNLTVKVIDVPD<br>APAAPKISNVGEDSCTVQWEPPAYDGGQPVLGYILERKKKKSYRW<br>MRLNFDLLRELSHEARRMIEGVAYEMRVYAVNAVGMSRPSPASQP<br>FMPIGPPGEPTHLAVEDVSDTTVSLKWRPPERVGAGGLDGYSVE<br>YCQEGCSEWTPALQGLTERRSMLVKDLPTGARLLFRVRAHNVAG<br>PGGPIVTKEPVTVQEILQRPRLQLPRHLRQTIQKKVGEPVNLLIPFQ<br>GKPRPQVTWTKEGQPLAGEEVSIRNSPTDTILFIRAARRTHSGTY<br>QVTVRIENMEDKATLILQIVDKPSPPQDIRIVETWGFNVALEWKPPQ<br>DDGNTEIWGYTVQKADKKTMEWFTVLEHYRRTHCVVSELIIGNGY<br>YFRVFSHNMVGSSDKAAATKEPVFIPRPGITYEPPKYKALDFSEAP<br>SFTQPLANRSIIAGYNAILCCAVRGSPKPKISWFKNGLDLGEDARF<br>RMFCKQGVLTLEIRKPCPYDGGVYVCRATNLQGEAQCECRLEVR<br>VPQ | 14 |
| cMyBP-C<br>C0-07<br>domains<br>(nucleotides) | atgccggagccgggtaaaaagccggttagcgcgttcaacaaaaaaccgcgtagcgcgga<br>agtgaccgcgggtagcgcggcggtgtttgaggcggaaaccgagcgtagcggcgttaaagt<br>gcgttggcaacgtgacggtagcgatattaccgcgaacgataaatacggtctggcggcggaa<br>ggcaagcgtcacaccctgaccgttcgtgatgcgagcccggacgatcagggtagctatgcgg<br>tgatcgcgggcagcagcaaggtgaaatttgacctgaaagttaccgagccggctccgccgga<br>aaaagcggaaagcgaggtggcgccgggtgcgccgaaggaagttccggcgccggcgacc<br>gagctggaggaaagcgtgagcagcccggaaggcagcgttagcgtgacccaggatggtag<br>cgcggcggaacatcaaggtgcgccggatgatccgatcggtctgttcctgatgcgtccgcaag<br>acggtgaggttaccgtgggtggcagcattgtgtttagcgcgcgtgttgcgggtgcgagcctgct<br>gaaaccgccggtggttaagtggttcaagggcaaatgggtggatctgagcagcaaagttggtc<br>agcacctgcaactgcacgacagctacgatcgtgcgagcaaggtttacctgttcgaactgcac | 15 |

-continued

| Description | Sequence | SEQ ID NO: |
|---|---|---|
| | attaccgatgcgcagaccaccagcgcgggtggctaccgttgcgaggttagcaccaaggac<br>aaattcgatagctgcaactttaacctgaccgtgcacgaagcgatcggtagcggcgacctgga<br>tctgcgtagcgcgtttcgtcgtaccagcctggcgggtgcgggtcgtcgtaccagcgacagcca<br>tgaggatgcgggcaccctggatttcagcagcctgctgaagaaacgtgatagctttcgtcgtga<br>cagcaaactggaagcgccggcggaggaagacgtttgggagatcctgcgtcaagctccgcc<br>gagcgaatacgagcgtattgcgttccagcacggtgtgaccgatctgcgtggcatgctgaagc<br>gtctgaagggtatgaagcaggacgaaaagaaaagcaccgcgtttcagaagaaactggag<br>ccggcgtatcaagtgaacaaaggccacaagatccgtctgaccgtggaactggcggacccg<br>gatgcggaagtgaaatggctgaagaacggccaggaaatccaaatgagcggtagcaaata<br>cattttcgagagcgttggtgcgaagcgtaccctgaccattagccaatgcagcctggcggacg<br>atgcggcgtatcagtgcgtggttggtggcgagaaatgcagcaccgaactgttcgtgaaggag<br>ccgccggttctgatcacccgtagcctggaagatcagctggttatggtgggtcaacgtgtggaat<br>ttgagtgcgaagttagcgaggaaggcgcgcaagtgaaatggctgaaggacggtgttgagct<br>gacccgtgaggaaaccttcaaataccgttttaagaaagatggtcgtaagcaccacctgatcat<br>taacgaagcgaccctggaggatgcgggtcactatgcggttcgtaccagcggtggccagagc<br>ctggcggaactgatcgtgcaagaaaagaaactggaagtgtatcagagcattgcggatctgg<br>cggtgggtgcgaaagaccaggcggtgttcaagtgcgaagttagcgatgagaacgttcgtggt<br>gtgtggctgaaaaacggcaaggagctggttccggacaaccgtatcaaagtgagccacattg<br>gtcgtgttcacaagctgaccatcgacgatgttaccccggcggacgaagcggattatagcttcg<br>tgccggagggctttgcgtgcaacctgagcgcgaaactgcacttcatggaagtgaagatcgac<br>tttgttccgcgtcaggagccgccgaaaattcatctggattgcccgggtagcaccccggacacc<br>attgtggttgtggcgggtaacaaactgcgtctggatgtgccgattagcggcgacccggcgccg<br>accgttgtgtggcagaagaccgtgacccaaggtaagaaagcgagcaccggtccgcaccc<br>ggatgcgccggaggatgcgggtgcggacgaggaatgggttttcgataagaaactgctgtgc<br>gaaaccgaaggccgtgttcgtgtggaaaccaccaaggatcgtagcgtttttaccgtggaggg<br>cgcggagaaagaagacgagggtgtttacaccgttaccgtgaagaacccggtgggtgaaga<br>ccaggttaacctgaccgttaaagttattgatgttccggatgcgccggcggcgccgaagattag<br>caacgtgggtgaagatagctgcaccgttcaatgggagccgccggcgtatgatggtggccag<br>ccggtgctgggctatatcctggagcgtaagaaaaagaaaagctatcgttggatgcgtctgaa<br>cttcgacctgctgcgtgaactgagccacgaggcgcgtcgtatgattgaaggtgttgcgtacga<br>gatgcgtgtttatgcggtgaacgcggttggtatgagccgtccgagcccggcgagccagccgtt<br>tatgccgattggtccgccgggtgaaccgacccacctggcggtggaggacgttagcgatacc<br>accgtgagcctgaaatggcgtccgccggaacgtgttggtgcgggtggcctggatggctacag<br>cgtggaatattgccaagagggctgcagcgaatggaccccggcgctgcagggtctgaccga<br>gcgtaccagcatgctggttaaagacctgccgaccggtgcgcgtctgctgttccgtgtgcgtgcg<br>cataacgttgcgggtccgggtggcccgatcgtgaccaaggaaccggttaccgtgcaggaga<br>tt | |
| cMyBP-C<br>C0-C7<br>domains | MPEPGKKPVSAFNKKPRSAEVTAGSAAVFEAETERSGVKVRWQR<br>DGSDITANDKYGLAAEGKRHTLTVRDASPDDQGSYAVIAGSSKVK<br>FDLKVTEPAPPEKAESEVAPGAPKEVPAPATELEESVSSPEGSVSV<br>TQDGSAAEHQGAPDDPIGLFLMRPQDGEVTVGGSIVFSARVAGAS<br>LLKPPVVKWFKGKWVDLSSKVGQHLQLHDSYDRASKVYLFELHIT<br>DAQTTSAGGYRCEVSTKDKFDSCNFNLTVHEAIGSGDLDLRSAFR<br>RTSLAGAGRRTSDSHEDAGTLDFSSLLKKRDSFRRDSKLEAPAEE<br>DVWEILRQAPPSEYERIAFQHGVTDLRGMLKRLKGMKQDEKKSTA<br>FQKKLEPAYQVNKGHKIRLTVELADPDAEVKWLKNGQEIQMSGSK<br>YIFESVGAKRTLTISQCSLADDAAYQCVVGGEKCSTELFVKEPPVLI<br>TRSLEDQLVMVGQRVEFECEVSEEGAQVKWLKDGVELTREETFK<br>YRFKKDGRKHHLIINEATLEDAGHYAVRTSGGQSLAELIVQEKKLE<br>VYQSIADLAVGAKDQAVFKCEVSDENVRGVWLKNGKELVPDNRIK<br>VSHIGRVHKLTIDDVTPADEADYSFVPEGFACNLSAKLHFMEVKIDF<br>VPRQEPPKIHLDCPGSTPDTIVVVAGNKLRLDVPISGDPAPTVVWQ<br>KTVTQGKKASTGPHPDAPEDAGADEEWVFDKKLLCETEGRVRVE<br>TTKDRSVFTVEGAEKEDEGVYTVTVKNPVGEDQVNLTVKVIDVPD<br>APAAPKISNVGEDSCTVQWEPPAYDGGQPVLGYILERKKKKSYRW<br>MRLNFDLLRELSHEARRMIEGVAYEMRVYAVNAVGMSRPSPASQP<br>FMPIGPPGEPTHLAVEDVSDTTVSLKWRPPERVGAGGLDGYSVE<br>YCQEGCSEWTPALQGLTERTSMLVKDLPTGARLLFRVRAHNVAGP<br>GGPIVTKEPVTVQEI | 16 |
| fMyBP-C<br>(nucleotide) | atgcctgaggctaaaccagcggccaaaaaggcctccaaaggcaaagatgccccaaagg<br>aagcccctgcaaagcagactcctgaagagcccccaaagaggccccacctgaggacca<br>atccccaactgcggaggagcccacaggcatcttcctgaaaaagccggactctgtgtcagtgg<br>agactgggaaagacgcggtgattctggccaaggtgaacgggaaggagctcccaggcaag<br>ccgaccatcaagtggttcaaggggaagtggcaggagctgggcagcaagagcggagcccg<br>gttcatcttcaaggaatctcatgactctaccagcaatgtgtacaccgtggagctccacattggg<br>aaggtggtcctaggggaccgcggggattaccgtctagagatcaaagccaaggatgtctgcg<br>acagctgctcgttcaacgtggatgtggaggcaccccgtcaggactcatccggtcagagcctc<br>gagagcttcaagcgttcgggtgacgggaagtcagaagatgcaggcgagctggatttcagtg<br>gcttgctgaagaagagggaagtagttgaggaggagaagaagaagaagaaagatgatgat<br>gatctgggtatacctccggagatttgggagctcctgaaaggggccaagaagagcgagtacg<br>agaagatcgccttccagtacggcatcactgacctccgtggcatgctgaagcggctcaagaa<br>ggccaaggtggaggtcaagaagagtgcagccttcactaagaagttggacccagcctacca<br>agtagacaggggcaacaagatcaagttggtggtggagatcagtgacccagaccttcctctca<br>agtggttcaagaatggccaggagatcaaaccaagcagcaagtatgtgtttgagaacgttggg | 17 |

-continued

| Description | Sequence | SEQ ID NO: |
|---|---|---|
| | aagaaacgaattcttaccatcaacaagtgcacgctggcggatgatgctgcatatgaggtggc<br>agtccaagatgagaagtgtttcactgaactctttgtcaaagagcccccagtcttgattgtcaccc<br>cactggaggaccagcaggtattcgtaggtgaccgagtggaaatgtcggtagaggtgtcaga<br>agagggtgcacaggttatgtggatgaaagatggtgtggagatgactcgggaggattcctaca<br>aggcgcgctaccgcttcaagaaggacgggaaacggcacatcctcatctactctgatgtggcc<br>caggaggatgggggccgctaccaggtcataaccaatggtggccagtgtgaggctgaactca<br>ttgtggaagagaagcaactggaggtcctgcaggacattgctgacctgacagtgaaggctgc<br>agagcaggctgtgttcaagtgtgaagtgtctgatgagaaggtgacaggcaaatggtacaag<br>aatggcgtggaggtacgacccagcaagaggatcaccatctcccatgtgggcagattccaca<br>agctggtgattgatgacgtccgccctgaggatgagggagactacacattcgtgcccgatggct<br>atgccctatccctctcagccaagctcaacttttggaaatcaaagtggagtacgtacctaagca<br>agagcccccgaagatccacctggactgctcagggaagacctcagataactcaattgttgtgg<br>tggctggaaacaagctgcggctggatgtggccatcacaggggaaccacctcccactgctac<br>ctggctaaggggagatgaggtgttcacagccacagaaggcaggacacacatcgagcaga<br>ggccagactgcagcagctttgtgatcgagagtgcggagcggtcggatgagggccgctacac<br>catcaaagtcaccaatcctgcgggcgaggacgtggcctccattttcctgcgggttgtggatgtt<br>cctgatcctccagaggctgtccgtgtcacctcagttggagaagactgggccattctggtctggg<br>agccacccaagtatgatggaggacagccagtgactgggtacttgatggagcggaagaaga<br>aaggctcccagcgctggatgaagatcaactttgaggtcttcactgacaccacctacgagtcca<br>caaagatgatcgagggcgtcctttatgagatgcgggtcttcgctgtcaacgccattggggtctc<br>acagcccagcatgaacaccaagcccttcatgcccattgctcccacgagtgcaccacaacac<br>ctcaccgtggaggatgtgacggacaccaccaccacacttaagtggagacctccagatcgga<br>ttggtgctggtggcattgatggctacctggtggagtactgcctggagggctctgaggaatgggt<br>accggctaacaaggagccagtggaacgctgtggcttcactgtcaaggatctcccaactgga<br>gccaggatcctcttccgggttgttggggtcaacatcgcagggcgcagtgaaccagccaccct<br>ccttcagccagtcactatcagggagattgttgagcaacctaagatccgccttccccgccatctt<br>cgtcagacttatatccgaaaagttggggaggccctcaacctcgtcatccccttccagggcaag<br>ccccggcctcaggtggtgtggaccaagggtggggctcccttggatacctcccgtgtgaatgtg<br>cggactagtgacttcgacacagtgttcttcgtgcgacaggcggcccgctctgactccggagag<br>tatgagctgagtgtgcagattgaaaacatgaaggacactgctaccatacgcatccgggtcgt<br>ggaaaaggcagggccagcagagaatgtgatggtgaaggaggtgtggggcacaaatgctc<br>tggtggagtggcagccgcccaaggacgacgggaacagtgagatcacaggctactttgtcca<br>gaaggctgacaaaaagaccatggagtggttcaatgtctacgaacacaatcgccacaccag<br>ctgtacggtgtctgacctcattgtgggtaatgagtactacttccgtatcttcagcgagaacatctg<br>cggtctcagtgactcgccaggtgtctccaagaacacagctcgaattctcaagacaggaatca<br>ccttaaaaccactggagtacaaggagcatgatttccggacggctcccaagttcctgaccccg<br>ctgatggaccgggtcgtggtggcgggatataccgcagctctcaactgtgccgtcagaggcca<br>ccctaagccaaaggtggtgtggatgaagaacaagatggaaatccatgaagatcccaaattc<br>ctcataaccaactaccagggcatcctgacactgaacatccgccgaccgtcaccctttgatgca<br>gggacctattcctgccgcgccttcaatgagctgggggaggccctggctgaatgcaaactgga<br>tgtccgagtgccacagtga | |
| fMyBP-C protein | MPEAKPAAKKASKGKDAPKEAPAKQTPEEPPKEAPPEDQSPTAEE<br>PTGIFLKKPDSVSVETGKDAVILAKVNGKELPGKPTIKWFKGKWQE<br>LGSKSGARFIFKESHDSTSNVYTVELHIGKVVLGDRGDYRLEIKAK<br>DVCDSCSFNVDVEAPRQDSSGQSLESFKRSGDGKSEDAGELDFS<br>GLLKKREVVEEEKKKKKDDDDLGIPPEIWELLKGAKKSEYEKIAFQ<br>YGITDLRGMLKRLKKAKVEVKKSAAFTKKLDPAYQVDRGNKIKLVV<br>EISDPDLPLKWFKNGQEIKPSSKYVFENVGKKRILTINKCTLADDAA<br>YEVAVQDEKCFTELFVKEPPVLIVTPLEDQQVFVGDRVEMSVEVS<br>EEGAQVMWMKDGVEMTREDSYKARYRFKKDGKRHILIYSDVAQE<br>DGGRYQVITNGGQCEAELIVEEKQLEVLQDIADLTVKAAEQAVFKC<br>EVSDEKVTGKWYKNGVEVRPSKRITISHVGRFHKLVIDDVRPEDE<br>GDYTFVPDGYALSLSAKLNFLEIKVEYVPKQEPPKIHLDCSGKTSD<br>NSIVVVAGNKLRLDVAITGEPPPTATWLRGDEVFTATEGRTHIEQRP<br>DCSSFVIESAERSDEGRYTIKVTNPAGEDVASIFLRVVDVPDPPEAV<br>RVTSVGEDWAILVWEPPKYDGGQPVTGYLMERKKKGSQRWMKIN<br>FEVFTDTTYESTKMIEGVLYEMRVFAVNAIGVSQPSMNTKPFMPIA<br>PTSAPQHLTVEDVTDTTTTLKWRPPDRIGAGGIDGYLVEYCLEGSE<br>EWVPANKEPVERCGFTVKDLPTGARILFRVVGVNIAGRSEPATLLQ<br>PVTIREIVEQPKIRLPRHLRQTYIRKVGEALNLVIPFQGKPRPQVVW<br>TKGGAPLDTSRVNVRTSDFDTVFFVRQAARSDSGEYELSVQIENM<br>KDTATIRIRVVEKAGPAENVMVKEVWGTNALVEWQPPKDDGNSEI<br>TGYFVQKADKKTMEWFNVYEHNRHTSCTVSDLIVGNEYYFRIFSE<br>NICGLSDSPGVSKNTARILKTGITLKPLEYKEHDFRTAPKFLTPLMD<br>RVVVAGYTAALNCAVRGHPKPKVVWMKNKMEIHEDPKFLITNYQG<br>ILTLNIRRPSPFDAGTYSCRAFNELGEALAECKLDVRVPQ | 18 |
| sMyBP-C (nucleotides) | atgccagaacccactaagaaagaggaaaatgaagtgtccgccccagcccctcccccgga<br>agaatggtctcttggtgagtcacctgctggcggggaagagcaggacaaacagaatgccaa<br>ctcccagctgtccaccctgtttgttgaaaaacctcaaaccggatcggtgaaagttggtgcaaa<br>catcacctttgtagccaaagttagggctgaagatcttcttagaaaacccactgtcaaatggttca<br>aggggaaatggatggatctggccagcaaagccgggaaacacctgcagctgaaggagac<br>cttcgagaggcaaactcgggtatacacattcgagatgcagatcatcaaagccaaagagaac<br>tacgcagggaattataggtgtgaggtcacctacaaggataaatttgacagctgttcgtttgatctt<br>gaagtccatgagtctactgggactactccaaacattgacatcagatctgccttcaaaagaagt | 19 |

-continued

| Description | Sequence | SEQ ID NO: |
|---|---|---|
| | ggagaaggtcaagaggatgcaggggaacttgactttagtggtctcctgaaacgtagggagg<br>tgaagcagcaggaagaggagcctgagatagacgtgtgggagctgctgaaaaatgccaac<br>cccaacgaatacgagaagatcgctttccagtatggcatcaccgacttgcgtggcatgcttaag<br>cggctcaagcgcatgcgcagggtggaaaagaagagcgcagcttttgcaaaaattctcgatc<br>ctgcatatcaggtggataaaggaggcaaagtgagatttgtcgtggagttggcagacccaaaa<br>ctggaggtgaaatggtttaaaaatggccaagagattcgacccagcacaaaatacatctttga<br>gcacaaaggaaacgagagaatcatgtttattaataactgttcgctgacagatgattcggagta<br>ctatgtgacagctggagatgagaaatgttctactgagctctttgtaagagagcctccaatcatg<br>gtgactaagcagctggaagacatgaacgcttactgtggggagagggtagagatggaagttg<br>aggtgtctgaagatgacgccaatgtaaaatggtttaagaatggtgaagagatcttccctggtcc<br>aaagtcaagatacaagattaaagttgaaggcaaaaagcacacgttgatcatagaaggggc<br>aacaaaggctgacagtgcggagtactcagccatgacaaccggggacaatcatctgccaa<br>actcagcgttgacttgagacctctaaagatcacgacgcctctgacggaccagacagtaaaa<br>cttgggaaagaagtatgcttgaagtgtgaaatctctgaaaatgtaccaggaaaatggacaaa<br>aaatggcctccctgttcaggagggtgagcgtctgaaggttgttcacaagggaagaatccaca<br>agttagtcatagccaatgctctcattgaagatgaaggtgaatatgtatttacaccagatgcctac<br>aatgttcctttgtctgccaaagttcatgtcatcgaccctcccaagatcatcctggatggcctggat<br>gctgataacacagtgacagtgatagctggaagcaagcttcgcctggagattcctgtcacagg<br>ggaaccacctcccaaagccatctggagccgagcagataaggctattatggaaggcagtggt<br>cggatcagggcagaatcctaccctgacagcagcacactggtcattgacgtggcagagaga<br>gacgactctggtgtgtacaacataaatctgaaaaatgaggctggagaagcacatgcaagca<br>tcaagattaaggttgtggatatccctgatcctccagtggcaccaaatgtgacagaagtgggag<br>atgactggtgcatcatgaactgggagcctcctgcctatgatggagggtctccaatcttaggata<br>ctttattgagaggaaaaagaaacaaagctccaggtggatgagactgaatttcgatctctgcaa<br>agagacaacttttgagcccaagaagatgattgaaggcgtggcctacgaggtccgaatctttg<br>cggtcaacgccattggcatctccaagcccagtatgccctccaagccctttgttcctttggctgtg<br>accagccctcctactcttctggctgtcgactccgtgactgactcgtctgtgacgatgaagtggag<br>gcccccagatcagattggcgcagcaggtttagatggctatgtgctagagtattgctttgaagga<br>actgaggactggatagttgcaaacacagacctgatcgacaagaccaagttcaccatcaatg<br>gtctgcccacggatgcgaagatctttgtacgtgtgaaggctattaacgcggctggggctagtg<br>agcccaagtactattctcagcccatccttgtgaaggaaatcattgagccaccaaagattcgca<br>tcccaaggcatctgaagcaaacttacatccgcagagtcggagaagctgtcaatctggtgattc<br>cttttcagggtaaaccaagaccagagttgacctggaagaaggacggtgaagaaattgacaa<br>gaatcaaataaacattcgcaactcagaaactgataccatcatattcatccggaaagcagagc<br>ggagccactcgggcaagtacgacctgcaggtcaaagtggataaatacgtggaaaatgcctc<br>tatcgacatccagattgttgaccgtccaggtccaccccagactgtgactattgaagatgtgtgg<br>ggagagaatgttgccctaacatggacaccaccaaaggacgatggaatgctgccatcaca<br>gggtacaccatccagaaggccgacaagaaaagcatggaatggttcaccgtcattgaacatt<br>accaccgaaccaacgccaccattactgagctggtcatagggaacgagtattacttccgggtct<br>ttgctgaaaacatgtgcggccttagcgaggatgcaactatgacgaaggagagtgcagtgatt<br>gccaaggacggtaagatctataaaaatccagtgtacgaagacttcaatttcacagaggcccc<br>catgtttactcaacctttggttaacacctatgccatcgctggttacaatgccaccctgaactgcag<br>cgtccgaggaaatcccaagcccaaaatcacctggatgaaaaacaaagtggctattgtggat<br>gacccaagatacagaatgttcagcaaccaaggagtctgtaccctggagatccgcaagccta<br>gtccttatgacggaggcacgtactgctgcaaagcagtcaatgacctcgggacggtggagatt<br>gaatgcaaactggaggtgaaaggtgggctgtccttctgcaggctcctcctgcaaggcgtgcct<br>ccaaacataattgattcctatttgcgagacttacaatcaagcaatcccgaggaatactgaggg<br>cagggcattgcttctagacacacccactgctttgaaatctgattgaaaatggatagtactttctgg<br>ttttctcccaggcccccaagtgtggtcactttctttctttcctcctaactttgaagaaagt | |
| sMyBP-C protein | MPEPTKKEENEVPAPAPPPEEPSKEKEAGTTPAKDWTLVETPPGE<br>EQAKQNANSQLSILFIEKPQGGTVKVGEDITFIAKVKAEDLLRKPTI<br>KWFKGKWMDLASKAGKHLQLKETFERHSRVYTFEMQIIKAKDNFA<br>GNYRCEVTYKDKFDSCSFDLEVHESTGTTPNIDIRSAFKRSGEGQ<br>EDAGELDFSGLLKRREVKQQEEEPQVDVWELLKNAKPSEYEKIAF<br>QYGITDLRGMLKRLKRMRREEKKSAAFAKILDPAYQVDKGGRVRF<br>VVELADPKLEVKWYKNGQEIRPSTKYIFEHKGCQRILFINNCQMTD<br>DSEYYVTAGDEKCSTELFVREPPIMVTKQLEDTTAYCGERVELECE<br>VSEDDANVKWFKNGEEIIPGPKSRYRIRVEGKKHILIIEGATKADAA<br>EYSVMTTGGQSSAKLSVDLKPLKILTPLTDQTVNLGKEICLKCEISE<br>NIPGKWTKNGLPVQESDRLKVVHKGRIHKLVIANALTEDEGDYVFA<br>PDAYNVTLPAKVHVIDPPKIILDGLDADNTVTVIAGNKLRLEIPISGEP<br>PPKAMWSRGDKAIMEGSGRIRTESYPDSSTLVIDIAERDDSGVYHI<br>NLKNEAGEAHASIKVKVVDFPDPPVAPTVTEVGDDWCIMNWEPPA<br>YDGGSPILGYFIERKKKQSSRWMRLNFDLCKETTFEPKKMIEGVAY<br>EVRIFAVNAIGISKPSMPSRPFVPLAVTSPPTLLTVDSVTDTTVTMR<br>WRPPDHIGAAGLDGYVLEYCFEGSTSAKQSDENGEAAYDLPAED<br>WIVANKDLIDKTKFTITGLPTDAKIFVRVKAVNAAGASEPKYYSQPIL<br>VKEIIEPPKIRIPRHLKQTYIRRVGEAVNLVIPFQGKPRPELTWKKDG<br>AEIDKNQINIRNSETDTIIFIRKAERSHSGKYDLQVKVDKFVETASIDI<br>QIIDRPGPPQIVKIEDVVVGENVALTWTPPKDDGNAAITGYTIQKADK<br>KSMEWFTVIEHYHRTSATITELVIGNEYYFRVFSENMCGLSEDATM<br>TKESAVIARDGKIYKNPVYEDFDFSEAPMFTQPLVNTYAIAGYNATL<br>NCSVRGNPKPKITWMKNKVAIVDDPRYRMFSNQGVCTLEIRKPSP<br>YDGGTYCCKAVNDLGTVEIECKLEVKVIAQ | 20 |

Embodiments herein may comprise whole MyBP-C or a portion of MyBP-C. Whole MyBP-C and a portion thereof is not limited to a wild type or original sequence and may include MyBP-C or a portion thereof with one or more modifications and/or mutations, such as point mutations, deletions, insertions, etc.

Non-limiting examples of sequences encoding modified cMyBP-C proteins are included in Table 4. SEQ ID NO: 21 is a cDNA sequence for wild-type cMyBP-C C0-07 domains with SpyCatcher followed by a TEV recognition site, His Tag, and Stop codon. SEQ ID NO: 21 is used to make C0-C7-sc replacement domains after TEV cleavage of cMyBP-C in myocytes from Spy-C mice. SEQ: ID NO: 2 is a cDNA sequence for cMyBP-C C0-07 domains containing the [E330K] mutation with SpyCatcher followed by a TEV recognition site, His Tag, and Stop codon. SEQ: ID NO: 2 is used to make C0-C7-sc replacement proteins with the specified mutation after TEV cleavage of cMyBP-C in myocytes from Spy-C mice. SEQ ID NO: 23 is a cDNA sequence for cMyBP-C C0-C7 domains containing the [L348P] mutation with SpyCatcher followed by a TEV recognition site, His Tag, and Stop codon. SEQ ID NO: 23 is used to make C0-C7-sc replacement proteins with the specified mutation after TEV cleavage of cMyBP-C in myocytes from Spy-C mice.

| Description | sequence | SEQ ID NO: |
|---|---|---|
| wild-type cMyBP-C C0-07 domains, SpyCatcher, TEV recognition site His Tag, and Stop codon | atgccggagccgggtaaaaagccggttagggcgttcaacaaaaaccgcgtagcgcgg<br>aagtgaccgcgggtagcgcggcggtgtttgaggcggaaaccgagcgtagcggcgttaaa<br>gtgcgttggcaacgtgacggtagcgatattaccgcgaacgataaatacggtctggcggcgg<br>aaggcaagcgtcacaccctgaccgttcgtgatgcgagcccggacgatcagggtagctatg<br>cggtgatcgcgggcagcagcaaggtgaaatttgacctgaaagttaccgagccggctccgc<br>cggaaaaagcggaaagcgaggtggcgccgggtgcgccgaaggaagttccggcgccgg<br>cgaccgagctggaggaaagcgtgagcagcccggaaggcagcgttagcgtgacccagg<br>atggtagggcggcggaacatcaaggtgcgccggatgatccgatcggtctgttcctgatgcgt<br>ccgcaagacggtgaggttaccgtgggtggcagcattgtgtttagcgcgcgtgttgcgggtgc<br>gaggctgctgaaaccgccggtggttaagtggttcaagggcaaatgggtggatctgaggag<br>caaagttggtcagcacctgcaactgcacgacagctaggatcgtgcgaggaaggtttacctg<br>ttcgaactgcacattaccgatgcgcagaccaccagcgcgggtggctaccgttgcgaggtta<br>gcaccaaggacaaattcgatagctgcaactttaacctgaccgtgcacgaagcgatcggta<br>gcggcgacctggatctgcgtagcgcgtttcgtcgtaccagcctggcgggtgcgggtcgtcgt<br>accagcgacagccatgaggatgcgggcaccctggatttcagcagcctgctgaagaaacg<br>tgatagctttcgtcgtgacagcaaactggaagcgccggcggaggaagacgtttgggagat<br>cctgcgtcaagctccgccgagcgaatacgagcgtattgcgttccagcacggtgtgaccgat<br>ctgcgtggcatgctgaagcgtctgaagggtatgaagcaggacgaaaagaaaagcaccg<br>cgtttcagaagaaactggagccggcgtatcaagtgaacaaaggccacaagatccgtctga<br>ccgtggaactggcggacccggatgcggaagtgaaatggctgaagaacggccaggaaat<br>ccaaatgagcggtagcaaatacattttcgagagcgttggtgcgaagcgtaccctgaccatta<br>gccaatgcagcctggcggacgatgcggcgtatcagtgcgtggttggtggcgagaaatgca<br>gcaccgaactgttcgtgaaggagccgccggttctgatcacccgtagcctggaagatcagct<br>ggttatggtgggtcaacgtgtggaatttgagtgcgaagttagcgaggaaggcgcgcaagtg<br>aaatggctgaaggacggtgttgagctgacccgtgaggaaaccttcaaataccgttttaaga<br>aagatggtcgtaagcaccacctgatcattaacgaagcgaccctggaggatgcgggtcact<br>atgcggttcgtaccagcggtggccagagcctggcggaactgatcgtgcaagaaaagaaa<br>ctggaagtgtatcagagcattgcggatctggcggtgggtgcgaaagaccaggcggtgttca<br>agtgcgaagttagcgatgagaacgttcgtggtgtgtggctgaaaaacggcaaggagctggt<br>tccggacaaccgtatcaaagtgagccacattggtcgtgttcacaagctgaccatcgacgat<br>gttaccccggcggacgaagcggattatagcttcgtgccggagggctttgcgtgcaacctga<br>gcgcgaaactgcacttcatggaagtgaagatcgactttgttccgcgtcaggagccgccgaa<br>aattcatctggattgcccgggtagcaccccggacaccattgtggttgtggcgggtaacaaac<br>tgcgtctggatgtgccgattagcggcgacccggcgccgaccgttgtgtggcagaagaccgt<br>gacccaaggtaagaaagcgagcaccggtccgcacccggatgcgccggaggatgcggg<br>tgcggacgaggaatgggttttcgataagaaactgctgtgcgaaaccgaaggccgtgttcgt<br>gtggaaaccaccaaggatcgtagcgtttttaccgtggagggcgcggagaaagaagacga<br>gggtgtttacaccgttaccgtgaagaacccggtgggtgaagaccaggttaacctgaccgtta<br>aagttattgatgttccggatgcgccggcggcgccgaagattagcaacgtgggtgaagatag<br>ctgcaccgttcaatgggagccgccggcgtatgatggtggccagccggtgctgggctatatcc<br>tggagcgtaagaaaaagaaaagctatcgttggatgcgtctgaacttcgacctgctgcgtga<br>actgagccacgaggcgcgtcgtatgattgaaggtgttgcgtacgagatgcgtgtttatgcggt<br>gaacgcggttggtatgagccgtccgagcccggcgagccagccgtttatgccgattggtccg<br>ccgggtgaaccgacccacctggcggtggaggacgttagcgataccaccgtgagcctgaa<br>atggcgtccgccggaacgtgttggtgcgggtggcctggatggctacagcgtggaatattgcc<br>aagagggctgcagcgaatggaccccggcgctgcagggtctgaccgagcgtaccagcat<br>gctggttaaagacctgccgaccggtgcgcgtctgctgttccgtgtgcgtgcgcataacgttgc<br>gggtccgggtggcccgatcgtgaccaaggaaccggttaccgtgcaggagatt[**agcggtg<br>atagcgcgacccacattaaatttagcaagcgtgacgaggatggtaaagaactggcg<br>ggcgcgaccatggaactgcgtgacagcagcggcaagaccatcagcacctggatt<br>agcgatggtcaggttaaagacttctacctgtatccgggcaagtacacctttgtggaaa<br>ccgcggcgccggatggttatgaggtggcgaccgcgatcaccttcaccgttaacga<br>gcagggtcaagttaccgtgaacggtaaagcgaccaagggc**][gagaatctgtatttcc<br>agggt][catcaccaccaccatcac]taa | 21 |

| Description | sequence | SEQ ID NO: |
|---|---|---|
| wild-type cMyBP-C C0-C7 domains containing a [E330K] mutation, SpyCatcher, TEV recoinition site His Tag, and Stop codon | atgccggagccgggtaaaaagccggttagcgcgttcaacaaaaaaccgcgtagcgcgg<br>aagtgaccgcgggtagcgcggcggtgtttgaggcggaaaccgagcgtagcggcgttaaa<br>gtgcgttggcaacgtgacggtagcgatattaccgcgaacgataaatacggtctggcggcgg<br>aaggcaagcgtcacaccctgaccgttcgtgatgcgagcccggacgatcagggtagctatg<br>cggtgatcgcgggcagcagcaaggtgaaatttgacctgaaagttaccgagccggctccgc<br>cggaaaaagcggaaagcgaggtggcgccgggtgcgcccgaaggaagttccggcgccgg<br>cgaccgagctggaggaaagcgtgagcagcccggaaggcagcgttagcgtgacccagg<br>atggtagcgcggcggaacatcaaggtgcgccggatgatccgatcggtctgttcctgatgcgt<br>ccgcaagacggtgaggttaccgtgggtggcagcattgtgtttagcgcgcgtgttgcgggtgc<br>gagcctgctgaaaccgccggtggttaagtggttcaagggcaaatgggtggatctgagcag<br>caaagttggtcagcacctgcaactgcacgacagctacgatcgtgcgagcaaggtttacctg<br>ttcgaactgcacattaccgatgcgcagaccaccagcgcgggtggctaccgttgcgaggtta<br>gcaccaaggacaaattcgatagctgcaactttaacctgaccgtgcacgaagcgatcggta<br>gcggcgacctggatctgcgtagcgcgtttcgtcgtaccagcctggcgggtgcgggtcgtcgt<br>accagcgacagccatgaggatgcgggcaccctggatttcagcagcctgctgaagaaacg<br>tgatagctttcgtcgtgacagcaaactggaagcgccggcggaggaagacgtttgggagat<br>cctgcgtcaagctccgcc[aag]cgaatacgagcgtattgcgttccagcacggtgtgaccga<br>tctgcgtggcatgctgaagcgtctgaagggtatgaagcaggacgaaaagaaaagcaccg<br>cgtttcagaagaaactggagccggcgtatcaagtgaacaaaggccacaagatccgtctga<br>ccgtggaactggcggacccggatgcggaagtgaaatggctgaagaacggccaggaaat<br>ccaaatgagcggtagcaaatacatttttcgagagcgttggtgcgaagcgtaccctgaccatta<br>gccaatgcagcctggcggacgatgcggcgtatcagtgcgtggttggtggcgagaaatgca<br>gcaccgaactgttcgtgaaggagccgccggttctgatcacccgtagcctggaagatcagct<br>ggttatggtgggtcaacgtgtggaatttgagtgcgaagttagcgaggaaggcgcgcaagtg<br>aaatggctgaaggacggtgttgagctgacccgtgaggaaaccttcaaataccgttttaaga<br>aagatggtcgtaagcaccacctgatcattaacgaagcgaccctggaggatgcgggtcact<br>atgcggttcgtaccagcggtggccagagcctggcggaactgatcgtgcaagaaaagaaa<br>ctggaagtgtatcagagcattgcggatctggcggtgggtgcgaaagaccaggcggtgttca<br>agtgcgaagttagcgatgagaacgttcgtggtgtgtggctgaaaaacggcaaggagctggt<br>tccggacaaccgtatcaaagtgagccacattggtcgtgttcacaagctgaccatcgacgat<br>gttaccccggcggacgaagcggattatagcttcgtgccggagggctttgcgtgcaacctga<br>gcgcgaaactgcacttcatggaagtgaagatcgactttgttccgcgtcaggagccgccgaa<br>aattcatctggattgcccgggtagcaccccggacaccattgtggttgtggcgggtaacaaac<br>tgcgtctggatgtgccgattagcggcgacccggcgccgaccgttgtgtggcagaagaccgt<br>gacccaaggtaagaaagcgagcaccggtccgcacccggatgcgccggaggatgcggg<br>tgcggacgaggaatgggttttcgataagaaactgctgtgcgaaaccgaaggccgtgttcgt<br>gtggaaaccaccaaggatcgtagcgtttttaccgtggagggcgcggagaaagaagacga<br>gggtgtttacaccgttaccgtgaagaacccggtgggtgaagaccaggttaacctgaccgtta<br>aagttattgatgttccggatgcgccggcggcgccgaagattagcaacgtgggtgaagatag<br>ctgcaccgttcaatgggagccgccggcgtatgatggtggccagccggtgctgggctatatcc<br>tggagcgtaagaaaaagaaaagctatcgttggatgcgtctgaacttcgacctgctgcgtga<br>actgagccacgaggcgcgtcgtatgattgaaggtgttgcgtacgagatgcgtgtttatgcggt<br>gaacgcggttggtatgagccgtccgagcccggcgagccagccgtttatgccgattggtccg<br>ccgggtgaaccgacccacctggcggtggaggacgttagcgataccaccgtgagcctgaa<br>atggcgtccgccggaacgtgttggtgcgggtggcctggatggctacagcgtggaatattgcc<br>aagagggctgcagcgaatggacccggcgctgcagggtctgaccgagcgtaccagcat<br>gctggttaaagacctgccgaccggtgcgcgtctgctgttccgtgtgcgtgcgcataacgttgc<br>gggtccgggtggcccgatcgtgaccaaggaaccggttaccgtgcaggagatt[**agcggtg**<br>**atagcgcgacccacattaaatttagcaagcgtgacgaggatggtaaagaactggcg**<br>**ggcgcgaccatggaactgcgtgacagcagcggcaagaccatcagcacctggatt**<br>**agcgatggtcaggttaaagacttctacctgtatccgggcaagtacacctttgtggaaa**<br>**ccgcggcgccggatggttatgaggtggcgaccgcgatcaccttcaccgttaacga**<br>**gcagggtcaagttaccgtgaacggtaaagcgaccaagggc**][gagaatctgtatttcc<br>agggt][catcaccaccaccatcac]taa | 22 |
| wild-type cMyBP-C C0-C7 domains containing a [L348P] mutation; SpyCatcher, TEV recognition site His Tag, and Stop codon | atgccggagccgggtaaaaagccggttagcgcgttcaacaaaaaaccgcgtagcgcgg<br>aagtgaccgcgggtagcgcggcggtgtttgaggcggaaaccgagcgtagcggcgttaaa<br>gtgcgttggcaacgtgacggtagcgatattaccgcgaacgataaatacggtctggcggcgg<br>aaggcaagcgtcacaccctgaccgttcgtgatgcgagcccggacgatcagggtagctatg<br>cggtgatcgcgggcagcagcaaggtgaaatttgacctgaaagttaccgagccggctccgc<br>cggaaaaagcggaaagcgaggtggcgccgggtgcgcccgaaggaagttccggcgccgg<br>cgaccgagctggaggaaagcgtgagcagcccggaaggcagcgttagcgtgacccagg<br>atggtagcgcggcggaacatcaaggtgcgccggatgatccgatcggtctgttcctgatgcgt<br>ccgcaagacggtgaggttaccgtgggtggcagcattgtgtttagcgcgcgtgttgcgggtgc<br>gagcctgctgaaaccgccggtggttaagtggttcaagggcaaatgggtggatctgagcag<br>caaagttggtcagcacctgcaactgcacgacagctacgatcgtgcgagcaaggtttacctg<br>ttcgaactgcacattaccgatgcgcagaccaccagcgcgggtggctaccgttgcgaggtta<br>gcaccaaggacaaattcgatagctgcaactttaacctgaccgtgcacgaagcgatcggta<br>gcggcgacctggatctgcgtagcgcgtttcgtcgtaccagcctggcgggtgcgggtcgtcgt<br>accagcgacagccatgaggatgcgggcaccctggatttcagcagcctgctgaagaaacg<br>tgatagctttcgtcgtgacagcaaactggaagcgccggcggaggaagacgtttgggagat<br>cctgcgtcaagctccgccgagcgaatacgagcgtattgcgttccagcacggtgtgaccgat<br>ctgcgtggcatgctgaagcgt[ccg]aagggtatgaagcaggacgaaaagaaaagcacc<br>gcgtttcagaagaaactggagccggcgtatcaagtgaacaaaggccacaagatccgtctg<br>accgtggaactggcggacccggatgcggaagtgaaatggctgaagaacggccaggaa | 23 |

-continued

| Description | sequence | SEQ ID NO: |
|---|---|---|
| | atccaaatgagcggtagcaaatacattttcgagagcgttggtgcgaagcgtaccctgaccat<br>tagccaatgcagcctggcggacgatgcggcgtatcagtgcgtggttggtggcgagaaatgc<br>agcaccgaactgttcgtgaaggagccgccggttctgatcacccgtagcctggaagatcagc<br>tggttatggtgggtcaacgtgtggaatttgagtgcgaagttagcgaggaaggcgcgcaagt<br>gaaatggctgaaggacggtgttgagctgacccgtgaggaaaccttcaaataccgttttaag<br>aaagatggtcgtaagcaccacctgatcattaacgaagcgaccctggaggatgcgggtcac<br>tatgcggttcgtaccagcggtggccagagcctggcggaactgatcgtgcaagaaaagaaa<br>ctggaagtgtatcagagcattgcggatctggcggtgggtgcgaaagaccaggcggtgttca<br>agtgcgaagttagcgatgagaacgttcgtggtgtgtggctgaaaaacggcaaggagctggt<br>tccggacaaccgtatcaaagtgagccacattggtcgtgttcacaagctgaccatcgacgat<br>gttaccccggcggacgaagcggattatagcttcgtgccggagggctttgcgtgcaacctga<br>gcgcgaaactgcacttcatggaagtgaagatcgactttgttccgcgtcaggagccgccgaa<br>aattcatctggattgcccgggtagcaccccggacaccattgtggttgtggcgggtaacaaac<br>tgcgtctggatgtgccgattagcggcgacccggcgccgaccgttgtgtggcagaagaccgt<br>gacccaaggtaagaaagcgagcaccggtccgcacccggatgcgccggaggatgcggg<br>tgcggacgaggaatgggttttcgataagaaactgctgtgcgaaaccgaaggccgtgttcgt<br>gtggaaaccaccaaggatcgtagcgtttttaccgtggagggcgcggagaaagaagacga<br>gggtgtttacaccgttaccgtgaagaacccggtgggtgaagaccaggttaacctgaccgtta<br>aagttattgatgttccggatgcgccggcggcgccgaagattagcaacgtgggtgaagatag<br>ctgcaccgttcaatgggagccgccggcgtatgatggtggccagccggtgctgggctatatcc<br>tggagcgtaagaaaaagaaaagctatcgttggatgcgtctgaacttcgacctgctgcgtga<br>actgagccacgaggcgcgtcgtatgattgaaggtgttgcgtacgagatgcgtgtttatgcggt<br>gaacgcggttggtatgagccgtccgagcccggcgagccagccgtttatgccgattggtccg<br>ccgggtgaaccgacccacctggcggtggaggacgttagcgataccaccgtgagcctgaa<br>atggcgtccgccggaacgtgttggtgcgggtggcctggatggctacagcgtggaatattgcc<br>aagagggctgcagcgaatggaccccggcgctgcagggtctgaccgagcgtaccagcat<br>gctggttaaagacctgccgaccggtgcgcgtctgctgttccgtgtgcgtgcgcataacgttgc<br>gggtccgggtggcccgatcgtgaccaaggaaccggttaccgtgcaggagatt[**agcggtg**<br>**atagcgcgacccacattaaatttagcaagcgtgacgaggatggtaaagaactggcg**<br>**ggcgcgaccatggaactgcgtgacagcagcggcaagaccatcagcacctggatt**<br>**agcgatggtcaggttaaagacttctacctgtatccgggcaagtacacctttgtggaaa**<br>**ccgcggcgccggatggttatgaggtggcgaccgcgatcaccttcaccgttaacga**<br>**gcagggtcaagttaccgtgaacggtaaagcgaccaagggc**][gagaatctgtatttcc<br>agggt][catcaccaccaccatcac]taa | |

Table 5 shows non-limiting examples of sequences comprising cMyBP-C with SpyCatcher and SpyTag—

| Description | Sequence | SEQ ID NO: |
|---|---|---|
| SEQ ID NO: 24<br>(C0-C7-SC-ST-C8-C10) | MPEPGKKPVSAFNKKPRSAEVTAGSAAVFEAETERSGV<br>KVRWQRDGSDITANDKYGLAAEGKRHTLTVRDASPDDQ<br>APATELEESVSSPEGSVSVTQDGSAAEHQGAPDDPIGLF<br>LMRPQDGEVTVGGSIVFSARVAGASLLKPPVVKWFKGK<br>WVDLSSKVGQHLQLHDSYDRASKVYLFELHITDAQTTSA<br>GGYRCEVSTKDKFDSCNFNLTVHEAIGSGDLDLRSAFRR<br>TSLAGAGRRTSDSHEDAGTLDFSSLLKKRDSFRRDSKLE<br>APAEEDVWEILRQAPPSEYERIAFQHGVTDLRGMLKRLK<br>GMKQDEKKSTAFQKKLEPAYQVNKGHKIRLTVELADPDA<br>EVKWLKNGQEIQMSGSKYIFESVGAKRTLTISQCSLADD<br>AAYQCVVGGEKCSTELFVKEPPVLITRSLEDQLVMVGQR<br>VEFECEVSEEGAQVKWLKDGVELTREETFKYRFKKDGR<br>KHHLIINEATLEDAGHYAVRTSGGQSLAELIVQEKKLEVY<br>QSIADLAVGAKDQAVFKCEVSDENVRGVWLKNGKELVP<br>DNRIKVSHIGRVHKLTIDDVTPADEADYSFVPEGFACNLS<br>AKLHFMEVKIDFVPRQEPPKIHLDCPGSTPDTIVVVAGNK<br>LRLDVPISGDPAPTVVWQKTVTQGKKASTGPHPDAPED<br>AGADEEWVFDKKLLCETEGRVRVETTKDRSVFTVEGAE<br>KEDEGVYTVTVKNPVGEDQVNLTVKVIDVPDAPAAPKISN<br>VGEDSCTVQWEPPAYDGGQPVLGYILERKKKKSYRWM<br>RLNFDLLRELSHEARRMIEGVAYEMRVYAVNAVGMSRPS<br>PASQPFMPIGPPGEPTHLAVEDVSDTTVSLKWRPPERVG<br>AGGLDGYSVEYCQEGCSEWTPALQGLTERTSMLVKDLP<br>TGARLLFRVRAHNVAGPGGPIVTKEPVTVQEISGDSATHI<br>KFSKRDEDGKELAGATMELRDSSGKTISTWISDGQVKDF<br>YLYPGKYTFVETAAPDGYEVATAITFTVNEQGQVTVNGKA<br>TKGGAHIVMVDAYKPTKLQRPRLQLPRHLRQTIQKKVGE<br>PVNLLIPFQGKPRPQVTWTKEGQPLAGEEVSIRNSPIDTI<br>LFIRAARRTHSGTYQVIVRIENMEDKATLILQIVDKPSPPQ<br>DIRIVETWGFNVALEWKPPQDDGNTEIWGYTVQKADKKT<br>MEWFTVLEHYRRTHCVVSELIIGNGYYFRVFSHNMVGSS<br>DKAAATKEPVFIPRPGITYEPPKYKALDFSEAPSFTQPLA | 24 |

-continued

| Description | Sequence | SEQ ID NO: |
|---|---|---|
| | NRSIIAGYNAILCCAVRGSPKPKISWFKNGLDLGEDARFR MFCKQGVLTLEIRKPCPYDGGVYVCRATNLQGEAQCEC RLEVRVPQ | |

The present invention may also feature a method of producing a recombinant MyBP-C protein. In some embodiments, said method comprises introducing a cassette for expressing a first recombinant MyBP-C protein into a genome of a host. In some embodiments, the first recombinant protein is according to the recombinant protein described herein. In some embodiments, the protease recognition site is adjacent to and 5' to the portion of the split-protein pair. In some embodiments, the method comprises isolating myocytes from the host. In some embodiments, the method comprises introducing to the myocytes a protease that cleaves the first recombinant MyBP-C protein at the protease recognition site to remove its N-terminus and exposes the portion of the split-protein pair. In some embodiments, the method comprises introducing a recombinant MyBP-C N-terminus into the myocytes, the recombinant MyBP-C N-terminus being at least a portion of MyBP-C with a second portion of the split protein pair at its C-terminus. In some embodiments, the second portion of the split protein pair of the MyBP-C N-terminus binds to the portion split-protein pair of the first recombinant MyBP-C to produce a second recombinant MyBP-C protein.

In some embodiments, the present invention features a motility assay platform. In some embodiments, the motility assay platform comprises a coverslip with a thick filament disposed thereon. In some embodiments, the thick filament comprises a recombinant MyBP-C protein as described herein.

Applications

The methods and/or compositions of present invention may be used as a research tool, for example to study cMyBP-C (e.g., to study its function, its features, drug interactions, mutations that lead to diseases, effects of introduced mutations, effects of post-translational modification such as phosphorylation, effects of a longer or shorter domains, effects of stiffer or more compliant domains, etc.), to study diseases such as hypertrophic cardiomyopathy, or for other research purposes. The present invention may also be applied to other proteins, such as skeletal muscle MyBP-C isoforms or other sarcomere proteins. There is also the potential to develop cell lines (e.g., stem cells) with a cassette (e.g., TEV/SpyTag cassette) in cMyBP-C or other sarcomere proteins.

In certain embodiments the methods and/or compositions of the present invention are used in motility assays. For example, in certain embodiments, recombinant cMyBP-C proteins of the present invention may be used in motility assays to test the effects of certain drugs. In certain embodiments, recombinant cMyBP-C proteins of the present invention may be used in motility assays for the purpose of evaluating the effects of mutations or changes in the cMyBP-C protein. The present invention is not limited to these uses for the recombinant cMyBP-C proteins or purposes of motility assays. Standard motility assays have coverslipped slides with attached myosin heads (see FIG. 4), wherein the attached myosin heads can propel fluorescently labeled filaments of actin. The recombinant cMyBP-C proteins of the present invention would be more suitable for motility assays that feature isolated thick filaments linked to a coverslip (see FIG. 5), which allow myosin heads to be in a configuration that is more physiologically relevant and allow for the appropriate positioning and function of cMyBP-C.

Thick filaments for use in such assays can be isolated from systems expressing recombinant cMyBP-C proteins that are constructed using methods of the present invention (e.g., the thick filaments can be isolated from Spy-C mice, from permeabilized myocytes, etc.). These isolated thick filaments can be attached to a coverslip as demonstrated in Previs et al. (Science 2012, 337:1215-1218), and the filaments can be used to test the effects of particular drug (e.g., to see if the drug is an activator or an inhibitor, etc.). In certain embodiments, the filaments featuring recombinant cMyBP-C proteins are used for research purposes, e.g., to evaluate the function or effects of mutations or changes to the cMyBP-C protein. In certain embodiments, force measurements may be used to assess the results of a drug screen or to test the effects of mutations or changes to the cMyBP-C protein. In certain embodiments, the speed of the actin molecules may be assessed to determine the results of a drug screen or to test the effects of mutations or changes to the cMyBP-C protein.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A recombinant protein comprising myosin binding protein C (MyBP-C) with an internal insertion therein, the internal insertion comprises at least a tag portion of a split-protein pair adjacent to a protease recognition site, wherein the internal insertion is within or between C7 and C8 domains of MyBP-C.

2. The recombinant protein of claim 1, wherein the split-protein pair is a SpyTag and SpyCatcher pair.

3. The recombinant protein of claim 1, wherein the split-protein pair is a SnoopTag and SnoopCacher pair.

4. The recombinant protein of claim 1, wherein the tag portion of the split protein pair is a SpyTag.

5. The recombinant protein of claim 1, wherein the tag portion of the split protein pair is a SnoopTag.

6. The recombinant protein of claim 1, wherein the tag portion of the split-protein pair is capable of self-complementation with a polypeptide corresponding to a second portion of the split protein pair.

7. The method of claim 6, wherein the second portion of the split protein pair is a SpyCatcher.

8. The method of claim 6, wherein the second portion of the split protein pair is a SnoopCatcher.

9. The recombinant protein of claim 1, wherein the MyBP-C is cardiac myosin binding protein C (cMyBP-C).

10. The recombinant protein of claim 9, wherein the recombinant cMyBP-C peptide is according to SEQ ID NO: 24.

11. The recombinant protein of claim 1, wherein the MyBP-C is skeletal myosin binding protein C.

12. The recombinant protein of claim 11, wherein the skeletal myosin binding protein C is fast skeletal myosin binding protein C (fMyBP-C).

13. The recombinant protein of claim 11, wherein the skeletal myosin binding protein C is slow skeletal myosin binding protein C (sMyBP-C).

14. The recombinant protein of claim 1, wherein the protease recognition site is a TEV protease recognition site.

15. A method of producing a recombinant MyBP-C protein, said method comprising:

a. introducing a cassette for expressing a first recombinant MyBP-C protein into a genome of a host, wherein the first recombinant protein is according to the recombinant protein of claim 1, wherein the protease recognition site is adjacent to and 5' to the tag portion of the split-protein pair;

b. isolating myocytes from the host;

c. introducing to the myocytes a protease that cleaves the first recombinant MyBP-C protein at the protease recognition site to remove its N-terminus and exposes the tag portion of the split-protein pair;

d. introducing a recombinant MyBP-C N-terminus into the myocytes, the recombinant MyBP-C N-terminus being at least a portion of MyBP-C with a second portion of the split protein pair at its C-terminus;

wherein the second portion of the split protein pair of the MyBP-C N-terminus binds to the tag portion split-protein pair of the first recombinant MyBP-C to produce a second recombinant MyBP-C protein.

16. A motility assay platform comprising: a coverslip with a thick filament disposed thereon, wherein the thick filament comprises a recombinant MyBP-C protein according to claim 1.

* * * * *